(12) United States Patent
Klotsman et al.

(10) Patent No.: US 11,786,505 B2
(45) Date of Patent: *Oct. 17, 2023

(54) METHODS AND COMPOSITIONS FOR DELIVERING MYCOPHENOLIC ACID ACTIVE AGENTS TO NON-HUMAN MAMMALS

(71) Applicant: OKAVA PHARMACEUTICALS, INC., San Francisco, CA (US)

(72) Inventors: Michael Klotsman, San Francisco, CA (US); Padmaja Shivanand, Seattle, WA (US); Wayne H. Anderson, Raleigh, NC (US); Gayatri Sathyan, Karnataka (IN)

(73) Assignee: Okava Pharmaceuticals, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/125,214

(22) Filed: Sep. 7, 2018

(65) Prior Publication Data

US 2019/0201375 A1 Jul. 4, 2019

Related U.S. Application Data

(63) Continuation-in-part of application No. PCT/US2018/022266, filed on Mar. 13, 2018.

(60) Provisional application No. 62/503,270, filed on May 8, 2017, provisional application No. 62/470,806, filed on Mar. 13, 2017.

(51) Int. Cl.
| | |
|---|---|
| *A61K 31/365* | (2006.01) |
| *A61K 9/50* | (2006.01) |
| *A61K 31/343* | (2006.01) |
| *A61K 9/20* | (2006.01) |
| *A61P 37/06* | (2006.01) |
| *A61P 37/02* | (2006.01) |
| *A61K 9/16* | (2006.01) |
| *A61K 9/48* | (2006.01) |

(52) U.S. Cl.
CPC ............ *A61K 31/365* (2013.01); *A61K 9/167* (2013.01); *A61K 9/2072* (2013.01); *A61K 9/5078* (2013.01); *A61K 31/343* (2013.01); *A61P 37/02* (2018.01); *A61P 37/06* (2018.01); *A61K 9/2027* (2013.01); *A61K 9/2054* (2013.01); *A61K 9/4808* (2013.01)

(58) Field of Classification Search
CPC combination set(s) only.
See application file for complete search history.

(56) References Cited

U.S. PATENT DOCUMENTS

| | | | |
|---|---|---|---|
| 4,808,413 | A | 2/1989 | Joshi et al. |
| 5,049,394 | A | 9/1991 | Howard et al. |
| 6,306,900 | B1 | 10/2001 | Haeberlin et al. |
| 2008/0206322 | A1 | 8/2008 | Becker et al. |
| 2010/0056493 | A1 | 3/2010 | Jain et al. |
| 2011/0008426 | A1 | 1/2011 | Jain et al. |
| 2011/0086102 | A1 | 4/2011 | Silver et al. |
| 2011/0223249 | A1 | 9/2011 | Jain et al. |

FOREIGN PATENT DOCUMENTS

| | | |
|---|---|---|
| CN | 1994295 A | 7/2007 |
| CN | 101010070 A | 8/2007 |
| CN | 102793658 A | 11/2012 |
| CN | 103845323 A | 6/2014 |
| KR | 10-2011-0091252 A | 8/2011 |
| WO | 2006/024479 A2 | 3/2006 |
| WO | 2018/170022 A2 | 9/2018 |

OTHER PUBLICATIONS

Guzera (In Vitro Influence of Mycophenolic Acid on Selected Parameters of Stimulated Peripheral Canine Lymphocytes, PLOS ONE | DOI:10.1371/journal.pone.0154429 May 3, 2016, pp. 1-20).*
Soars (Novel application of KI67 to quantify antigen-specific in vitro lymphoproliferation, Journal of Immunological Methods, 362, 2010, 43-50).*
Sandeep (An overview of multiparticulate drug delivery system: Pellets, Int. J. of Pharmacy and Analytical Research, vol. 4(3), 2015, pates 264-275).*
Arns, "Noninfectious Gastrointestinal (GI) Complications of Mycophenolic Acid Therapy: A Consequence of Local GI Toxicity?" *Transplantation Proceedings* 39: 88-93, 2007.
Chanda et al., "Comparative Gastrointestinal Effects of Mycophenolate Mofetil Capsules and Enteric-Coated Tablets of Sodium-Mycophenolic Acid in Beagle Dogs," *Transplantation Proceedings* 34: 3387-3392, 2002.
Chandira et al., "Development and Evaluation of Delayed-Release Tablets of Mycophenolate Sodium," *The Pharma Innovation—Journal* 2(2): 59-67, 2013.
Kamba et al., "Evaluation of the mechanical destructive force in the stomach of dog," *International Journal of Pharmaceutics* 228: 209-217, 2001.
Missaghi et al., "Investigation of Venlafaxine HCl Release from Extruded and Spheronized Beads Coated with Ethylcellulose using Organic or Aqueous Coating Systems," *Controlled Release Society Annual Meeting*, Jul. 2008 (3 pages).
Shipkova et al., "Determination of the Acyl Glucuronide Metabolite of Mycophenolic Acid in Human Plasma by HPLC and Emit," *Clinical Chemistry* 46(3): 365-372, 2000.

(Continued)

*Primary Examiner* — Kathrien A Hartsfield
(74) *Attorney, Agent, or Firm* — SEED INTELLECTUAL PROPERTY LAW GROUP LLP

(57) ABSTRACT

The present disclosure provides methods and compositions for modified delivery of mycophenolic acid active agents, including mycophenolate sodium, in canine subjects. Presently disclosed methods and compositions are useful, for example, to treat autoimmune diseases, blood disorders, and immune rejection related to transplant or graft procedures.

20 Claims, 23 Drawing Sheets

(56) References Cited

OTHER PUBLICATIONS

Winnicki et al., "An inosine 5'-monophosphate dehydrogenase 2 single-nucleotide polymorphism impairs the effect of mycophenolic acid," *The Pharmacogenomics Journal* 10: 70-76, 2010.
International Search Report and Written Opinion, dated Oct. 10, 2018, for International Patent Application No. PCT/US2018/022266, 15 pages.
International Search Report and Written Opinion, dated Jun. 21, 2019, for International Patent Application No. PCT/US2018/050079, 16 pages.
Arns et al., "Enteric-coated mycophenolate sodium delivers bioequivalent MPA exposure compared with mycophenolate mofetil," *Clin. Transplant* 19: 199-206, 2005.
Kohno et al., "9. Mycophenolate mofetil," *Journal of the Japanese Society of Internal Medicine* 100(10):2954-2959, 2011. (with English abstract).
Cellcept Capsule 250, pharmaceutical interview form, revised 17th edition, 2013. (3 pages).

\* cited by examiner

METHODS AND COMPOSITIONS FOR DELIVERING MYCOPHENOLIC ACID ACTIVE AGENTS TO NON-HUMAN MAMMALS

BACKGROUND

Technical Field

Autoimmune diseases represent a heterogeneous family of chronic diseases. The hallmarks of such diseases include activation and/or proliferation of lymphocytes, development of autoantibodies, and dysregulation of the immune system leading to chronic inflammation and tissue damage. In the veterinary context, autoimmune diseases represent a category of diseases with few viable treatment options.

Description of the Related Art

Mycophenolate mofetil has been recognized as a treatment for autoimmune diseases and other conditions in both human and veterinary subjects. However, current methods and compositions for delivery of mycophenolate mofetil and sodium mycophenolate can produce significant side effects in veterinary subjects, including, for example, gastrointestinal intolerance related to mucosal ulceration, and erosion and necrosis of the stomach and the small and large intestines. See, e.g., Arns, W., "Noninfectious Gastrointestinal (GI) Complications of Mycophenolic Acid Therapy: A Consequence of Local GI Toxicity?," Transplantation Proceedings 39:88-93 (2007). Moreover, currently available formulations have uneven pharmacodynamic activity in vivo and require frequent dosing to sustain desired activity.

BRIEF SUMMARY

The present disclosure provides compositions and methods for providing a mycophenolic acid (MPA) active agent to a canine subject in a controlled-release manner. Disclosed compositions and methods possess pharmacodynamic, pharmacokinetic, safety, and/or convenience advantages over immediate-release MPA-containing (e.g., mycophenolate mofetil) formulations. For example, presently disclosed formulations and methods provide controlled-release profiles of a MPA active agent that attain an average plasma [MPA] concentration over about 8 hours in a canine subject such that 2.5, 4, and 8 hours following a first dose of the formulation, lymphocyte proliferation is reduced as compared to a pre-dose amount. In certain embodiments, the canine subject achieves an average plasma [MPA] of about 250 ng/ml to about 3000 ng/ml over about 8 hours following a first dose of the controlled-release formulation, whereupon at 2.5 hours, 4 hours, and 8 hours following the first dose, a percentage of proliferating lymphocytes in a whole blood sample from the subject is reduced as compared to the percentage of proliferating lymphocytes in a whole blood sample obtained from the subject 15 or fewer minutes prior to the first dose, as determined using monoclonal antibody Ki-67.

Further, administration according to the instant disclosure produces a systemic effect such that 24 hours following a second (or more) once-daily dose, and prior to a subsequent dose, the amount of proliferating lymphocytes in a whole blood sample from the canine is lower than the amount of proliferating lymphocytes in whole blood obtained from the canine 15 or fewer minutes prior to the dose of the first day.

In some embodiments, lymphocyte proliferation according to the disclosed controlled-release methods and compositions is reduced by a greater degree and/or for a longer period of time as compared to the reduction attained using an immediate-release formulation comprising a MPA active agent. In certain embodiments, (i) the percentage of proliferating lymphocytes in a whole blood sample obtained from the subject at 4 hours (and/or at 8 hours) following administration of a first dose of controlled-release formulation of the present disclosure is lower than (ii) the percentage of proliferating lymphocytes in a whole blood sample obtained from a reference canine subject that received an immediate-release formulation comprising a MPA active agent.

Moreover, administration of the instantly disclosed formulations to a canine subject surprisingly provides a reduction (i.e., in the number, in the severity, or both) of adverse gastrointestinal events in the subject as compared to an immediate-release formulation comprising a MPA active agent. This occurs even when the amount of MPA active agent administered using a controlled-release formulation exceeds that administered in the immediate-release form.

In certain embodiments, administering comprises administering a single dose for each of 10 or more (optionally 15 or more) consecutive days, wherein over the 10 days (optionally 15 or more days), the subject exhibits no adverse gastrointestinal events, wherein an adverse gastrointestinal event comprises emesis, diarrhea, soft stool, or any combination thereof.

Accordingly, the presently disclosed methods and compositions have utility in, for example, treating an autoimmune disease or disorder in a canine subject, wherein the autoimmune disease or disorder is characterized by aberrant proliferation and/or activation of lymphocytes, as described herein. Autoimmune diseases and disorders treatable using the presently disclosed methods and compositions include atopic dermatitis, arthritis, myasthenia gravis, celiac disease, diabetes mellitus type 1, Grave's disease, inflammatory bowel disease, multiple sclerosis, psoriasis, rheumatoid arthritis, systemic lupus erythematosus, Behçet's disease, pemphigus vulgaris, refractory incomplete systemic lupus erythematosus, lupus nephritis, immunoglobulin A nephropathy, small vessel vasculitides, scleroderma (systemic sclerosis or SSc), idiopathic thrombocytopenic purpura (ITP), psoriasis, apernicious anemia, vitiligo, autoimmune hemolytic disease, glomerulonephritis, immune cytopenias, meningoencephalomyelitis, subepidermal blistering autoimmune disease, immunobullous diseases, cutaneous vasculitis, recurrent erythema multiforme, erythema nodosum, lichen planus, cutaneous Crohn's disease, sarcoidosis, hepatitis, pyoderma gangrenosum, and any combination thereof.

Also provided herein are methods of administering presently disclosed controlled-release formulations that comprise a MPA active agent to a canine subject that has undergone, is undergoing, or will undergo an organ transplant and/or an artificial implant.

In any of the herein disclosed embodiments, the MPA active agent comprises mycophenolate sodium. In any of the herein disclosed embodiments, the canine subject receives a controlled-release formulation in a fed state, or in a fasted state, as described herein. In certain embodiments, a controlled-release formulation is administered orally.

Controlled-release formulations comprising a MPA active agent, and kits comprising the formulations, are also provided.

In another aspect, the present disclosure provides uses of the controlled-release compositions to suppress lymphocyte proliferation in a canine subject.

In a further aspect, methods are provided for manufacturing a medicament comprising a controlled-release formulation of the present disclosure.

Further aspects, embodiments, features, and advantages of the disclosure, as well as the structure and operation of the certain embodiments, are described in detail below with reference to accompanying drawings.

BRIEF DESCRIPTION OF THE SEVERAL VIEWS OF THE DRAWINGS

FIG. 17 shows the design of the 15-day study. In the depicted study arm, male beagle dogs received a "base dose" of the controlled-release composition (270 mg, containing 252 mg MPA; QD); a "low dose" once-daily (180 mg, containing 168 mg MPA; QD); or a "low dose" twice-daily (180 mg, containing 168 mg MPA; BID). In each treatment group, n=5 dogs. In a parallel study (not shown), dogs received an immediate-release mycophenolate mofetil formulation (120 mg; ~10 mg/kg for approximately 12 kg dogs) MMF, BID; n=5) or placebo (n=1).

FIG. 18 illustrates the data capture timeline for the open-label study shown in FIG. 17. PD endpoints were collected at Days 1, 8, and 15. On each endpoint collection day, a total of four (4) sampling timepoints were used, as shown in Table 17 herein.

FIG. 19 shows the percentage of lymphocytes expressing the Ki-67 antigen, a marker associated with proliferation, in whole blood samples taken from male beagle dogs prior to, or 2.5 hours, 4 hours, or 8 hours following oral administration of a controlled-release formulation of the present disclosure (containing 252 mg MPA, QD) during a 15-day pharmacodynamics study. Ki-67 expression was determined using monoclonal antibody Ki-67 in samples taken at Days 1, 8 and 15 of the study. The indicated percentages on the Y-axis are with reference to baseline (i.e., percent of baseline Ki67+ cells (+/−SD)) such that lower bars represent a reduction in expression as compared to baseline.

FIG. 20 shows the overall percentage of lymphocytes expressing the Ki-67 antigen in whole blood samples taken from male beagle dogs prior to, or 2 hours, 4 hours, or 8 hours following a single oral administration of a controlled-release formulation of the present disclosure.

FIG. 21 shows the percentage of lymphocytes expressing the Ki-67 antigen in whole blood samples taken from male beagle dogs prior to, or 2.5 hours, 4 hours, or 8 hours following oral administration of a controlled-release formulation (180 mg, containing 168 mg MPA, QD) of the present disclosure. Samples were taken at Days 1, 8, and 15 of the 15-day study. The indicated percentages are with reference to baseline.

FIG. 22 shows the percentage of lymphocytes expressing the Ki-67 antigen in whole blood samples taken from male beagle dogs prior to, or 0.75 hours, 4 hours, or 8 hours following oral administration of an immediate-release mycophenolate mofetil formulation (120 mg MMF; BID). Samples were taken at Days 1, 8, and 15 of the 15-day study. The indicated percentages are with reference to baseline.

FIG. 23 shows a comparison of single-dose (Day 1) pharmacodynamics of an immediate-release mycophenolate mofetil formulation (120 mg MMF), BID) and of a controlled-release formulation of the present disclosure (270 mg, containing 252 mg MPA; QD). Ki-67 expression was measured in whole blood samples taken from male beagle dogs at the indicated timepoints. The indicated percentages are with reference to baseline.

FIG. 24 shows a comparison of pharmacodynamics of an immediate-release mycophenolate mofetil formulation (120 mg MMF, BID) and a controlled-release formulation of the present disclosure (270 mg, containing 252 mg MPA; QD) on days 8 and 15 of the 15-day study. Ki-67 expression was measured in whole blood samples taken from male beagle dogs at the indicated timepoints. The indicated percentages are with reference to baseline.

FIG. 25 shows an eight-hour pharmacokinetic profile (mean plasma MPA concentration) in male beagle dogs administered a controlled-release formulation of the present disclosure (270 mg, containing 252 mg MPA) measured following 8 days of administration (QD) in the presently disclosed 15-day study. N=5 male beagle dogs.

FIG. 26 shows eight-hour pharmacokinetic profiles (mean plasma MPA concentration) in male beagle dogs administered a controlled-release formulation of the present disclosure (180 mg, containing 168 mg MPA; administered BID or QD) measured following 8 days of administration in the presently disclosed 15-day study. N=5 male beagle dogs per treatment group.

DETAILED DESCRIPTION

Figure 2:
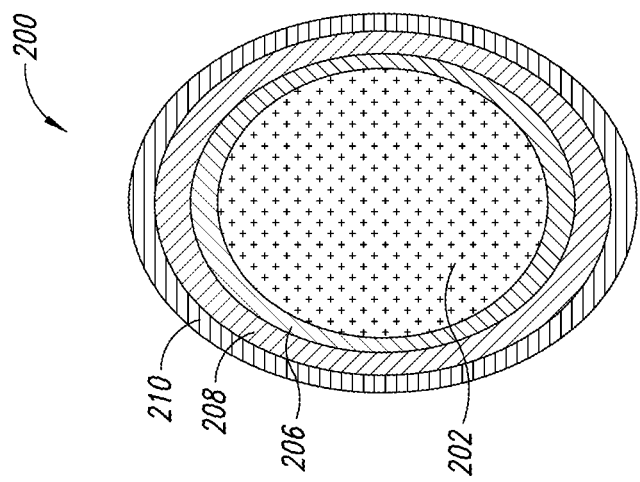
FIG. 2 shows a representation of an embodiment of a further particulate subunit of a controlled-release formulation in accordance with an embodiment hereof.

The present disclosure provides methods and compositions for controlled delivery of mycophenolic acid active agents, including mycophenolate sodium, in veterinary subjects. The methods and compositions disclosed herein are useful for, among other applications, suppressing lymphocyte proliferation (e.g., reducing the number of proliferating lymphocytes) in a veterinary subject, and for treating autoimmune diseases, blood disorders associated with aberrant lymphocyte proliferation and/or activation, and immune rejection related to transplant or graft procedures.

The published patents, patent applications, websites, company names, and scientific literature referred to herein are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of this specification.

Definitions

Prior to setting forth this disclosure in more detail, it may be helpful to an understanding thereof to provide definitions of certain terms to be used herein. Additional definitions are set forth throughout this disclosure.

Technical and scientific terms used herein have the meaning commonly understood by one of skill in the art to which the present application pertains, unless otherwise defined. Reference is made herein to various methodologies and materials known to those of ordinary skill in the art.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

"Optional" or "optionally" means that the subsequently described element, component, event, or circumstance may or may not occur, and that the description includes instances in which the element, component, event, or circumstance occurs and instances in which they do not.

The term "consisting essentially of" is not equivalent to "comprising" and refers to the specified materials or steps of a claim, or to those that do not materially affect the basic characteristics of a claimed subject matter.

The terms "gastrointestinal tract," "GI tract," and "GI" may be used interchangeably herein and refer to an organ system in veterinary subjects which takes in food, digests the food to extract and absorb energy and nutrients, and expels the remaining waste. The GI tract is commonly considered to comprise two subparts: the upper GI tract (also "upper GI" herein) includes the buccal cavity, pharynx, esophagus, stomach, and duodenum, and the lower GI tract (also "lower GI" herein) includes the small and large intestines, the jejeunum, the ileum, the colon, the cecum, the rectum, the anal canal, and the anus.

The terms "MPA active agent" and "mycophenolic acid active agent" may be used interchangeably herein and refer to MPA or a MPA-based ingredient (e.g., of a veterinary composition of the present disclosure) that exerts a physiological or pharmacodynamic effect on a subject. MPA active agents comprise MPA and pharmaceutically acceptable salts, esters, prodrugs, homologs, hydrates or solvates thereof. In certain embodiments, a MPA active agent comprises mycophenolate sodium. In certain embodiments, a MPA active agent comprises MMF.

As used herein, "bioavailability" refers to the fraction of a drug that is absorbed and therefore available to produce a physiological effect. Bioavailability may be measured by quantifying the AUC, by, for example, plotting serum concentration over time plots using labeled drugs and mass spectroscopy. Bioavailability can be measured in terms of "absolute bioavailablity" or "relative bioavailablity."

Absolute bioavailability ($F_{abs}$) relates to bioavailability when administered in a non-intravenous dosage form (e.g., oral tablet) compared with the same drug administered intravenously. Absolute bioavailability may be determined by comparing the AUC of the non-i.v. and i.v. forms, and correcting for the respective doses:

$$F_{abs} = (AUC_{non\text{-}intravenous} / AUC_{intravenous}) * (Dose_{intravenous} / Dose_{non\text{-}intravenous})$$

Relative bioavailability ($F_{rel}$) compares the bioavailability of two different dosage forms of a drug. The relative AUCs for each dosage form are compared and relative doses are used to normalize the calculation:

$$F_{rel} = (AUC_{dosageA} / AUC_{dosageB}) * (Dose_B / Dose_A)$$

Pharmacodynamics ("PD"), as used herein, refers to the biochemical or physiological effect or effects of a drug on a subject. PD may be described in the context of a dose-response relationship or a concentration-response relationship, and may encompass a range of desirable, undesirable, or neutral effects through mechanisms such as stimulating or depressing action through receptor agonism and downstream effects, blocking or antagonizing action (e.g., of a signaling pathway, or catalytic activity of an enzyme, or the like), stabilizing action, exchanging, replacing, or accumulating substances (e.g., glycogen storage), conferring a direct beneficial chemical reaction, or conferring a direct harmful chemical reaction (e.g., cytotoxicity, mutagenesis, or irritation). PD values described herein with respect to MPA compositions and related methods include, for example, adverse effects on a canine subject administered an MPA active agent (e.g., adverse gastrointestinal events such as diarrhea, soft stools, emesis, or the like), autoantibody levels or activity, cytokine release rate or levels, inflammation, and B or T lymphocyte count(s) or functionality(ies), including proliferation, e.g., as determined by the presence of the proliferation-associated marker antigen Ki-67. Other markers and assays for determining proliferation of lymphocytes are known in the art and are contemplated herein. Suppression of lymphocyte proliferation may be measured by a reduction in the percentage of proliferating lymphocytes in a whole blood sample, and can be reported as a reduction relative to a baseline level, as a raw percentage, or by other accepted means. As set forth in additional detail herein, Ki-67 expression can be measured using monoclonal antibody Ki-67 ("mAb-Ki-67").

As used herein, a "canine" refers to any member of the family Canidae, and includes domestic dogs (including any breed or any variant thereof, as well as any combination of two or more breeds or variants, and combinations thereof), wolves, foxes, jackals, and coyotes.

"Autoimmune disease" and "autoimmune disorder" may be used interchangeably herein and refer to conditions in which the immune system of a subject recognizes the subject's own cell(s) or tissue(s) as antigenic and produces an inflammatory response against the subject's cell(s) or tissue(s).

In some embodiments, an autoimmune disease or disorder is associated with aberrant lymphocyte proliferation and/or activation. Aberrant proliferation of lymphocytes includes, for example, increased proliferation (e.g., an increase in the overall percentage of lymphocytes in a population that are proliferating; an increase in the rate of proliferation of a single lymphocyte or of a population of lymphocytes; or an increase in the speed of one or more cycles of cell division by a lymphocyte or population of lymphocytes, relative to a normal baseline; proliferation induced exposure to healthy cells or tissues, rather than, for example, a mitogen, a cancer antigen, or an antigen associated with an infection) and proliferation that results in abnormal and/or dysfunctional lymphocytes, including lymphocytes with a decreased native functionality and lymphocytes with an acquired undesirable functionality, such as autoreactivity. Aberrant activation of lymphocytes refers to one or more aberration in a functionality of a lymphocyte that typically occurs following contact with an antigen or mitogen, such as the production of lymphokines, the enlargement of cytoplasm, the synthesis of macromolecules (e.g., antibodies), and differentiation into memory and effector cell types.

In certain embodiments, compositions and methods according to the present disclosure are useful to treat an (i.e., one or more) autoimmune disease, such as, for example, atopic dermatitis, rheumatoid arthritis, celiac disease, diabetes mellitus type 1, Grave's disease, inflammatory bowel disease, multiple sclerosis, psoriasis, systemic lupus erythematosus, Behçet's disease, pemphigus vulgaris, refractory incomplete systemic lupus erythematosus, lupus nephritis, immunoglobulin A nephropathy, small vessel vasculitides, scleroderma (systemic sclerosis or SSc), idiopathic thrombocytopenic purpura (ITP), myasthenia gravis, psoriasis, pernicious anemia, vitiligo, autoimmune hemolytic disease, glomerulonephritis, immune cytopenias, meningoencephalomyelitis, subepidermal blistering autoimmune disease, immunobullous diseases, cutaneous vasculitis, recurrent erythema multiforme, erythema nodosum, lichen planus, cutaneous Crohn's disease, sarcoidosis, immune reactions associated with veterinary transplant or implant procedures (e.g., tissue transplants, grafts, and device implants), including host-versus-graft disease (HvGD) and other forms of implant rejection, hepatitis, and pyoderma gangrenosum. Blood disorders or diseases treatable according to the presently disclosed methods and compositions include, but are not limited to, aplastic anemia, immune mediated hemolytic anemia, and immune-mediated thrombocytopenia.

In some embodiments, the presently disclosed compositions and methods are useful in providing immunosuppression (e.g., by suppressing proliferation and/or activation of lymphocytes) in a canine subject that has undergone, is undergoing, or will undergo an organ transplant and/or an artificial implant (e.g., a corneal implant, an artificial implant or replacement of a joint, a ligament, a bone, or the like).

"Treat," "treatment," and "ameliorate," as used herein, refer to the prevention, lessening of the likelihood of, or medical management of a disease, disorder, or condition of a subject (e.g., a canine having a an autoimmune disease or disorder associated with aberrant lymphocyte proliferation, or a surgical graft or transplant). A canine subject according to the presently disclosed methods and compositions may, but need not necessarily, be evaluated, diagnosed, or treated by a veterinarian or other veterinary care professional). In general, a dose or treatment regimen comprising a controlled-release veterinary composition of the present disclosure is administered to the canine subject in an amount sufficient to elicit a therapeutic or prophylactic benefit. Therapeutic or prophylactic/preventive benefits include, but are not limited to: improved clinical outcome; lessening or alleviation of symptoms associated with a disease; reduced frequency of occurrence of symptoms; improved quality of life; longer disease-free status; diminishment of extent of disease, stabilization of disease state; delay of disease onset, progression; remission; survival; prolonged survival; or any combination thereof.

A "therapeutically effective amount" or "effective amount" of a MPA active agent or a controlled-release formulation of the present disclosure refers to an amount sufficient to result in a therapeutic effect, including: improved clinical outcome; lessening or alleviation of symptoms associated with a disease; decreased occurrence of symptoms; improved quality of life; longer disease-free status; diminishment of extent of disease; stabilization of disease state; delay of disease progression; remission; survival; or prolonged survival in a statistically significant manner. For example, a therapeutically effective amount of a MPA active agent according to the compositions and methods of the present disclosure may be an amount sufficient to reduce or delay proliferation and/or activation of B or T lymphocytes, to prevent, reduce, or ameliorate an inflammatory response in a canine subject; to treat an autoimmune disease or disorder; or to prevent, reduce the severity of, or delay the onset of a rejection occurring in the course of a cell, organ, or tissue transplant or graft. When referring to an individual active ingredient, administered alone, a therapeutically effective amount refers to the effects of that ingredient alone. When referring to a combination, a therapeutically effective amount refers to the combined amounts of active ingredients that result in a therapeutic effect, whether administered sequentially, contemporaneously, or simultaneously.

As used herein, "modulating" means reducing, raising, hastening, delaying, or preventing an occurrence, or increasing or decreasing the intensity or efficiency of the occurrence being modulated, through either direct or indirect means.

The term "controlled-release" is used to describe products that alter the timing and/or the rate of release of the drug substance in a way that deviates from immediate-release following administration. A controlled-release dosage form is a formulation in which the drug-release characteristics of time, course, and/or location are chosen to accomplish therapeutic or convenience objectives not offered by immediate-release dosage forms such as immediate-release tablets or suspensions or other promptly dissolving or releasing dosage forms. Controlled-release oral drug formulations include, for example, extended-release formulations (which allow a reduction in dosage frequency as compared to the same drug presented as an immediate-release (conventional) dosage form, e.g., sustained-release and long-acting formulations); delayed-release formulations (which release an identifiable portion or portions of drug at a time other than promptly after administration, e.g., enteric-coated aspirin and other NSAID products); targeted-release formulations (which release the drug at or near the intended physiologic site of action, and may have either immediate- or extended-release characteristics); and orally disintegrating tablets (ODT), which disintegrate rapidly in the saliva after oral administration. The terms "controlled-release," "modified-release," "sustained-release," "extended-release," "long-acting," "targeted-release," and "delayed-release" may be used interchangeably herein to refer to the release of an administered MPA active agent in a way that deviates from immediate release following administration. As used herein, an "immediate release" dosage refers to any dosage form that is formulated to release or make available the active ingredient immediately upon administration. A controlled-release formulation according to the present disclosure may, in certain embodiments, be formulated or administered to achieve one or more of the following characteristics: release of a MPA active agent at or within a certain time following administration; release of a MPA active agent under specific physiological conditions (e.g., pH, temperature); release of a MPA active agent within a particular part of the body based on known, estimated, or predicted digestive, circulatory, or metabolic rates; release of a MPA active agent with, upon, or following administration with another reagent; in a predetermined amount; release of a MPA active agent for a predetermined amount of time; release of a MPA active agent according to particular release profile; or any combination thereof.

Certain embodiments of the presently disclosed controlled-release formulations comprise a means for controlling release of the MPA active agent so that the MPA active agent is released from the formulation in vivo such that a canine subject administered the MPA active agent at a single dose achieves a desired PK effect and a desired PD effect, as described herein. Various means for controlling in vivo release of a MPA active agent are known and described further herein, and include, for example, cellulose polymers, acrylate polymers, cellulose acetates, cellulose acetate butyrates, ethyl celluloses, hydroxypropyl methyl celluloses, methyl cellulose polymers, ethyl celluloses, hydroxypropyl methyl celluloses, methyl cellulose polymers, EUDRAGIT® polymers for controlled release, poly(vinyl acrylate) (PVA) polymers (e.g., KOLLIDON® series), poly(vinyl acrylate) (PVA) polymers, or any combination thereof. Means for controlling release of a MPA active agent also comprise layers comprising one or more of the herein-described materials (optionally combined with one or more other materials), which layers can be present in any number, type, and thickness as appropriate to achieve a desired controlled-release. Examples of such layers include controlled-release layers, protective layers, and seal coat layers, which are described herein.

The terms "pharmaceutically acceptable excipient or carrier" or "physiologically acceptable excipient or carrier," as used herein, refer to non-active biologically compatible vehicles, which are described in greater detail herein, that are suitable for administration to a human or other non-human mammalian (e.g., canine) subject and generally recognized as safe or not causing a serious adverse event. In certain embodiments, a pharmaceutically acceptable carrier includes food items or liquids to be administered to the subject. For example, a controlled-release formulation of the present disclosure can be sprinkled on, sprayed on, or otherwise added to, or combined with, food (including "treats") or water to be consumed by a canine subject. In certain embodiments, a MPA composition of the present disclosure may be carried by (i.e., contained within, combined with, or coated on) a food item such as a dry dog food, a treat, a bone, or the like. Feeding regimes useful for practicing such embodiments are described herein.

As used herein, "statistically significant" refers to a p value of 0.050 or less when calculated using the Students t-test and indicates that it is statistically unlikely that a particular event or result being measured has arisen by chance.

MPA, MPA Active Agents, and Pharmacology Thereof

Mycophenolic acid ($C_{17}H_{20}O_6$; "MPA") is a nonnucleoside, noncompetitive, reversible inhibitor of the enzyme inosine 5'-monophosphate dehydrogenase (IMPDH), which catalyzes the synthesis of xanthine monophosphate (XMP) from inosine-5'-monophosphate (IMP). IMP→XMP is the rate-limiting step in the de novo synthesis of guanine nucleotides required for nucleic acid synthesis, proliferation, and differentiation cells, including B and T lymphocytes. By inhibiting IMPDH activity, MPA acts as an immunosuppressive agent. See, e.g., Arns, W., *Transplantation Proceedings* 39:88-93 (2007), the disclosure and methods of which are herein incorporated by reference in their entirety. MPA has the following basic structure shown in Formula I:

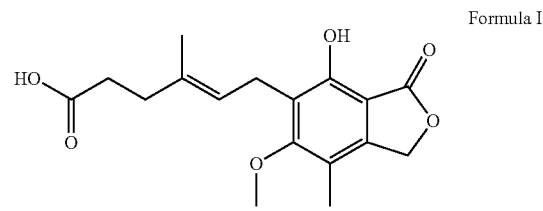 [SMILES: COc1c(C)c2c(c(O)c1C/C=C(\C)CCC(=O)O)C(=O)OC2]

Formula I

IMPDH has two isoenzymes, IMPDH1 and IMPDH2. The former is expressed in most cell types, while the latter predominates in activated lymphocytes (see, e.g., Winnicki et al., *Pharmacogenomics J.* 10(1):70-6 (2009)). MPA inhibits IMPDH2 up to 4- to 5-fold more than IMPDH1, and therefore has a more potent cytostatic effect on activated lymphocytes than on other cells.

MPA has been prepared for use in humans as an adjunctive immunosuppressant as a mycophenolate mofetil ester (MMF; approved for human use in the U.S. as CellCept®) and as Na.MPA (Myfortic®).

Adverse drug reactions (≥1% of human patients) associated with mycophenolate therapy (i.e., any single-dose or multi-dose therapeutic regimen involving use of MPA or an active agent thereof, as defined herein) include diarrhea, nausea, loose stools, emesis, joint pain, infections, leukopenia, and anemia. Mycophenolate sodium is also commonly associated with fatigue, headache, cough and/or breathing issues. Intravenous (IV) administration of MMF is also commonly associated with thrombophlebitis and thrombosis. Adverse effects associated with MMF use (0.1-1% of subjects) include esophagitis, gastritis, diarrhea, loose stools, emesis, gastrointestinal tract hemorrhage, and/or invasive cytomegalovirus (CMV) infection. Less frequently, pulmonary fibrosis or various neoplasia occur, such as, for example, melanoma, lymphoma, and other malignancies, which MMF-related neoplasias can occur at frequencies of 1 in 20 to 1 in 200, depending on the type, with neoplasia in the skin being the most common site. Cases of pure red cell aplasia (PRCA) have also been reported.

Compositions and methods according to the present disclosure may be described in pharmacological terms, including pharmacokinetics ("PK") and pharmacodynamics ("PD"). As is understood in the art, pharmacokinetics relate to the fate—e.g., the concentration, metabolism, distribution, absorption, half-life, or excretion—of a drug administered to an organism. Non-limiting measures of PK include $C_{max}$ (the maximum serum concentration of a drug in a specified compartment or test area of the body), $T_{max}$ (the time at which the $C_{max}$ is observed), $C_{min}$ (minimum or trough concentration), $T_{min}$ (time at which $C_{min}$ is observed), $T_{1/2}$ (half-life of the drug or metabolite, i.e., the time taken for the drug concentration to fall to one half of its original value, which may be calculated using one or more points along the terminal phase of the elimination), elimination rate constant "k" (the slope calculated using one or more concentrations in the log domain the terminal phase), and AUC ("area under the curve"; the definite integral in a plot of concentration of a drug in blood plasma over time). AUC represents the total drug exposure over time in a given dose or dosing regimen, and may be computed starting at the time of administration and ending when the plasma concentration is minimal, or may be measured at chosen points in time and calculated therefrom. It will be appreciated that certain PK values, such as $C_{max}$ and $C_{min}$, may be reported with respect to particular timeframes herein, e.g., a particular time window, or a particular number of hours, following administration of a controlled-release formulation.

PK values described herein with respect to MPA compositions and related methods include, for example, [MPA] (concentration of mycophenolic acid drug), [MPAG], and [Acyl-MPAG]. Serum or plasma concentrations of a drug or metabolite may be reported in any appropriate unit, such as, for example, ng/mL, mg/kg, µg/mL, µg/L, and so on. Concentrations over time may be reported in any appropriate unit, such as, for example, µg*h/L or ng*h/mL. The AUC may be used to report the concentration over a given time interval ($AUC_t$) or unbound by a particular time interval ($AUC_{inf}$).

Other measures of MPA PK include, for example, drug:metabolite ratios, e.g., drug:metabolite ratios obtainable following administration of a MPA-containing agent (e.g., an immediate-release formulation or a controlled-release formulation of the present disclosure).

Moreover, presently disclosed methods and compositions may, in some embodiments, possess desired MPA pharmacodynamics. For example, in some embodiments, presently disclosed methods and compositions of the present disclosure may be used for e.g., reducing lymphocyte proliferation, providing immunosuppression, modulating an inflammatory response in a canine subject, and providing MPA-based therapies with improved safety profiles.

Formulations and Kits

In certain aspects, controlled-release formulations are provided, wherein the formulations comprise: about 3 mg to about 2.2 g of a MPA active agent; and (ii) a means for controlling release of the MPA active agent so that the MPA active agent is released from the formulation in vivo such that a canine subject administered the MPA active agent at a single dose of about 21 mg/kg achieves a plasma [MPA] Cmax of up to about 3000 ng/ml (e.g., about 1000, 1500, 2000, 2500, or about 3000 ng/ml) over about 8 hours following the single dose, and a plasma [MPA] Cmin of no less than about 250 ng/mL from about 2.5 to about 8 hours following the first dose, and the subject achieves an average plasma [MPA] of 250 ng/ml to about 2000 ng/ml for about 8 hours following the single dose, and whereupon at 2.5 hours, 4 hours, and 8 hours following the single dose, a percentage of proliferating lymphocytes in a whole blood sample from the subject is reduced as compared to the percentage of proliferating lymphocytes in a whole blood sample obtained from the canine 15 or fewer minutes prior to the single dose, as determined using monoclonal antibody Ki-67.

In some embodiments, the total amount of the MPA active agent present in the controlled-release formulation is about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 81, 82, 84, 85, 86, 87, 88, 89, 90, 91, 92, 93, 94, 95, 96, 97, 98, 99, 100, 105, 110, 115, 120, 125, 130, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1100, 1200, 1300, 1400, 1500, 1600, 1700, 1800, 1900, 2000, 2100, or 2200 mg.

In some embodiments, the MPA active agent comprises mycophenolate sodium. In particular embodiments, the formulation comprises about 180 mg of mycophenolate sodium. In other embodiments, the formulation comprises about 270 mg of mycophenolate sodium.

Figure 3:
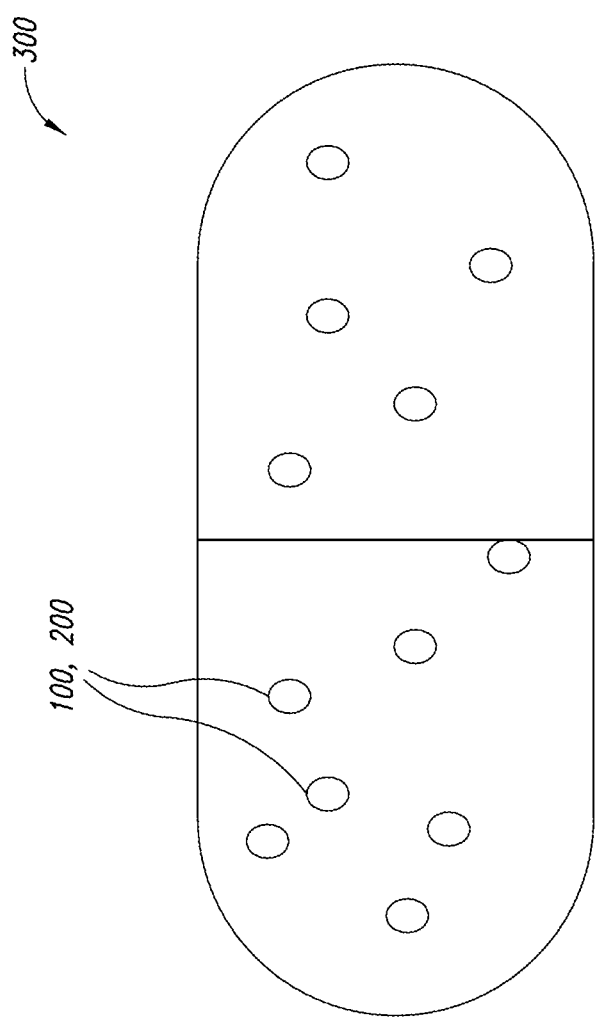
FIG. 3 shows a representation of an embodiment of a controlled-release formulation according of the present disclosure, in the form of a capsule, comprising particulate subunits in accordance with the present disclosure.

Any suitable delivery system may be used to deliver a formulation of the instant disclosure, such as, for example:

(i) a multiparticulate drug delivery system (MDDS) containing a plurality of particulate subunits that each comprise the MPA active agent; (ii) a tablet; (iii) a suspension; (iv) a dragee; (v) a minitablet; or (vi) any combination thereof. For example, as shown in FIG. 3, a capsule 300 includes a plurality of subunits 100, 200, dispersed or mixed within the capsule 300.

The term "multi-particulate drug delivery system," also abbreviated herein as "MDDS," refers to a multi-unit drug dosage form comprising a plurality of discrete particulate subunits (e.g., granules, beads, microspheres, spheroids, pellets, and minitablets) that contain or otherwise carry the drug to be delivered. MDDS of the present disclosure are controlled-release oral compositions that release a MPA active agent in vivo along a desired release profile, and include, for example, tablets (including minitablets), capsules, dragees, sachets, and suspensions that comprise particulate subunits. A "particulate subunit," as described herein, refers to a drug-containing subunit of a MDDS, and can take the form of, for example, a bead, a granule, a microsphere, a spheroid, a pellet, or the like, as described further herein.

In certain embodiments, a formulation comprises a MDDS that is prepared for delivery via a capsule, a sachet, a tablet, or any combination thereof. In certain embodiments, a MDDS comprises a single type of a particulate subunit. In other embodiments, a MDDS comprises multiple types of the particulate subunits. For example, a MDDS may comprise a mixture of particulate subunits having different release characteristics so as to achieve a desired drug release profile in a canine subject. Thus, in certain embodiments, a plurality of particulate subunits having cores of different sizes, or the presence or absence of a protective layer (described herein), or other characteristics may be present in a MDDS of the present disclosure. Without wishing to be bound by theory, this flexibility advantageously permits selecting or calibrating a MDDS for a specific canine subject (e.g., an individual canine) or for a population or subpopulation of canine subjects (e.g., a breed or species of canine) as may be warranted by characteristics such as the specific size, activity, level, responsiveness to a pending or prior treatment, general health, metabolic rate or function, and other specific characteristics of the canine subject. Particulate subunits include, for example, beads, granules, microspheres, spheroids, pellets, and minitablets.

Figure 1:
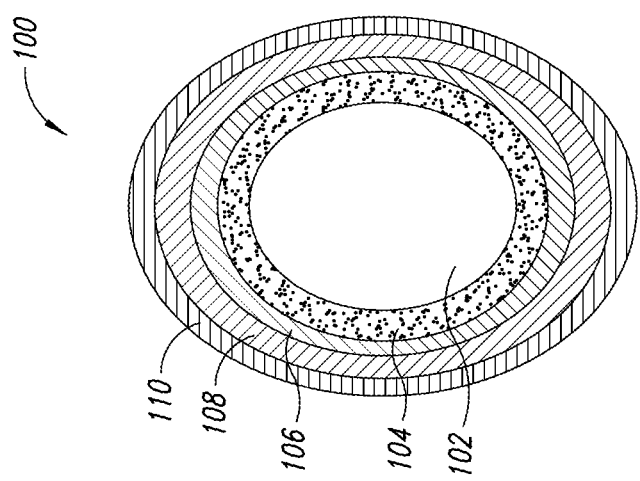
FIG. 1 shows a schematic example of a particulate subunit of a controlled-release formulation of the present disclosure.

In certain embodiments, a particulate subunit (e.g., FIG. 1, 100) includes a core and a MPA active agent. In further embodiments, a core (e.g., FIG. 1, 102) of a particulate subunit 100 comprises a solid support core, such as, for example, a sugar bead, a sugar sphere, a nonpareil bead, a microcrystalline cellulose bead, a silica bead, a calcium carbonate bead, a tartaric acid bead, a mannitol bead, a lactose bead, a starch bead, or another pharmaceutically acceptable core onto which an MPA active agent and other layers described herein can be disposed. In some embodiments, a core 102 comprises an active agent layer (e.g., FIG. 1, 104) disposed over at least a portion of the core 102 (e.g., disposed over a portion, or all, of the core 102). The MPA active agent may be disposed over core 102 using methods known in the art, such as, for example, spray coating, extrusion, suspension layering, dry powder layering, spray granulation, direct pelletizing, dip coating, layering, painting, deposition methods, and the like (see, e.g., methods outlined by Glatt GmbH, Binzen, Germany, www.glatt.com).

In alternative embodiments, as exemplified in FIG. 2, a core 202 is an extruded core, in which the MPA active agent is contained. Extruded cores can be prepared as described, for example, in U.S. Pat. Nos. 4,808,413 and 5,049,394 (the disclosures of each of which are incorporated by reference herein in their entireties), and may include a binder-plasticizer (e.g., a non-lipophilic binder-plasticizer (such as microcrystalline cellulose)), an excipient (e.g., a starch-based excipient) or a binder. Additional exemplary extruded cores can be prepared as described in Missaghi et al., "Investigation of Venlafaxine HCl Release from Extruded and Spheronized Beads Coated with Ethylcellulose Using Organic or Aqueous Coating Systems," Controlled Release Society Annual Meeting July 2008, the disclosure of which is incorporated by reference herein in its entirety for all purposes.

For example, in certain embodiments, extruded core 202 includes a MPA active agent (e.g., mycophenolate sodium) from about 50 wt % to about 90 wt %, an extrusion/spheronization aid, such as microcrystalline cellulose, from about 10 wt % to about 30 wt %, or from about 15 wt % to 20 wt %. As used herein, the amount of a substance in a composition may be described "by weight," by "percent weight," or "wt %," meaning the weight of a substance relative to the weight of an individual composition (e.g., a single particulate subunit) rather than relative to the total weight of the MDDS comprising the plurality of the particulate subunits). In certain embodiments, an extruded core 202 further comprises one or more of: a binder (e.g., hydroxypropyl cellulose, hydroxyl propyl methyl cellulose, pregelatinized starch, ethyl cellulose or poly vinyl pyrrolidone) from about 1 wt % to about 10 wt %, preferably from about 2 wt % to about 5 wt %; a release excipient, such as, for example, hydroxypropyl methyl cellulose (HPMC), hydroxypropyl cellulose (HPC), acrylic polymers, hydroxyethyl cellulose (HEC), ethyl cellulose (EC), which can be incorporated into the beads or applied as coating; a filler, such as, for example, lactose, maltodextrin, mannitol, sorbitol, dicalcium phosphate, and the like; and a superdisintegrant, such as, for example, crosslinked poly(vinyl pyrrolidone) (PVP), sodium starch glycolate, or sodium croscarmellose, and the like.

In embodiments having an extruded core (e.g., extruded core 202), at least a portion of the MPA active agent can be dispersed, dissolved, mixed in, or otherwise distributed throughout the core. For example, the MPA active agent may be co-dissolved with the various polymers and other excipients for producing the extruded cores, and then passed through an extruder to form the desired size beads, prior to drying. Methods suitable for making extruded cores according to the presently disclosed particulate subunits are described in, for example, U.S. Pat. No. 5,049,394, which methods are incorporated herein by reference.

It will be appreciated that an extruded core 202 of the present disclosure may also have an active layer (i.e., of MPA active agent) disposed partially or fully thereover.

In certain embodiments, and without wishing to be bound by theory, the size of the core 102, 202 of a particulate subunit can be important to ensure sufficient delivery of a MPA active agent to a canine subject. For example, in certain instances it has been reported that canines do not readily pass objects above certain dimensions in the lower GI. Accordingly, in any of the herein disclosed embodiments, a particulate subunit core can have a diameter of about 0.5 mm to about 10 mm. For example, in some embodiments, a diameter of a core (e.g., 102, 202) is from about 0.5 mm to about 9 mm, about 1 mm to about 8 mm, about 1 mm to about 7 mm, about 1 mm to about 6 mm, about 1 mm to about 5 mm, about 2 mm to about 5 mm, about 2 mm to about 4 mm, or about 1 mm, about 2 mm, about 3 mm, about 4 mm, about 5 mm, about 6 mm, about 7 mm, about 8 mm, about 9 mm, or about 10 mm in diameter. In certain embodiments, the diameter of the core is about 5 mm or less, or is about 2 mm to about 4 mm. For example, in some canine subjects, a core diameter of less than about 5 mm allows the particulate subunit, once freed or dispersed from an administered MDDS, to move readily through the stomach of a canine subject, in particular, through a canine stomach and into the upper and then lower gastrointestinal tract for delivery of the MPA active agent. For some canine subjects, particulate subunit with cores having a diameter of greater than about 5 mm may remain in the stomach for an undesirably long period of time, thereby impacting the targeted delivery of the MPA active agent.

In addition, the crushing strength of the stomach of certain canines can be significantly higher than the crushing strength of a human stomach (about 1.5N (human) vs. about 3.2N (canine); (see, e.g., Kamba et al., *Int. J. Pharmaceutics* 228(1-2):209-217 (2001)). Thus, in particular embodiments, smaller-sized cores, such as cores having diameters of less than about 5 mm, may prevent a particulate subunit from being crushed in the stomach, which may cause premature (and therefore less effective and possibly adverse) release of a MPA active agent in the stomach of the canine subject.

In some embodiments, particulate subunits (100, 200) of the present disclosure include a controlled-release layer 108, 208 disposed over at least a portion of core 102 or 202. As used herein, a "controlled-release layer" refers to a layer of material that provides release of a MPA active agent over a pre-determined time or period of time, or at a pre-determined rate, or otherwise along a release profile that does not include immediate release of a MPA active agent following administration. Non-limiting examples of materials suitable for forming a controlled-release layer include various polymers, such as cellulose polymers or acrylate polymers, cellulose acetates, cellulose acetate butyrates, ethyl cellulose, hydroxypropyl methyl cellulose, methyl cellulose polymers, EUDRAGIT® polymers for modified release (e.g., one or both of EUDRAGIT RS100 and RL100, which if both present can be in any ratio), and poly(vinyl acrylate) (PVA) polymers (e.g., KOLLIDON® series).

In certain embodiments, a controlled-release layer comprises from about 15 wt % to about 35 wt % of the composition. In certain embodiments, a controlled-release layer may comprise ethyl cellulose, such as in the form of an aqueous ethyl cellulose rate-controlling polymer. A controlled-release layer may be applied in any way that provides an appropriate rate controlling membrane. For example, a powder coating may be used as a deposition vehicle for the controlled-release layer. Any suitable dispersion product may be used, such as, for example, Surelease (Colorcon, Harleysville, Pa., USA) or other products and materials known in the art.

Any desired polymer ratio, using any polymer blend, may be employed using known techniques to produce a composition having a desired release profile.

Accordingly, in certain embodiments, a controlled-release layer 108, 208 includes a polymer as described herein at about 5 wt % to about 50 wt %, or about 10 wt % to about 40 wt %, or about 20 wt % to about 30 wt %, or about 5 wt %, about 10 wt %, about 15 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, or about 40 wt %. In certain embodiments, the polymer may be an ethyl cellulose polymer. In still further embodiments, controlled-release layer 108, 208 may include a soluble component to modulate the permeability thereof. Release of a MPA active agent may be further adjusted by varying the thickness of one or more polymer layers utilized to form a controlled-release layer (i.e., by varying the weight of the polymer layer) or by adding pore forming-agents to affect the permeability of the controlled-release layer.

The controlled-release layer can be applied as a single layer. In specific embodiments, a controlled-release layer includes multiple layers, optionally (in the case of spherical, circular, round, or ovular subunits) concentrically disposed on one another. In embodiments where an active agent is disposed over at least a portion of core 102 as active layer 104, the controlled-release layer 108 can be disposed over at least a portion of the active layer 104. In embodiments where core 202 is an extruded core comprising at least a portion of the active agent, a controlled-release layer 208 is disposed over at least a portion of core 202.

In any of the embodiments described herein, a particulate subunit 100, 200 may further include a protective layer 110, 210 disposed over at least a portion of controlled-release layer 108, 208. As used herein, "protective layer" refers to a layer of material that provides protection from degradation or dissolution to an ingested composition (e.g., a particulate subunit of the present disclosure) as it travels through the stomach. In certain embodiments, the protective layer 110, 210 is selected or designed to delay release of at least a portion of the MPA active agent until the formulation reaches the a desired site within the canine, such as the lower GI tract. For example, one or more polymers of the Eudragit L series (Evonik, Essen, Del.), such as L100, may be used to form a protective layer. In certain embodiments, the protective layer comprises from about 8 wt % to about 15 wt % of the composition.

Where utilized, a protective layer 110, 210 may be a pH sensitive layer that can maintain integrity at the pH of stomach acid (e.g., roughly pH 1.2 to pH 4.5 in canines), but at least partially degrades once it reaches the small or large intestine (having a pH of about 4 to about 8 in canines). In certain embodiments, protective layer 110, 210 dissolves at a pH above about 6.0. It will be understood that the pH sensitivity of the protective layer, as well as the overall strength and release characteristics of the particulate subunit or formulation, may vary in accordance with the physiological characteristics of the canine subject to be treated (e.g., large canine versus small canine). Examples of suitable materials for forming protective layer 110, 210 include enteric polymers, such as methacrylate-based polymers including EUDRAGIT® L or EUDRAGIT® S polymers, cellulose acetate phthalate, cellulose acetate succinate, HPMC phthalate, HPMC acetate succinate, sodium alginate, zein, polyvinyl acetate phthalate (PVAP), shellac, methacrylic aid-ethyl acrylate copolymer (Kollicoat MAE), and mixtures thereof. In further embodiments, controlled-release layer 108, 208 and protective layer 110, 210 can be designed so as to provide a timed release, rather than a pH-dependent release, of the MPA active agent, so that they enable the compositions to pass through the stomach intact and release (at least a portion of) the MPA active agent in the small and/or large intestine, as desired.

In further embodiments, particulate subunits of the present disclosure may include a seal coat 106, 206. As shown in the exemplary embodiment of FIG. 1, in a particulate subunit 100, seal coat 106 separates core 102 and active agent layer 104 from controlled-release layer 108. In the exemplary embodiment represented in FIG. 2, a particulate subunit 200 includes a seal coat 206 that separates controlled-release layer 208 from core 202, which is an extruded core containing at least some (i.e., all or less than all) of the MPA active agent. In certain embodiments, a seal coat 106, 206 may be useful to separate, partially or fully, a MPA active agent from controlled-release layer 108, 208 so as to reduce or eliminate interactions and degradation of the controlled-release layer or of the active agent. However, in embodiments where a non-aqueous coating method is used to apply the active agent layer 104 to core 102, degradation may be less of a concern and seal coat 106 may therefore be excluded or reduced in thickness. Exemplary compositions for use in seal coat 106, 206 include various cellulose polymers, including hydroxypropyl methylcellulose, poly (vinyl alcohol) (Opadry AMB, Kollicoat), hydroxypropyl methylcellulose, methyl cellulose, hydroxyethylcellulose, Opadry series, and the like.

In any of the embodiments described herein, a controlled-release formulation (and/or a particulate subunit thereof) may further comprise a buffering agent or buffer to protect a MPA active agent from degradation by gastric acid. Accordingly, a buffer can be added to core 102, 202 or to active agent layer 104 surrounding core 102. In the case of extruded cores 202, the buffer may be added to core 202 or added to a layer 206, 208, 210 surrounding core 202 to provide buffering and to maintain the integrity and activity of the MPA active agent. Exemplary buffers for use in the formulations and particulate subunits described herein include, but are not limited to, phosphate buffers, citrate buffers and acetate buffers.

In any of the embodiments described herein, a particulate subunit may further comprise a buffer to affect stability or release of the MPA active agent under certain pH conditions.

Illustrative materials, amounts, ratios, and constructions of controlled-release formulations are described in the Examples, and the design and dosing of the instant controlled-release formulations will more generally be understood by persons of ordinary skill in light of this disclosure.

Kits are also provided herein that comprise a controlled-release formulation of the instant disclosure, and optionally further comprise instructions for administering the formulation to a canine subject. In certain embodiments, the kit further comprises a companion delivery piece. A companion delivery piece can be, for example, an irrigation syringe, a syringe, a tube, a transdermal patch, a mixing flask for producing a solution containing the formulation; or a food item to be provided to the veterinary subject with the formulation. In certain embodiments, a food item is of a recommended meal size for the veterinary subject. As described herein, a food item may be useful in accompanying the formulation for oral ingestion as a separate item or as a coating, filling, or mixture with the formulation. A controlled-release formulation (e.g., powder or microbeads) may also be mixed with water or another liquid so that the formulation is ingested when the canine subject takes a drink. If the subject is not drinking or resists drinking, the irrigation syringe may be useful to deliver the formulation to the subject.

In related embodiments, the kit comprises a sealed package housing individually sealed unit dosage forms comprising the formulation, e.g., MDDS, capsules, tablets, or the like, along with instructions for use and an optional companion delivery piece.

Methods of Suppressing Lymphocyte Proliferation

Controlled-release MPA formulations, including the formulations described herein, may be useful for suppressing lymphocyte proliferation and in treating diseases and conditions in which such suppression may be desired. Moreover, the present disclosure provides, for the first time, a pharmacokinetic "window" of MPA which advantageous pharmacodynamic effects are achieved in a canine subject using controlled-release formulations.

In certain aspects, a method for suppressing lymphocyte proliferation in a canine subject comprises administering to the subject a controlled-release formulation comprising a MPA active agent such that the subject achieves an average plasma [MPA] of about 250 ng/mL to about 3000 ng/mL (e.g., about 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 ng/mL) over about 8 hours following a first dose of the controlled-release formulation, whereupon at 2.5 hours, 4 hours, and 8 hours following the first dose, a percentage of proliferating lymphocytes in a whole blood sample from the subject is reduced as compared to the percentage of proliferating lymphocytes in a whole blood sample obtained from the subject 15 or fewer minutes prior to the first dose, as determined using monoclonal antibody Ki-67.

In certain embodiments, the subject achieves an average plasma [MPA] of about 350 ng/mL to about 2000 ng/mL for about 8 hours following a first dose. It will be understood that the pharmacokinetics of a controlled-release MPA formulation may depend on whether the canine subject receiving the formulation is in a fed state, or is in a fasted state, as described herein. In certain embodiments, a canine subject is administered a first dose of the controlled-release formulation when in a fed state, wherein the subject achieves an average plasma [MPA] of about 500 ng/mL to about 2500 ng/mL for about 8 hours following a first dose. In other embodiments, the canine subject is administered a first dose of the controlled-release formulation when in a fasted state, wherein the subject achieves an average plasma [MPA] of about 500 ng/mL to about 3000 ng/mL for about 8 hours following the first dose.

In certain embodiments, a fasted state may comprise a state in which the canine subject was fed no later than about 1, 2, 3, 4, 5, 6, 7, 8, 9, 10, 11, 12, 14, 16, 18, 20, 24, or more hours prior to administration, and then optionally not fed again until about 1, 2, 3, 4, 5, 6, 7, 8, 9, 10, 11, 12, 14, 16, 18, or 24 hours following administration. A fed state may comprise a state in which the canine subject has been fed immediately prior to, or no more than 1 hour prior to, administration.

In particular embodiments, the subject achieves an average plasma [MPA] of about 500 ng/mL to about 1700 ng/mL for about 8 hours following a first dose.

In particular embodiments, the subject achieves an average plasma [MPA] of about 650 ng/mL to about 1500 ng/mL for about 8 hours following a first dose.

In other embodiments, subject achieves an average plasma [MPA] of about 250 ng/mL to about 600 ng/mL for about 8 hours following a first dose.

In particular embodiments, the subject achieves a plasma [MPA] Cmax of about 2000 ng/mL over about 8 hours following a first dose, and a plasma [MPA] Cmin of no less than about 500 ng/mL from about 2.5 to about 8 hours following the first dose.

In some embodiments, the subject achieves a plasma [MPA] Cmax of about 2500 ng/mL over about 8 hours following a first dose, and a plasma [MPA] Cmin of no less than about 250 ng/mL from about 2.5 to about 8 hours following the first dose.

In certain embodiments, the subject achieves a plasma [MPA] Cmax of about 1500 ng/mL over about 8 hours following a first dose, and a plasma [MPA] Cmin of no less than about 600 ng/mL from about 2.5 to about 8 hours following the first dose.

In other embodiments, the subject achieves a plasma [MPA] Cmax of about 700 ng/mL over about 8 hours following a first dose, and a plasma [MPA] Cmin of no less than about 250 ng/mL from about 2.5 to about 8 hours following the first dose.

In still other embodiments, the subject achieves a plasma [MPA] Cmax of about 600 ng/mL from about 1 to about 8 hours following a first dose, and a plasma [MPA] Cmin of no less than about 250 ng/mL from about 2.5 to about 8 hours following the first dose.

Without wishing to be bound by theory, the presently disclosed PK profiles are believed to provide a desirable MPA PD in a canine subject administered a controlled-release formulation. In some embodiments, at 2.5 hours following a first dose, the percentage of proliferating lymphocytes in a whole blood sample from the subject is reduced by at least about 35%, 40%, 45%, 50%, 55%, 60%, 65%, 70%, 75%, 80%, or more, relative to the percentage of proliferating lymphocytes in a whole blood sample obtained from the subject 15 or fewer minutes prior to the first dose.

In certain embodiments, at 4 hours following a first dose, the percentage of proliferating lymphocytes in a whole blood sample from the subject is reduced by at least about 35%, 40%, 45%, 50%, 55%, 60%, 65%, 70%, 75%, 80%, or more, relative to the percentage of proliferating lymphocytes in a whole blood sample obtained from the subject 15 or fewer minutes prior to the first dose.

In certain embodiments, at 8 hours following a first dose, the percentage of proliferating lymphocytes in a whole blood sample from the subject is reduced by at least about 35%, 40%, 45%, 50%, 55%, 60%, 65%, 70%, 75%, 80%, or more, relative to the amount of proliferating lymphocytes in a whole blood sample obtained from the subject 15 or fewer minutes prior to the first dose.

It will be understood that the reduction in the percentage of proliferating lymphocytes may be achieved at 2.5, 4, or 8 hours following a first dose, or may be achieved at any two or all three of the indicated timepoints (i.e., at 2.5 and 4, at 2.5 and 8, at 4 and 8, or at 2.5, at 4, and at 8 hours following a first dose).

The pharmacodynamic effects achieved by the present disclosure advantageously allow for once-daily administration of a controlled-release formulation, which may in some embodiments be easier, less stressful, and more convenient for both the canine subject and the owner or care provider. For once-daily dosing, a dose may be administered at any time, though generally in the morning or evening.

Both single-day and multi-day administrations of a controlled-release MPA formulation are contemplated in the presently disclosed methods. For multi-day administrations, doses are generally administered at around the same time on each day; e.g., about 24 hours following the previous dose.

In some embodiments, administering comprises administering a single dose of the controlled-release composition per day for 2, 3, 4, 5, 6, 7, 8, 9, 10, 11, 12, 13, 14, 15, or more, consecutive days. Advantageously, and quite surprisingly, administering a once-daily dose according to the presently disclosed methods for multiple (i.e., two or more) consecutive days provides a systemic effect.

In certain embodiments, administering comprises administering a single dose for two or more consecutive days (e.g., 2, 3, 4, 5, 6, 7, 8, 9, 10, 11, 12, 13, 14, 15, or more), whereupon 24 hours after the dose of the second day, and prior to any subsequent dose, the percentage of proliferating lymphocytes in a whole blood sample from the subject is reduced by about 35%, about 40%, about 45%, about 50%, about 55%, about 60%, about 65%, about 70%, about 75%, or more, relative to the amount of proliferating lymphocytes in a whole blood sample obtained from the subject 15 or fewer minutes prior to the dose of the first day.

In further embodiments, administering is performed for 2, 3, 4, 5, 6, 7, 8, 9, 10, 11, 12, 13, 14, 15, or more days, and whereupon 24 hours after the dose of each of the second, third, fourth, fifth, sixth, seven, eighth, ninth, tenth, eleventh, twelfth, thirteenth, fourteenth, and fifteenth days, and prior to any subsequent dose, the percentage of proliferating lymphocytes in a whole blood sample from the subject is reduced by about 35%, about 40%, about 45%, about 50%, about 55%, about 60%, about 65%, about 70%, about 75%, or more, relative to the amount of proliferating lymphocytes in a whole blood sample obtained from the subject 15 or fewer minutes prior to the dose of the first day.

In some embodiments, administering comprises administering a single dose for seven or more consecutive days, whereupon 24 hours following the seventh dose, and prior to any subsequent dose, the percentage of proliferating lymphocytes in a whole blood sample from the canine subject is reduced (e.g., by any amount, including and up to at least about 35%, 40%, 45%, 50%, 55%, 60%, 65%, 70%, 75%, 80%, or more) as compared to the amount of proliferating lymphocytes in a whole blood sample obtained from the subject 15 or fewer minutes prior to the dose of the first day.

In further embodiments, administering is performed for 8, 9, 10, 11, 12, 13, 14, 15, or more days, whereupon 24 hours after the dose of each of the eighth, ninth, tenth, eleventh, twelfth, thirteenth, fourteenth, and fifteenth days, and prior to any subsequent dose, the percentage of proliferating lymphocytes in a whole blood sample from the subject is reduced by about 35%, about 40%, about 45%, about 50%, about 55%, about 60%, about 65%, about 70%, about 75%, or more, relative to the amount of proliferating lymphocytes in a whole blood sample obtained from the subject 15 or fewer minutes prior to the dose of the first day.

As illustrated in the Examples and described further herein, the presently disclosed methods are also advantageous in that a single dose of a controlled-release formulation has improved activity, both in degree and duration, over immediate-release (IR) formulations that comprise an MPA active agent (e.g., mycophenolate mofetil), including when the IR formulation is administered twice daily. In some embodiments, (i) the percentage of proliferating lymphocytes in a whole blood sample obtained from the subject at 4 hours following administration of a single dose is lower than (ii) the percentage of proliferating lymphocytes in a whole blood sample obtained from a reference canine subject that received an immediate-release formulation comprising a MPA active agent. In further embodiments, (i) the amount of proliferating lymphocytes in a whole blood sample obtained from the subject at 8 hours following administration of a single dose is lower than (ii) the amount of proliferating lymphocytes in a whole blood sample obtained from a reference canine subject that received an immediate-release formulation comprising a MPA active agent.

A "reference canine subject," as referred to herein, is a comparator canine of a similar or same age, size, gender, breed, and disease state as the canine subject receiving the controlled-release formulation. A reference canine subject receives, in one or more doses of the immediate-release formulation, a total daily intake of an MPA active agent that is present in a standard-of-care treatment such as CellCept® (Genentech) (e.g., 10 mg/kg BID; MPA dose-equivalent of approximately 7.4 mg/kg for each dose for an approximately 10 kg canine). In some embodiments, a reference canine subject receives a total daily intake of a MPA active agent that is about 40%, 45%, 50%, 55%, 60%, 65%, 70%, or up to about 100% of the amount present in the controlled-release formulation administered to the canine subject. For example, in some embodiments, a reference male beagle dog weighing approximately 12 kg may receive two daily administrations of an immediate-release formulation, each administration containing about 88.5 mg MPA and totaling about 177 mg MPA, while a male beagle dog weighing approximately 12 kg may receive a once-daily administration of a controlled-release formulation of the instant disclosure containing about 168 mg MPA or about 252 mg MPA, or any amount therebetween.

Furthermore, the disclosed methods and compositions advantageously possess improved safety profiles over immediate-release formulations. In some embodiments, administering comprises administering the dose for 10 or more days, wherein over the 10 days, the subject exhibits no adverse gastrointestinal events, wherein an adverse gastrointestinal event comprises emesis, diarrhea, soft stool, or any combination thereof. In further embodiments, administering comprises administering the dose for 15 or more days, and wherein over the 15 days, the canine subject exhibits no adverse gastrointestinal events.

In some embodiments, administering comprises administering a dose for 10 or more days, wherein over the 10 days, the subject exhibits a reduced number, a reduced severity, or both, of an adverse gastrointestinal event as compared to a reference canine subject that received an immediate-release formulation comprising a MPA active agent, wherein an adverse gastrointestinal event comprises emesis, diarrhea, soft stool, or any combination thereof.

In further embodiments, administering comprises administering a dose for 15 or more days, wherein over the 15 days, the canine subject exhibits a reduced number, a reduced severity, or both, of an adverse gastrointestinal event as compared to the reference canine subject.

In any of the embodiments described herein, administration can comprise oral administration.

In some embodiments, a method comprises use of any one or more of a controlled-release formulation as described herein, such as, for example, (i) a multiparticulate drug delivery system (MDDS) containing a plurality of particulate subunits that each comprise the MPA active agent; (ii) a tablet; (iii) a suspension; (iv) a dragee; or (v) any combination thereof. In particular embodiments, a controlled-release formulation comprises a MDDS comprising a plurality of particulate subunits each having a diameter of than about 5 mm.

In certain embodiments, a formulation comprises a MDDS that is prepared for delivery to the subject via a capsule, a sachet, a tablet, or any combination thereof. In further embodiments, each of the plurality of particulate subunits of the MDDS comprises a core, wherein: (i) the MPA active agent is contained in an active layer disposed over at least a portion of the core; or (ii) the MPA active agent is contained within the core.

In still further embodiments, each particulate subunit of the plurality further comprises a controlled-release layer, wherein the controlled-release layer is disposed over the MPA active layer of the core of (i), or is disposed over at least a portion of the core of (ii).

In yet other embodiments, each particulate subunit of the plurality comprises a seal coat layer, wherein the seal coat layer is disposed between the MPA active layer of the core of (i) and the controlled-release layer, or disposed between the core of (ii) and the controlled-release layer.

In further embodiments, each particulate subunit of the plurality further comprises a protective layer disposed over the controlled-release layer.

In any of the herein disclosed embodiments, a first dose comprises the MPA active agent at about 3 mg/kg to about 35 mg/kg.

In further embodiments, a first dose comprises the MPA active agent at about 15 mg/kg to about 30 mg/kg.

In some embodiments of the presently disclosed methods, a first dose comprises from about 3 mg to about 2200 mg of the MPA active agent.

In particular embodiments, a first dose comprises about 168 mg of the MPA active agent. In some embodiments, a first dose comprises about 252 mg of the MPA active agent. In any of the presently disclosed embodiments, the MPA active agent can comprise mycophenolate sodium. In some embodiments, the controlled-release composition is administered to the subject with food, and may in any embodiment be administered in a fed state or a fasted state.

In certain embodiments, the subject: (i) has, or is suspected of having, an autoimmune disease or disorder associated with aberrant lymphocyte proliferation; (ii) has undergone, is undergoing, or will undergo an organ transplant and/or an artificial implant; or (iii) both of (i) and (ii).

In some embodiments, the canine subject has or is suspected of having an autoimmune disease or disorder comprising atopic dermatitis, arthritis, myasthenia gravis, celiac disease, diabetes mellitus type 1, Grave's disease, inflammatory bowel disease, multiple sclerosis, psoriasis, rheumatoid arthritis, systemic lupus erythematosus, Behçet's disease, pemphigus vulgaris, refractory incomplete systemic lupus erythematosus, lupus nephritis, immunoglobulin A nephropathy, small vessel vasculitides, scleroderma (systemic sclerosis or SSc), idiopathic thrombocytopenic purpura (ITP), psoriasis, apernicious anemia, vitiligo, autoimmune hemolytic disease, glomerulonephritis, immune cytopenias, meningoencephalomyelitis, subepidermal blistering autoimmune disease, immunobullous diseases, cutaneous vasculitis, recurrent erythema multiforme, erythema nodosum, lichen planus, cutaneous Crohn's disease, sarcoidosis, hepatitis, pyoderma gangrenosum, or any combination thereof.

Treatment Methods

Also provided herein are methods for treating an autoimmune disease or disorder in a canine subject, the autoimmune disease or disorder being characterized by aberrant proliferation of lymphocytes, wherein the method comprises administering to the subject a single dose of a controlled-release composition comprising a MPA active agent, such that the subject achieves an average plasma [MPA] of about 250 ng/mL to about 3000 ng/ml (e.g., about 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 ng/mL) over about 8 hours following the single dose, and whereupon at 2.5 hours, 4 hours, and 8 hours following the single dose, the percentage of proliferating lymphocytes in a whole blood sample from the subject is reduced by at least about 35%, 40%, 45%, 50%, 55%, 60%, 65%, 70%, 75%, 80%, or more, as compared to the percentage of proliferating lymphocytes in a whole blood sample obtained from the subject 15 or fewer minutes prior to the single dose, as determined using monoclonal antibody Ki-67.

In some embodiments, the subject achieves an average plasma [MPA] of about 250 ng/mL to about 2500 ng/mL for about 8 hours following a first dose.

In some embodiments, the subject achieves an average plasma [MPA] of about 350 ng/mL to about 2000 ng/mL for about 8 hours following a first dose.

In further embodiments, the subject achieves an average plasma [MPA] of about 500 ng/mL to about 1700 ng/mL for about 8 hours following a first dose.

In still further embodiments, the subject achieves an average plasma [MPA] of about 650 ng/mL to about 1500 ng/mL for about 8 hours following a first dose.

In some embodiments, the subject achieves a plasma [MPA] Cmax of about 2500 ng/mL over about 8 hours following a first dose, and a plasma [MPA] Cmin of no less than about 250 ng/mL from about 2.5 to about 8 hours following a first dose.

In further embodiments, the subject achieves a plasma [MPA] Cmax of about 2000 ng/mL over about 8 hours following a single dose, and a plasma [MPA] Cmin of no less than about 500 ng/mL from about 2.5 to about 8 hours following the single dose.

In further embodiments, the subject achieves a plasma [MPA] Cmax of about 1500 ng/mL over about 8 hours following a single dose, and a plasma [MPA] Cmin of no less than about 600 ng/mL from about 2.5 to about 8 hours following the single dose.

In other embodiments, the subject achieves a plasma [MPA] Cmax of about 700 ng/mL over about 8 hours following a single dose, and a plasma [MPA] Cmin of no less than about 250 ng/mL from about 2.5 to about 8 hours following the single dose.

In further embodiments, the subject achieves a plasma [MPA] Cmax of about 600 ng/mL from about 1 to about 8 hours following the first dose, and a plasma [MPA] Cmin of no less than about 250 ng/mL from about 2.5 to about 8 hours following the first dose.

In some embodiments, the administering comprises administering a single dose for 2, 3, 4, 5, 6, 7, 8, 9, 10, 11, 12, 13, 14, 15, or more, consecutive days.

In certain embodiments, administering comprises administering a single dose for two or more consecutive days (e.g., 2, 3, 4, 5, 6, 7, 8, 9, 10, 11, 12, 13, 14, 15, or more), whereupon 24 hours after the dose of the second day, and prior to any subsequent dose, the percentage of proliferating lymphocytes in a whole blood sample from the subject is reduced by about 35%, about 40%, about 45%, about 50%, about 55%, about 60%, about 65%, about 70%, about 75%, or more, relative to the amount of proliferating lymphocytes in a whole blood sample obtained from the subject 15 or fewer minutes prior to the dose of the first day.

In further embodiments, the administering is performed for 2, 3, 4, 5, 6, 7, 8, 9, 10, 11, 12, 13, 14, 15, or more days, and whereupon 24 hours after the dose of each of the second, third, fourth, fifth, sixth, seven, eighth, ninth, tenth, eleventh, twelfth, thirteenth, fourteenth, and fifteenth days, and prior to any subsequent dose, the percentage of proliferating lymphocytes in a whole blood sample from the subject is reduced by about 35%, about 40%, about 45%, about 50%, about 55%, about 60%, about 65%, about 70%, about 75%, or more, relative to the amount of proliferating lymphocytes in a whole blood sample obtained from the subject 15 or fewer minutes prior to the dose of the first day.

In further embodiments, the administering comprises administering a single dose for seven or more consecutive days, whereupon 24 hours after the dose of the seventh day, and prior to any subsequent dose, the percentage of proliferating lymphocytes in a whole blood sample from the subject is reduced by about 35%, about 40%, about 45%, about 50%, about 55%, about 60%, about 65%, about 70%, about 75%, or more, relative to the amount of proliferating lymphocytes in a whole blood sample obtained from the subject 15 or fewer minutes prior to the dose of the first day.

In some embodiments, the administering comprises administering a single dose for 10 or more days, wherein over the 10 days, the subject exhibits no adverse gastrointestinal events, wherein an adverse gastrointestinal event comprises emesis, diarrhea, soft stool, or any combination thereof.

In particular embodiments, the autoimmune disease or disorder comprises atopic dermatitis, arthritis, myasthenia gravis, celiac disease, diabetes mellitus type 1, Grave's disease, inflammatory bowel disease, multiple sclerosis, psoriasis, rheumatoid arthritis, systemic lupus erythematosus, Behçet's disease, pemphigus vulgaris, refractory incomplete systemic lupus erythematosus, lupus nephritis, immunoglobulin A nephropathy, small vessel vasculitides, scleroderma (systemic sclerosis or SSc), idiopathic thrombocytopenic purpura (ITP), psoriasis, apernicious anemia, vitiligo, autoimmune hemolytic disease, glomerulonephritis, immune cytopenias, meningoencephalomyelitis, subepidermal blistering autoimmune disease, immunobullous diseases, cutaneous vasculitis, recurrent erythema multiforme, erythema nodosum, lichen planus, cutaneous Crohn's disease, sarcoidosis, hepatitis, pyoderma gangrenosum, or any combination thereof.

In another aspect, methods are provided for providing a MPA active agent to a canine subject in relation to an organ transplant or artificial implant procedure to, for example, suppress or treat an immune response against the transplanted organ and/or artificial implant. In some embodiments, a method comprises administering to a canine subject that has undergone, is undergoing, or will undergo an organ transplant and/or artificial implant, a controlled-release composition comprising a MPA active agent, at a dose of about 3 mg/kg to about 35 mg/kg of the MPA active agent, wherein the subject receives a single dose of the controlled-release composition per day, such that the subject achieves a plasma [MPA] Cmax of about 3000 ng/mL over about 8 hours following a single dose, and a plasma [MPA] Cmin of no less than about 250 ng/mL from about 2.5 to about 8 hours following the single dose, and the subject achieves an average plasma [MPA] of 250 ng/mL to about 2500 ng/ml for about 8 hours following the single dose, and at 2.5 hours, 4 hours, and 8 hours following the single dose, the percentage of proliferating lymphocytes in a whole blood sample from the subject is reduced by at least about 35%, 40%, 45%, 50%, 55%, 60%, 65%, 70%, 75%, 80%, or more, as compared to the percentage of proliferating lymphocytes in a whole blood sample obtained from the subject 15 or fewer minutes prior to the single dose, as determined using monoclonal antibody Ki-67.

In some embodiments, the subject achieves a plasma [MPA] Cmax of about 2500 ng/mL over about 8 hours following the first dose, and a plasma [MPA] Cmin of no less than about 250 ng/mL from about 2.5 to about 8 hours following the single dose.

In some embodiments, the subject achieves a plasma [MPA] Cmax of about 2000 ng/mL over about 8 hours following the single dose, and a plasma [MPA] Cmin of no less than about 500 ng/mL from about 2.5 to about 8 hours following the single dose.

In certain embodiments, the subject achieves a plasma [MPA] Cmax of about 1500 ng/mL over about 8 hours following the single dose, and a plasma [MPA] Cmin of no less than about 600 ng/mL from about 2.5 to about 8 hours following the single dose.

In particular embodiments, the subject achieves a plasma [MPA] Cmax of about 700 ng/mL over about 8 hours following the single dose, and a plasma [MPA] Cmin of no less than about 250 ng/mL from about 1 to about 8 hours following the single dose.

In some embodiments, the administering comprises administering the dose for 2, 3, 4, 5, 6, 7, 8, 9, 10, 11, 12, 13, 14, 15, or more, consecutive days.

In certain embodiments, the administering comprises administering the single dose for seven or more consecutive days, whereupon 24 hours after the dose of the seventh day, and prior to any subsequent dose, the percentage of proliferating lymphocytes in a whole blood sample from the canine subject is reduced by about 35%, about 40%, about 45%, about 50%, about 55%, about 60%, about 65%, about 70%, about 75%, or more, relative to the amount of proliferating lymphocytes in a whole blood sample obtained from the subject 15 or fewer minutes prior to the dose of the first day.

In further embodiments, the administering comprises administering the dose for 10 or more days, wherein over the 10 days, the subject exhibits no adverse gastrointestinal events, wherein an adverse gastrointestinal event comprises emesis, diarrhea, soft stool, or any combination thereof.

In some embodiments, following the administration, the canine subject exhibits a reduction in the severity of a symptom associated with the autoimmune disease or disorder. Such symptoms include, for example, rash, elevated levels of autoantibodies and/or inflammatory cytokine levels, fever, fatigue, stiffness, pain, blisters, itchiness, discharge, eczema, swelling, hair loss, loss of appetite, asthma, and foul odor.

Uses

In another aspect, the present disclosure provides uses of a controlled-release MPA formulation for suppressing lymphocyte proliferation and/or activation in a canine subject.

In some embodiments, a use comprises administering to the subject a controlled-release formulation comprising a mycophenolic acid (MPA) active agent such that the subject achieves an average plasma [MPA] of about 250 ng/mL to about 3000 ng/mL (e.g., about 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 ng/mL) over about 8 hours following a first dose of the controlled-release formulation,
wherein the subject achieves a plasma [MPA] Cmax of about 3000 ng/mL, optionally about 2500 ng/mL, optionally about 2000 ng/mL, optionally about 1500 mL, optionally about 700 ng/mL, optionally about 600 ng/mL, optionally about 500 ng/mL, over about 8 hours following the first dose, and a plasma [MPA] Cmin of no less than about 250 ng/mL from about 2.5 to about 8 hours following the first dose, whereupon at 2.5 hours, 4 hours, and 8 hours following the first dose, a percentage of proliferating lymphocytes in a whole blood sample from the subject is reduced as compared to the percentage of proliferating lymphocytes in a whole blood sample obtained from the subject 15 or fewer minutes prior to the first dose, as determined using monoclonal antibody Ki-67.

In further embodiments, the subject achieves an average of plasma [MPA] of: (i) about 350 ng/ml to about 2000 ng/mL over 8 hours following the first dose; (ii) about 500 ng/ml to about 1700 ng/mL over 8 hours following the first dose; or (iii) about 650 ng/ml to about 1500 ng/mL over 8 hours following the first dose.

In accordance with any of the herein-described embodiments, at 2.5 hours, preferably at 4 hours, more preferably at 8 hours following the first dose, the percentage of proliferating lymphocytes in a whole blood sample from the subject is reduced by at least about 35%, 40%, 45%, 50%, 55%, 60%, 65%, 70%, 75%, 80%, or more, relative to the percentage of proliferating lymphocytes in a whole blood sample obtained from the subject 15 or fewer minutes prior to the first dose.

In accordance with any of the herein-described embodiments, the subject is administered the composition for 2, 3, 4, 5, 6, 7, 8, 9, 10, 11, 12, 13, 14, 15, or more, consecutive days.

In further embodiments, the subject receives a single dose of the controlled-release composition per day.

In still further embodiments, the administering comprises administering the single dose for 2, 3, 4, 5, 6, 7, 8, 9, 10, 11, 12, 13, 14, 15, or more days, and whereupon 24 hours after the dose of each of the second, third, fourth, fifth, sixth, seventh, eighth, ninth, tenth, eleventh, twelfth, thirteenth, fourteenth, or fifteenth days, and prior to any subsequent dose, the percentage of proliferating lymphocytes in a whole blood sample from the subject is reduced by about 35%, about 40%, about 45%, about 50%, about 55%, about 60%, about 65%, about 70%, about 75%, or more, relative to the amount of proliferating lymphocytes in a whole blood sample obtained from the subject 15 or fewer minutes prior to the dose of the first day. In particular embodiments, the administering comprises administering the single dose for 7 or more consecutive days, whereupon after the dose of the seventh day, the percentage of proliferating lymphocytes in a whole blood sample from the subject is reduced by about 35%, about 40%, about 45%, about 50%, about 55%, about 60%, about 65%, about 70%, about 75%, or more, relative to the amount of proliferating lymphocytes in a whole blood sample obtained from the subject 15 or fewer minutes prior to the dose of the first day.

In accordance with any of the herein-described embodiments, (i) the percentage of proliferating lymphocytes in a whole blood sample obtained from the subject at 4 hours, optionally at 8 hours, following administration of a first dose is lower than (ii) the percentage of proliferating lymphocytes in a whole blood sample obtained from a reference canine subject (i.e., a reference canine subject as described herein) that was administered an immediate-release formulation comprising a MPA active agent.

In accordance with any of the herein-described embodiments, the administering comprises administering the single dose for 10 or more days, wherein over the 10 days, the subject exhibits no adverse gastrointestinal events, wherein an adverse gastrointestinal event comprises emesis, diarrhea, soft stool, or any combination thereof.

In further embodiments, the administering comprises administering the single dose for 15 or more days, wherein over the 15 days, the subject exhibits no adverse gastrointestinal events, wherein an adverse gastrointestinal event comprises emesis, diarrhea, soft stool, or any combination thereof.

In further embodiments, the administering comprises administering the single dose for 10 or more days, wherein over the 10 days, the subject exhibits a reduced number, a reduced severity, or both, of an adverse gastrointestinal event as compared to a reference canine subject (i.e., a reference canine subject as described herein) that was administered an immediate-release formulation comprising a MPA active agent, wherein an adverse gastrointestinal event comprises emesis, diarrhea, soft stool, or any combination thereof.

In further embodiments, the immediate-release formulation was administered to the reference canine subject at a twice-daily dose of 7.4 mg/kg MPA, wherein the immediate-release formulation optionally comprises mycophenolate mofetil.

In accordance with any of the herein-described embodiments, the MPA active agent comprises mycophenolate sodium, wherein the mycophenolate sodium is optionally administered to the canine subject orally.

In further embodiments, the controlled-release composition comprises a Tillable capsule comprising a plurality of particulate subunits that each comprise: (i) a core, wherein (a) the MPA active agent is comprised in an active layer disposed over at least a portion of the core; or (b) the MPA active agent is disposed within the core; (ii) a controlled-release layer disposed over at least a portion of (a) the active layer or (b) the core; (iii) an optional seal coat layer disposed between (a) the active layer and the controlled-release layer, or (b) the core and the controlled-release layer; (iv) an optional protective layer disposed over the controlled-release layer, wherein the MPA active agent comprises mycophenolate sodium and is optionally present in the controlled-release composition from about 3 mg to about 2.2 g (i.e., about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 81, 82, 84, 85, 86, 87, 88, 89, 90, 91, 92, 93, 94, 95, 96, 97, 98, 99, 100, 105, 110, 115, 120, 125, 130, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1100, 1200, 1300, 1400, 1500, 1600, 1700, 1800, 1900, 2000, 2100, or 2200 mg).

In accordance with any of the herein-described embodiments, the canine: (i) has, or is suspected of having, an autoimmune disease or disorder associated with aberrant lymphocyte proliferation and/or activation, wherein the autoimmune disease or disorder optionally comprises atopic dermatitis, arthritis, myasthenia gravis, celiac disease, diabetes mellitus type 1, Grave's disease, inflammatory bowel disease, multiple sclerosis, psoriasis, rheumatoid arthritis, systemic lupus erythematosus, Behçet's disease, pemphigus vulgaris, refractory incomplete systemic lupus erythematosus, lupus nephritis, immunoglobulin A nephropathy, small vessel vasculitides, scleroderma (systemic sclerosis or SSc), idiopathic thrombocytopenic purpura (ITP), psoriasis, apernicious anemia, vitiligo, autoimmune hemolytic disease, glomerulonephritis, immune cytopenias, meningoencephalomyelitis, subepidermal blistering autoimmune disease, immunobullous diseases, cutaneous vasculitis, recurrent erythema multiforme, erythema nodosum, lichen planus, cutaneous Crohn's disease, sarcoidosis, hepatitis, pyoderma gangrenosum, or any combination thereof; (ii) has undergone, is undergoing, or will undergo an organ transplant and/or an artificial implant; or (iii) both of (i) and (ii).

In some embodiments, following the administration, the veterinary subject exhibits a reduction in the severity of a symptom associated with the autoimmune disease or disorder, wherein the symptom is not aberrant lymphocyte proliferation. Such symptoms include, for example, rash, elevated levels of autoantibodies and/or inflammatory cytokine levels, fever, fatigue, stiffness, pain, blisters, itchiness, discharge, eczema, swelling, hair loss, loss of appetite, asthma, and foul odor.

Also provided herein are methods of preparing a medicament for suppressing lymphocyte proliferation and/or activation in a canine, the method comprising preparing a controlled-release formulation comprising a mycophenolic acid (MPA) active agent such that the subject maintains an average plasma [MPA] of from about 250 ng/mL to about 3000 ng/mL for about 8 hours following a first dose of the controlled-release formulation, such the subject achieves a plasma [MPA] Cmax of about 3000 ng/mL, optionally about 2500 ng/mL, optionally about 2000 ng/mL, optionally about 1500 ng/mL, optionally about 700 ng/mL, optionally about 600 ng/mL, optionally about 500 ng/mL, over about 8 hours following the first dose, and a plasma [MPA] Cmin of no less than about 250 ng/ml from about 1 to about 8 hours following the first dose, and such that at 2.5 hours, 4 hours, and 8 hours following the first dose, the percentage of proliferating lymphocytes in a whole blood sample from the subject is reduced as compared to the percentage of proliferating lymphocytes in a whole blood sample obtained from the subject 15 or fewer minutes prior to the first dose, as determined using monoclonal antibody Ki-67.

Dosing and Administration

It will be understood that a variety of dosages of a controlled-release formulation of the present disclosure (and of a MPA active agent contained therein) may be administered to a veterinary subject in accordance with, e.g., the physiological characteristics of the veterinary subject (e.g., size, GI length, digestive rate, digestive pH, stomach crushing strength), the state of health of the veterinary subject (e.g., the urgency of the need for treatment and of what strength) and other factors. For example, in certain embodiments, a dosing regime or schedule comprises a single administration of a single dose of a controlled-release formulation as described herein). In certain embodiments, a dosage regime or schedule comprises multiple administrations of a single dose over the course of, e.g., a day. Alternatively, a dosage regime or schedule may comprise single or multiple administrations of multiple doses of a controlled-release formulation. In embodiments comprising multiple doses, the doses may be administered simultaneously, contemporaneously, or sequentially.

An appropriate dose will be determined according to any one or more of a variety of factors typically considered when determining an appropriate drug dose; e.g., the size, age, species, gender, and general health of a subject receiving the dose; the type, severity, and stage of a disease condition; known PK parameters of the drug, such as absorption, in vivo half-life, and the like). Table 1 provides non-limiting examples of dosages of a formulation of the present disclosure for canine subjects ranging in size from 2 to 80 kilograms; it will be understood that for subjects larger than 80 kilograms, or smaller than 2 kilograms, or in between the shown sizes, and/or of non-canine species, dosages may be adjusted accordingly.

TABLE 1

Exemplary Dosages of a Controlled-Release Formulation

| Size (kg) | Dosage (mg/kg) | | | | | | |
|---|---|---|---|---|---|---|---|
| | 10 | 15 | 20 | 25 | 30 | 35 | 40 |
| 2 | 20 | 30 | 40 | 50 | 60 | 70 | 80 |
| 5 | 50 | 75 | 100 | 125 | 150 | 175 | 200 |
| 10 | 100 | 150 | 200 | 250 | 300 | 350 | 400 |
| 20 | 200 | 300 | 400 | 500 | 600 | 700 | 800 |
| 40 | 400 | 600 | 800 | 1000 | 1200 | 1400 | 1600 |
| 60 | 600 | 900 | 1200 | 1500 | 1800 | 2100 | 2400 |
| 80 | 800 | 1200 | 1600 | 2000 | 2400 | 2800 | 3200 |

EXAMPLES

Example 1

Preparation and Testing of Certain Mycophenolate Controlled-Release Veterinary Compositions According to the Present Disclosure Preparation of Active Agent-Coated Beads:
Materials
Sugar spheres (#25/30; COLORCON®, Harleysville, Pa.)
OPADRY® Clear, hydroxypropyl methylcellulose-based coating (COLORCON®, Harleysville, Pa.)
Purified Water
Sodium Mycophenolate
Equipment
Mechanical stirrer
Fluid bed coater
Hot air oven

TABLE 2

Composition of drug coating solution

| Component | Batch formula (g) |
|---|---|
| OPADRY ® Clear | 25 |
| Purified Water | 475 |
| Sodium Mycophenolate | 240 |

1. OPADRY® Clear was dispersed in purified water and stirred until a clear solution was obtained.
2. Mycophenolate sodium was added to the solution and stirred for 1 hour.
3. 500 g of sugar beads as loaded into the fluid bed chamber.
4. The bed was fluidized, sugar beads were warmed and the coating solution prepared as described in Table 2 was sprayed onto the fluidized beads.
5. Coating was continued with periodic drying and weighing of the coated beads.
6. Coating was continued until the beads had gained approximately 40% in weight.
7. Beads were dried overnight (15 hours) at 40° C. in a hot air oven Exemplary Preparation of Extruded Beads with Active Agent:
Materials
Drug Substance: Sodium mycophenolate: 50 to 90%
Extrusion/Spheronization Aid: Microcrystalline Cellulose: 15 to 20%
Binders: Hydroxypropyl cellulose or hydroxyl propyl methyl cellulose or Pregelatinized Starch or Ethyl Cellulose or poly(vinyl pyrrolidone) (2 to 5%)
Modified release excipients: HPMC, HPC, acrylic polymers, HEC, EC—these can be incorporated into the beads or applied as coating
Other fillers: lactose, maltodextrin, mannitol, sorbitol, dicalcium phosphate/(as needed)
Superdisintegrants: crosslinked PVP, sodium starch glycolate, sodium croscarmellose (% as needed)
Manufacturing
The drug substance was mixed with microcrystalline cellulose, binder, and disintegrant in a planetary mixer or a high shear mixer for 10 minutes;
The required amount of water was added to the mixer and mixing continued for another 5 to 10 minutes;
The resulting wet mass was passed through an extruder to obtain an extrudate (example equipment: Caleva, LCI, Glatt etc.);
The extrudate was then spheronized on a spheronizer fitted with a crosshatch plate to form spheronized beads (example equipment: Caleva, LCI, Glatt)
The spheronized beads were then dried in a fluid bed dryer till the desired moisture content (<1%) was reached;
The dried beads were then passed through screens to remove fine beads (<500 µm) and coarse beads (>2500 µm);
The dried beads were then loaded into a fluid bed coater and coated with an appropriate amount of a rate-controlling polymer (15 to 30% range);
Additional enteric coating (optional) was then applied to the coated beads;
The beads were then dried after all coating steps were completed.
Preparation of Seal Coated Beads:
Materials
Drug coated or extruded beads (from above sections)
OPADRY® Clear
Talc Purified Water
Equipment
Mechanical stirrer
Fluid bed coater
Hot air oven
1. OPADRY Clear was dispersed in purified water and stirred to obtain a clear solution.
2. Talc was dispersed into the OPADRY® solution and stirred to obtain a smooth dispersion.
3. About 300 g of the drug coated beads (from above) was loaded into the fluid bed coater.
4. The bed was fluidized, drug coated beads were warmed, and the coating solution prepared as described in Table 3 was sprayed onto the fluidized beads.
5. Coating was continued with periodic drying and weighing of the coated beads.
6. Coating was continued until the beads had gained approximately 8 to 10% in weight.
7. Beads were dried overnight (15 hours) at 40° C. in a hot air oven.

TABLE 3

Composition of seal coat solution

| Component | Batch formula (g) |
| --- | --- |
| OPADRY ® Clear | 10 |
| Talc | 20 |
| Purified water | 170 |

Preparation of Controlled-Release Layers:
SURELEASE Coating—Option 1
Materials
Seal Coated beads (from above)
SURELEASE® E-7 19040, aqueous ethylcellulose rate controlling polymer (COLORCON®, Harleysville, Pa.) (Other grades of SURELEASE® can be used if desired)
Equipment
Mechanical stirrer
Fluid bed coater
Hot air oven

TABLE 4

Composition of SURELEASE ® Coating solution

| Component | Batch formula (g) |
| --- | --- |
| SURELEASE ® E7 19040 | 240 |
| Purified water | 170 |

1. SURELEASE® was dispersed in purified water and stirred to obtain a smooth dispersion.
2. About 300 g of the seal coated beads was loaded into the fluid bed coater.
3. The bed was fluidized, the seal coated beads were warmed, and the coating solution prepared as described in Table 4 was sprayed onto the fluidized beads.
4. Coating was continued with periodic drying and weighing of the coated beads.
5. Coating was continued until the beads had gained desired coating weight.
6. Coated bead samples were withdrawn at desired weight gain (e.g.: 15%, 22%, 30%).
7. At the end of the coating, beads were dried overnight in the oven at 60° C./75% relative humidity conditions.

EUDRAGIT Coating—Option 2
Materials
Seal Coated beads (from above)
EUDRAGIT® RS (acrylic controlled-release polymer either as powder or premade dispersion—RS 30D)
EUDRAGIT® RL (acrylic controlled-release polymer either as powder or premade dispersion—RL 30D)
Talc
Triethyl citrate (TEC)
Equipment
Mechanical stirrer
Fluid bed coater
Hot air oven

TABLE 5

Sample composition for EUDRAGIT ® coating

| Component | Batch formula (g) |
| --- | --- |
| EUDRAGIT ® RL 30D (1 part)* | 39.3 |
| EUDRAGIT ® RS 30D (9 parts)* | 352.9 |
| TEC | 23.5 |
| Talc | 58.8 |
| Purified Water | 525.5 |

*This composition will be referred as EUDRAGIT ® RS (90): RL (10) or EUDRAGIT ® RS/RL: 90/10. This ratio can be altered in any composition, increasing amount of RS 100 will reduce membrane permeability with decrease in release rate from bead.

1. Talc and TEC were dispersed in purified water and homogenized until a smooth dispersion is obtained.
2. The dispersion from Step (1) was mixed until a uniform dispersion was obtained.
3. The dispersion was filtered through 80 mesh sieve to remove any coarse particles.
4. About 300 g of seal coated beads was loaded into the fluid bed coater.
5. The bed was fluidized, seal coated beads were warmed and the coating solution prepared as described in Table 4 was sprayed onto the fluidized beads.
6. Coating was continued with periodic drying and weighing of the coated beads until the desired weight gain was obtained (typically 15% to 30%).
7. Coated beads were dried overnight (15 hours) at 40° C. in a hot air oven.

E.R. Coating—Option 3
Materials
Ethylcellulose 10
Klucel EF (HPC)
Talc
Dibutyl sebacate
DI water
Ethanol
Equipment
Mechanical stirrer
Fluid bed coater
Hot air oven
Sprayer

TABLE 6

Sample composition for 30 wt % gain

| Component | Wt % |
| --- | --- |
| Ethylcellulose 10 | 4.15 |
| Klucel EF (HPC) | 0.46 |
| Talc | 0.92 |
| Dibutyl Sebacate | 0.46 |
| DI water | 9.40 |
| Ethanol 190 pf | 84.61 |

1. Dibutyl sebacate was dissolved in a mixture of ethanol and deionized water.
2. The required quantity of HPC was dispersed in the hydroalcoholic mixture and stirred to obtain a solution.
3. The required quantity of ethylcellulose was dispersed in the above mixture and stirred until a solution was obtained
4. Talc was dispersed in the above solution and stirred to obtain a smooth dispersion.
5. The drug coated beads were loaded into the fluid bed coater
6. The bed was fluidized, beads were warmed, and the coating solution prepared as described in step 4 was sprayed onto the fluidized beads.
7. Coating was continued with periodic drying and weighing of the coated beads 8. Coating was continued until the beads had gained desired coating weight.

9. Coated bead samples were withdrawn at desired weight gain (e.g., 15%, 22%, or 30%)

Preparation of Protective Layer:

Materials

Control release layer coated beads (from above)

EUDRAGIT® L30 D 55 (other grades of EUDRAGIT® polymers, or

OPADRY® polymers that confer enteric protection can also be used)

Triethyl citrate (TEC)

Talc

Equipment

Mechanical stirrer

Fluid bed coater

Hot air oven

TABLE 7

Composition of Enteric Coating solution

| Component | Batch formula (g) |
|---|---|
| EUDRAGIT ® L30D 55 | 83.3 |
| TEC | 2.5 |
| Talc | 12.5 |
| Purified Water | 101.6 |

1. Talc and TEC were dispersed in purified water and homogenized until a smooth dispersion was obtained.

2. The dispersion from Step (1) was dispersed into EUDRAGIT® L30D 55 suspension and mix until a uniform dispersion was obtained.

3. The dispersion was filtered through 80 mesh sieve to remove any coarse particles.

4. About 300 g SURELEASE® coated beads was loaded into the fluid bed coater; alternatively, about 300 g of EUDRAGIT® coated beads from above may be used.

5. The bed was fluidized, controlled-release coated beads were warmed and the coating solution prepared as described in Table 7 is sprayed onto the fluidized beads.

6. Coating was continued with periodic drying and weighing of the coated beads until the desired weight gain of EUDRAGIT® L 30 D55 was obtained (typically 8 to 15%).

7. Coated beads were dried overnight (15 hours) at 40° C. in a hot air oven.

Determination of Release Rate

Release rate determinations were performed on beads obtained after coating with controlled-release layer(s) and optionally a protective layer. Release rate determinations were conducted as follows:

Dissolution Apparatus: USP Type 1

Dissolution Media Volume and Speed: 900 mL at 100 rpm

A known quantity of beads were weighed (based on assay of coated beads) and placed in the USP Type 1 basket apparatus. For a biphasic dissolution profile (biphasic media), beads were exposed to pH 1.2 media for 2 hours. After 2 hours, the basket was moved to buffer media at pH 6.8 and dissolution was continued for an additional 10 hours, 12 hours, 14 hours or 24 hours, as desired. Aliquots were withdrawn at periodic intervals and analyzed for mycophenolate sodium using a UV detection method. Data from representative experiments are shown in FIGS. 6-9 and Table 8, below.

Figure 4:
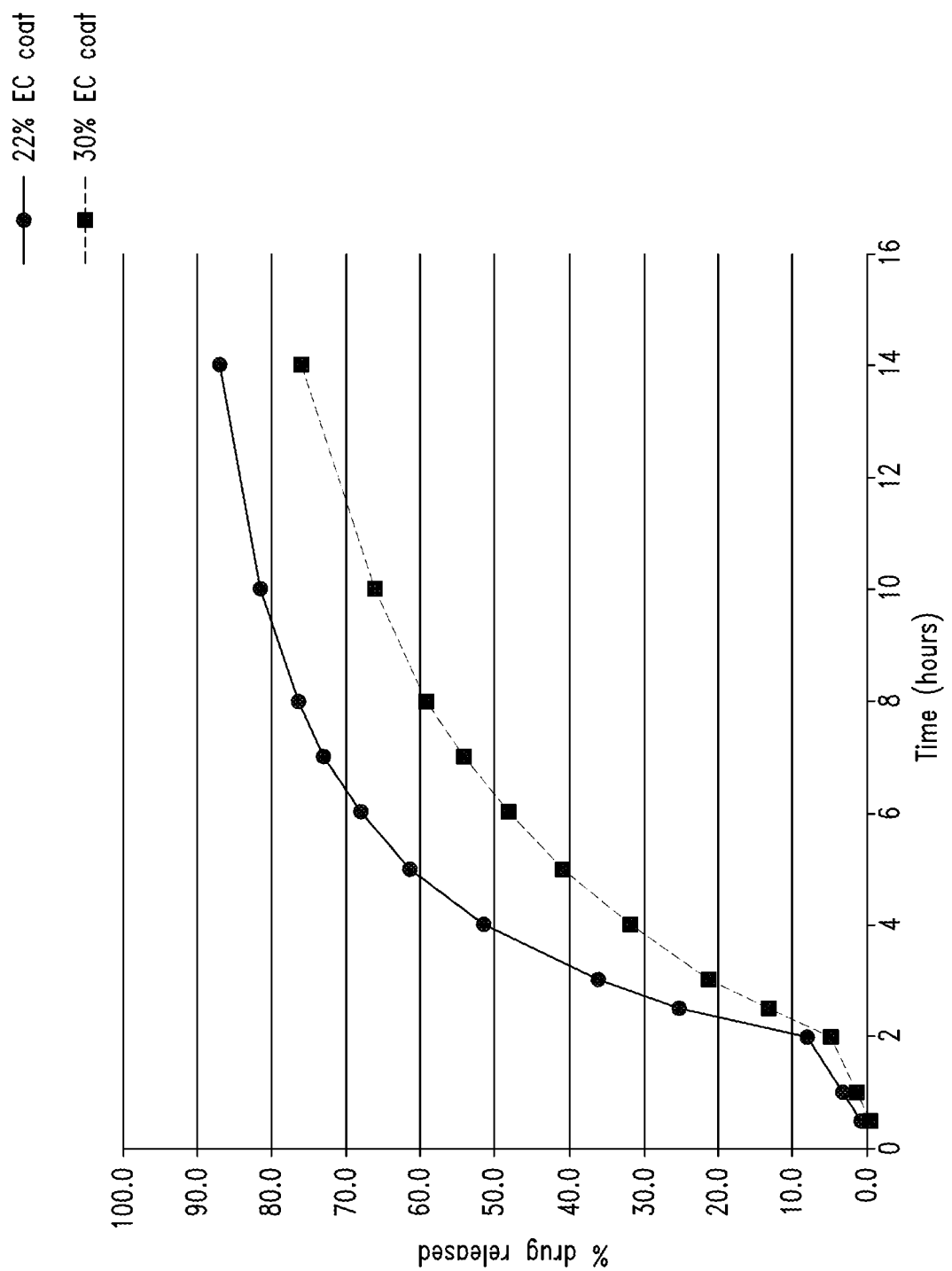
FIG. 4 shows the release of mycophenolate sodium in biphasic media (pH 1.2 for 2 hours, followed by incubation at pH 6.8) from two embodiments of a particulate subunit in accordance with the present disclosure.

FIG. 4 shows the release of sodium mycophenolate from controlled-release beads in biphasic media as noted above. The bead construct is sugar sphere/drug layer/HPMC seal coat/ethyl cellulose (SURELEASE®). The data was generated for beads with only a controlled-release layer. A protective layer was not included. As shown, release from beads coated with a 22% by weight ethyl cellulose controlled-release layer was higher than that for beads coated with a 30% by weight ethyl cellulose layer. Both compositions maintained their integrity at pH 1.2 (0-2 hours), with rapid release upon transitioning to pH 6.8 (>2 hours).

Figure 5:
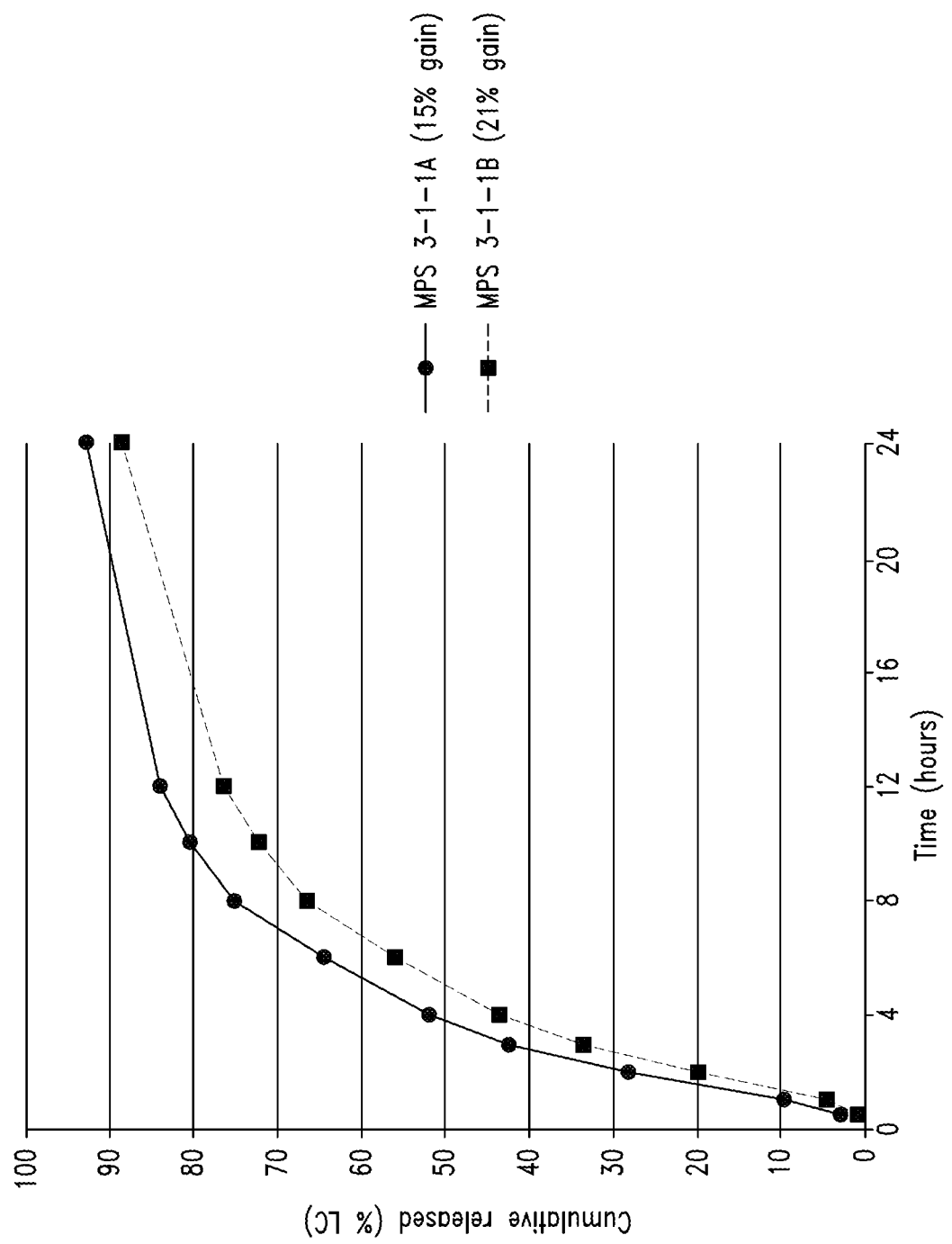
FIG. 5 shows the release of mycophenolate sodium from additional embodiments of a particulate subunit of a controlled-release formulation in accordance with the present description. Release was measured during incubation in media at pH 6.8.

FIG. 5 shows the release of sodium mycophenolate from controlled-release beads in pH 6.8 media. The bead construct is sugar sphere/drug layer/HPMC seal coat/acrylic polymer (EUIDRAGIT® RS 100). A protective layer was not included.

Figure 6:
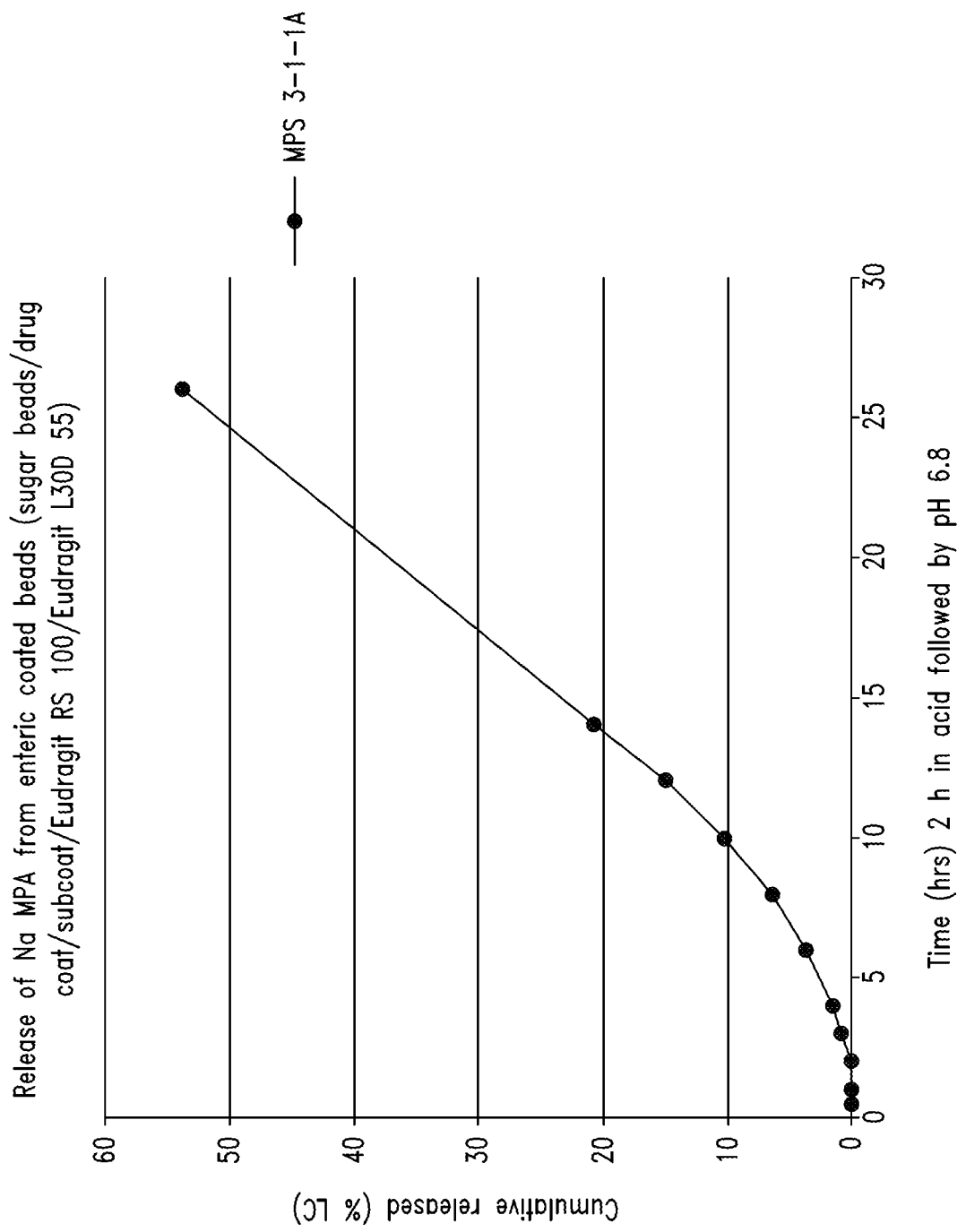
FIG. 6 shows the release of mycophenolate sodium from yet another embodiment of a particulate subunit in accordance with the present disclosure, where the particulate subunit was exposed to a 2-hour incubation in acidic media (pH 1.2), followed by pH 6.8 media.

FIG. 6 shows the release of sodium mycophenolate from controlled-release beads in biphasic media, as described above. The bead construct is sugar sphere/drug layer/HMPC seal coat/EUDRAGIT® RS 100/EUDRAGIT® L30D 55. The EUDRAGIT® RS 100 layer provides the controlled-release characteristics, while the EUDRAGIT® L30D 55 provides the protective, enteric coating. As noted, little to no release occurred at pH 1.2 (0-2 hours), with release occurring once the pH was raised to 6.8 (>2 hours).

Figure 7:
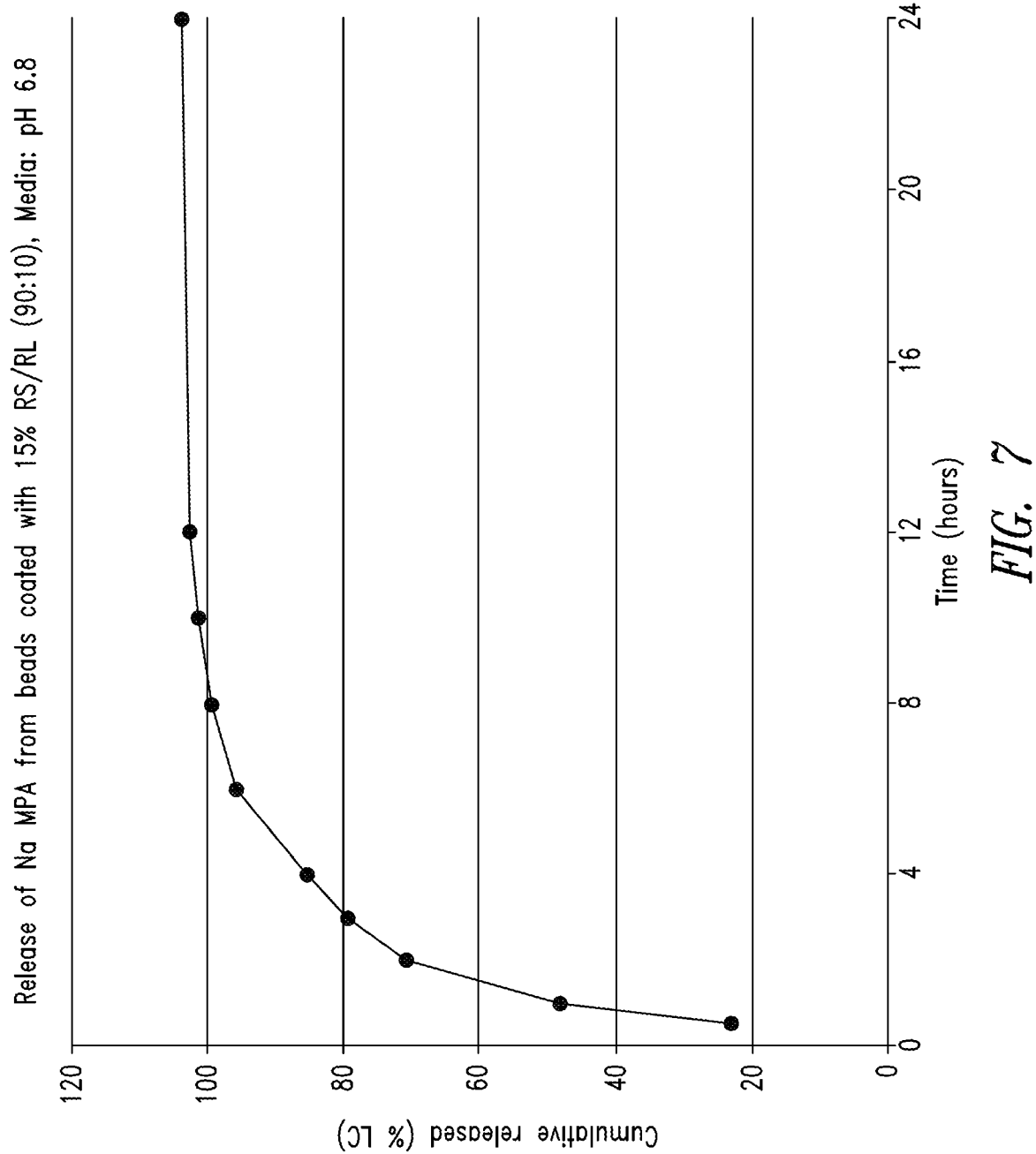
FIG. 7 shows release of mycophenolate sodium from another embodiment of a particulate subunit in accordance with the present disclosure.

FIG. 7 shows the release of sodium mycophenolate from controlled-release beads in pH 6.8 media. The bead construct is sugar sphere/drug layer/EUIDRAGIT® RS 100: EUDRAGIT® RL 100 (90:10). A seal coat and a protective layer were not included. Rapid release is noted occurring around hours 2-6.

Figure 8:
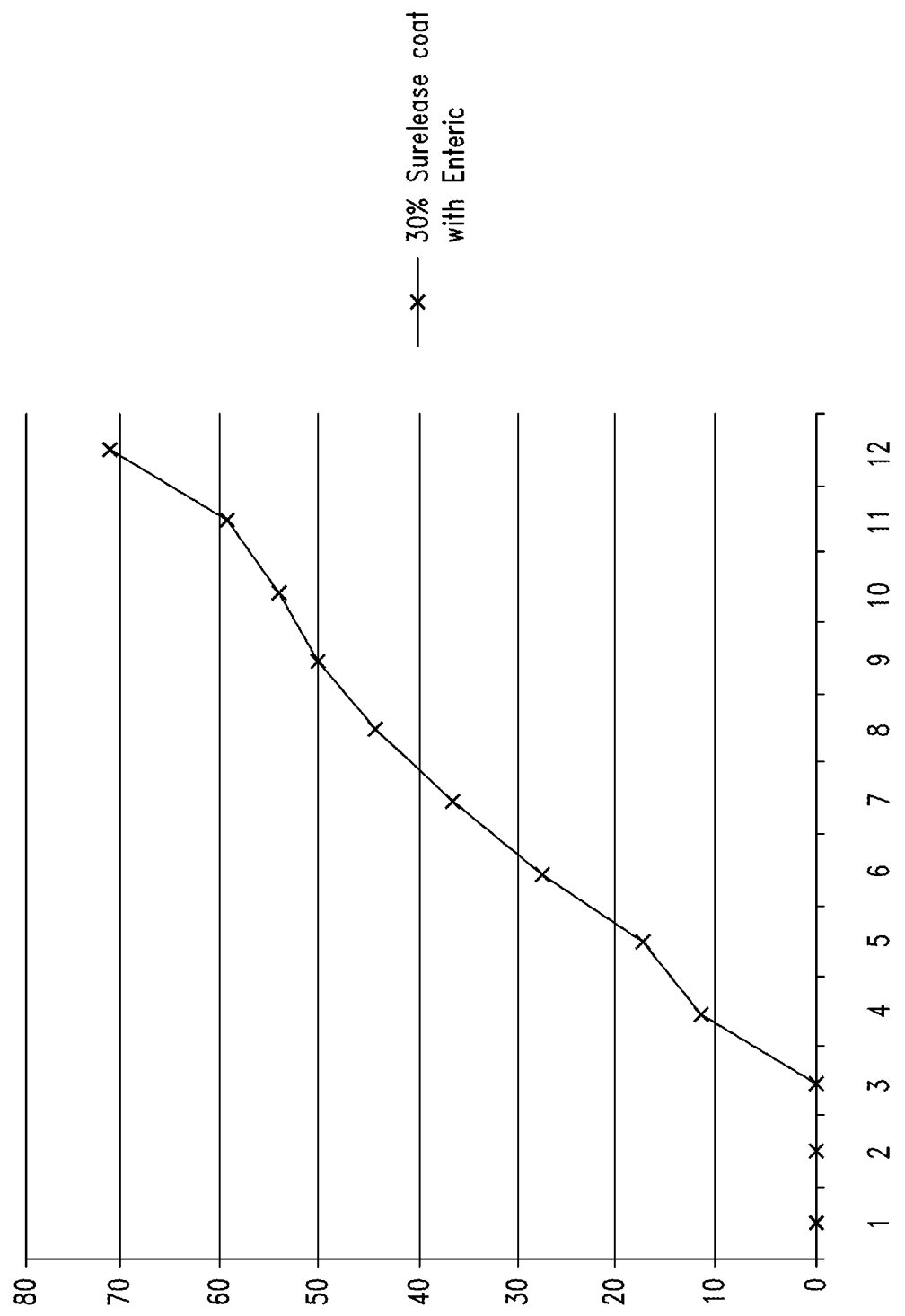
FIG. 8 shows release of mycophenolate sodium from yet another embodiment of a particulate subunit in accordance with the present disclosure that was exposed to a 2-hour incubation in acidic media (pH 1.2), followed pH 6.8 media.

FIG. 8 shows release of sodium mycophenolate from a particulate subunits (coated beads) comprising 30 wt % Surelease polymer coat and a protective enteric coating. pH was switched from 1.2 to 6.8 following 2 h incubation.

Figure 9:
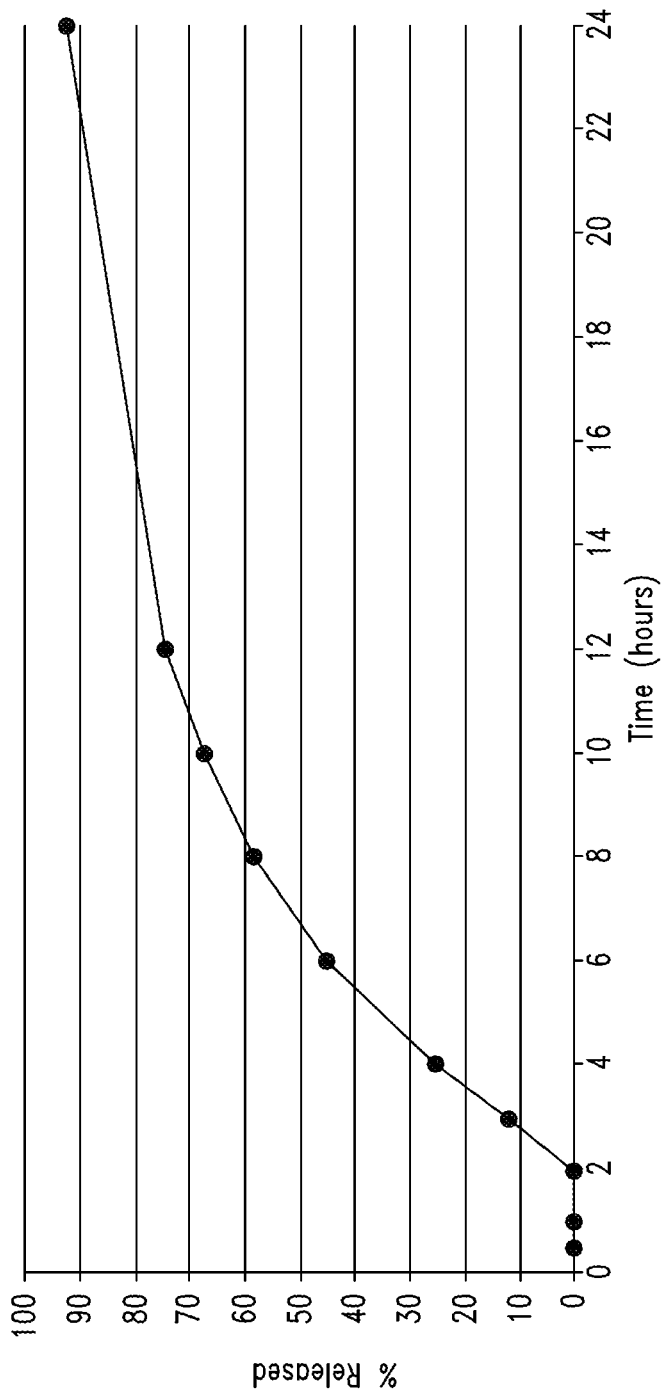
FIG. 9 shows release of sodium mycophenolate sodium from an embodiment of a particulate subunit according to the present disclosure, where the particulate subunit comprises a bead with a solvent-based coating and where the particulate subunit was exposed to a 2-hour incubation in acidic media (pH 1.2), followed by 12 hours in pH 6.8 media.
Figure 10:
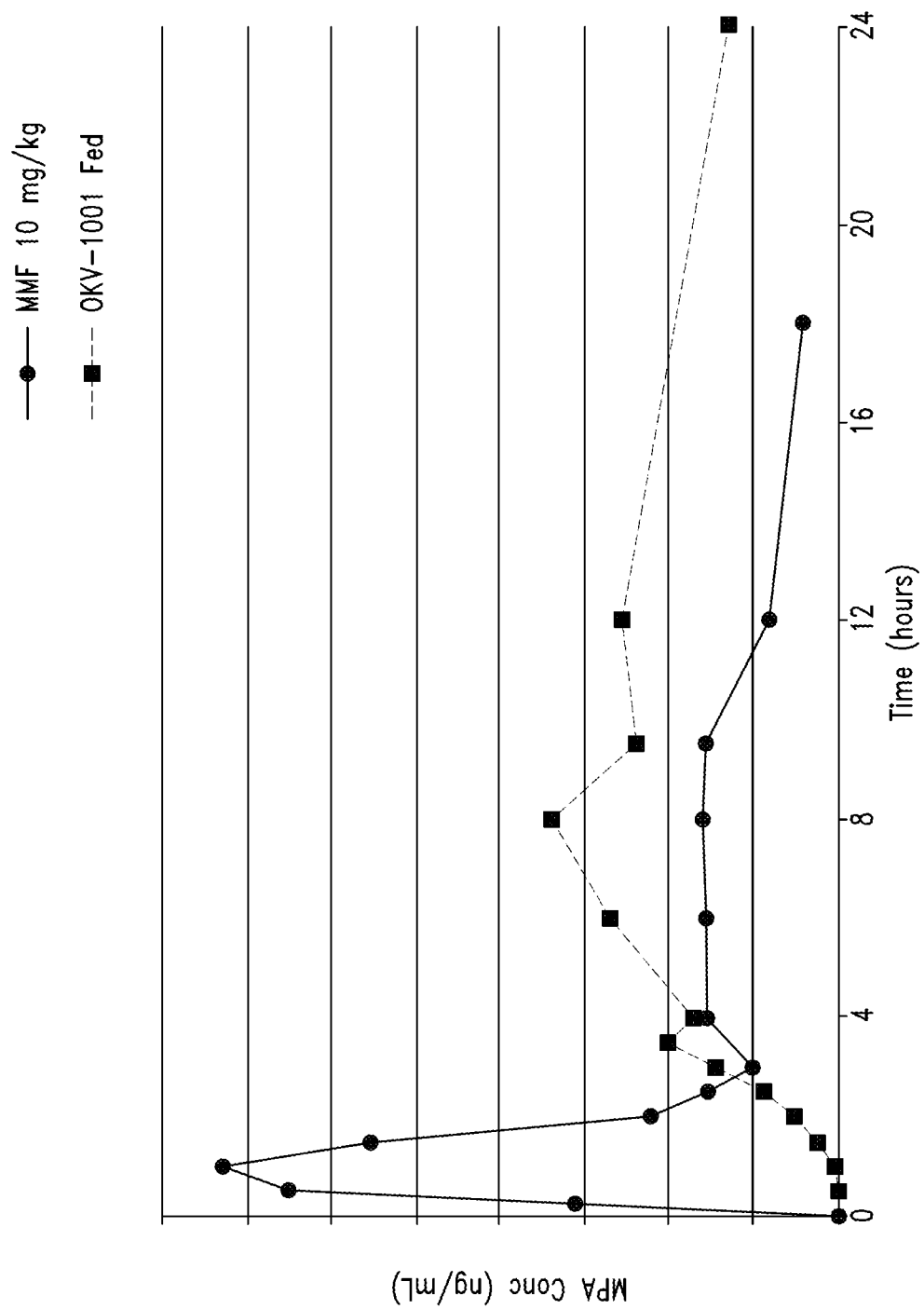
FIG. 10 shows relative levels of serum mycopenolic acid ([MPA]=ng/mL MPA) measured at the indicated timepoints following administration of either an immediate release mycophenolate mofetil solution (120 mg MMF BID, each dose containing; circles) to fasted canines or a controlled-release composition of the present disclosure to fed canines (270 mg "OKV-1001" containing 252 mg MPA; squares).
Figure 11:
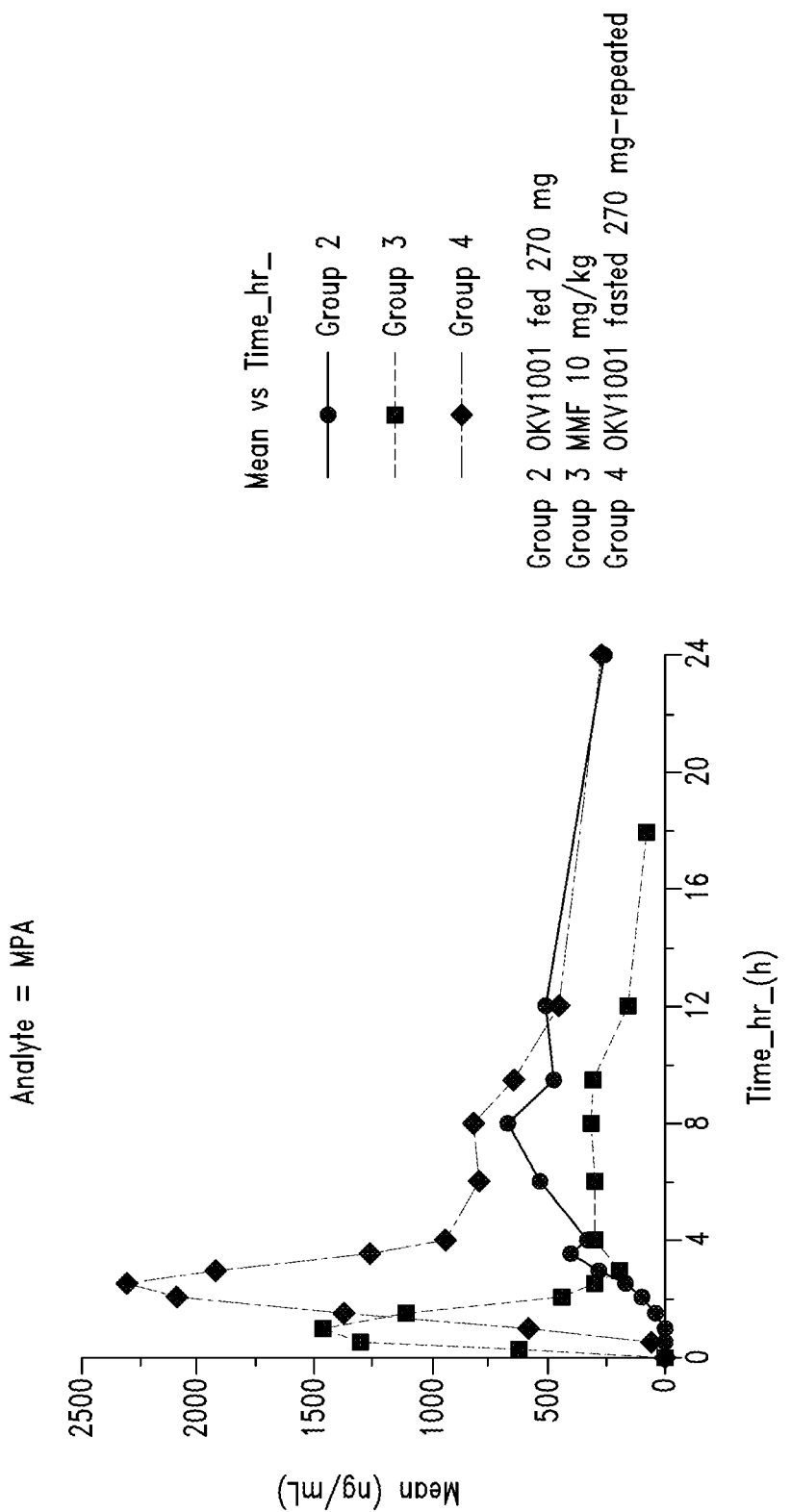
FIG. 11 provides another view of the data shown in FIG. 10 ("Groups" 2 and 3) and further provides mean serum levels (ng/mL) of MPA in fasted canines following administration of the controlled-release composition ("Group 4").
Figure 12:
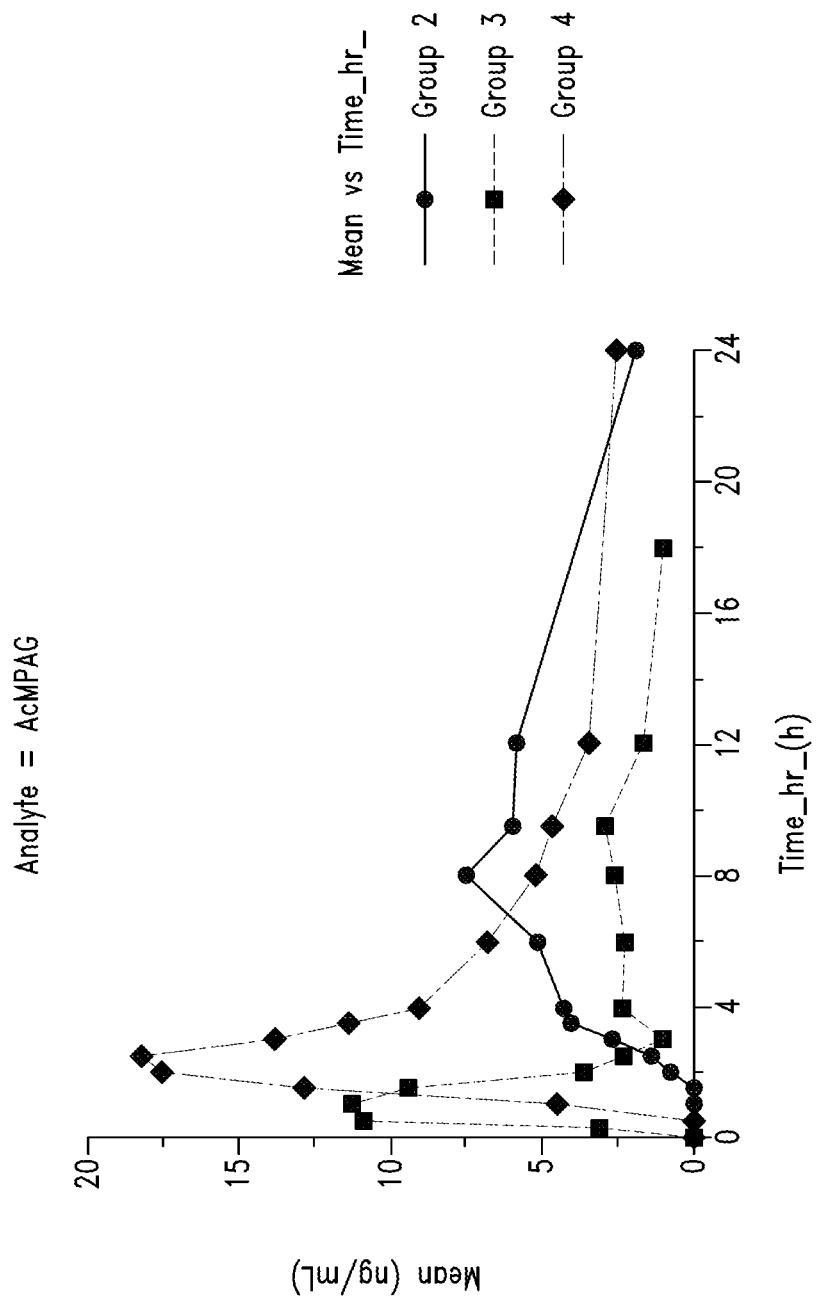
FIG. 12 shows mean serum levels (ng/mL) of the MPA metabolite acyl MPA glucoronide (AcMPAG) measured in the indicated canine treatment groups.
Figure 13:
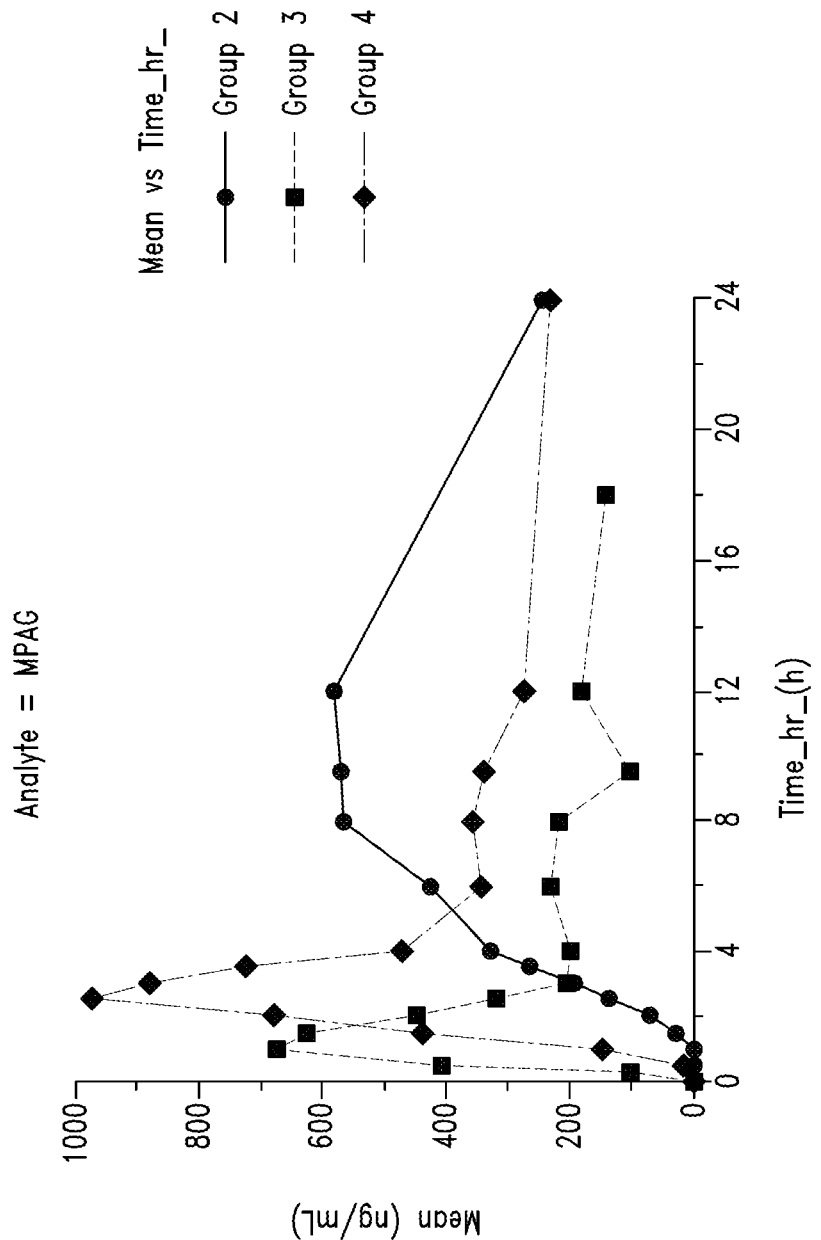
FIG. 13 shows mean serum levels (ng/mL) of the MPA metabolite MPA glucoronide (MPAG) measured in the indicated canine treatment groups.

FIG. 9 shows release of sodium mycophenolate from particulate subunits (coated beads) comprising a solvent-based coating. pH was switched from 1.2 to 6.8 following 2 h incubation.

Table 7 below provides MPA active agent release data from particulate subunits of two exemplary formulations according to the present disclosure. Two sets of extended-release enteric-coating Na.MPA coated beads were prepared as described above (22 wt % Surelease coating and 30 wt % coating) and placed in acid (2 h, pH 1.2) followed by a buffer that raised pH to approximately 6.8.

TABLE 8

| Hours Following Administration | % NaMPA released (22% Surelease) | % NaMPA released (30% Surelease) |
|---|---|---|
| 0.5 | 0.9 | 0.0 |
| 1 | 3.2 | 1.5 |
| 2 | 7.9 | 4.9 |
| 2.5 | 25.1 | 13.2 |
| 3 | 35.8 | 21.4 |
| 4 | 51.3 | 31.7 |
| 5 | 61.4 | 40.7 |
| 6 | 67.9 | 48.0 |
| 7 | 72.8 | 54.0 |
| 8 | 76.2 | 59.1 |
| 10 | 81.5 | 66.1 |
| 14 | 86.9 | 76.1 |

Example 2

Preparation of Mycophenolate Controlled-Release Mini-Tablets

Materials
Mycophenolate Sodium 20-60%, suitably 50%
Microcrystalline cellulose 30-60%, suitably 43%
Poly Vinyl pyrrolidone (PVP) 1-10%, suitably 5%
Magnesium Stearate 0.5-5%, suitably 2%

The required quantities of mycophenolate sodium and microcrystalline cellulose were mixed together in a high shear mixer for about 5 minutes.

The required quantity of PVP was dissolved in water to form a 10% w/w solution of PVP.

The PVP solution was gradually added to the high shear mixer and the blend was mixed until a wet mass was formed.

The wet mass was transferred to a fluid bed dryer and dried.

The dried granulation was passed through a sieve such that very coarse and very fine particles were removed.

The sieved granulation was transferred to a V blender and mixed with the Magnesium stearate for about 3 minutes.

The lubricated granules were compressed into mini-tablets using a 2 mm round standard concave multi tip tooling on a compression press.

The mini-tablets were coated with a seal coat, a controlled-release layer, and a protective layer, as described herein.

The appropriate quantity of mini-tablets can be administered to the veterinary subject, either filled in a capsule, as a slurry, as a sachet, a dragee, etc.

Example 3

In Vivo Pharmacokinetics of MPA in a Canine Model

Two single dose cross-over studies were conducted using a canine model (male beagle dogs) to evaluate the potential of an enteric coated-extended release sodium mycophenolate formulation ("EC-ER-Na.MP"). In a first cross-over study, the pharmacokinetics of MPA and its metabolites (MPAG and AcMPAG) following oral dosing of 180 mg of EC-Na.MPA was compared with intracolonic (IC) administration of Na.MPA. In a second cross-over study, 270 mg of an EC-ER-Na.MPA formulation was administered in the both fed and fasted states and pharmacokinetics were compared with oral administration of 10 mg/kg MMF in the fasted state. Both studies were conducted by Absorption Systems (San Diego, Calif.).

Study 1:

For three days prior to IC dosing, dogs (n=5) were offered a soft diet consisting of canned wet food (Pedigree® Choice Cuts). Otherwise, the dogs were offered their standard diet (LabDiet 5006 laboratory canine diet). Prior to each dosing event, the dogs were fasted for 12 hours prior to dosing until 4 hours post-dose, when food was returned. Animals had free access to water throughout the study. Prior to IC dosing, each dog was given a non-stimulant enema approximately 1 hour prior to dosing to remove feces from the colon. Prior to PO dosing, each dog (n=5) was pre-treated with an intramuscular dose of pentagastrin (6 µg/kg) approximately 30 minutes prior to dosing. Capsules were administered by placement in the back of the throat followed by a 10 mL flush with water.

Each dog received a total dose of 180 mg of MPA for each dose. For IC dosing, MPA was delivered as a solution via an endoscope, and for PO dosing each dog received a single Myfortic® 180 mg enteric coated capsule. Following administration, blood samples were collected up to 24 hours post-dose. Plasma concentrations of MPA, MPAG, and AcMPAG were determined with a qualified LC-MS/MS method, and pharmacokinetic parameters were determined with WinNonlin v.6.4 software.

Following IC dosing of MPA, maximum plasma concentrations (average $C_{max}$ of 29460±12587 ng/mL) were observed between 5 and 30 minutes post-dose. The average half-life was 5.55±1.77 hours, and the average exposure based on the dose-normalized $AUC_{last}$ was 1817±925 hr*kg*ng/mL/mg. MPAG after MPA dosing had an average $C_{max}$ of 4826±1156 ng/mL. The $t_{max}$ for MPAG ranged from 15 minutes to 1 hour post-dose, and the average $AUC_{last}$ was 11702±4794 hr*ng/mL. AcMPAG after MPA dosing had an average $C_{max}$ of 303±87.8 ng/mL. The $t_{max}$ for MPAG ranged from 5 to 15 minutes post-dose, and the average $AUC_{last}$ was 233±160 hr*ng/mL.

Following PO dosing of MPA, maximum plasma concentrations (average $C_{max}$ of 27320±12037 ng/mL) were observed between 30 minutes and 2 hours post-dose. The average half-life, determined in 2 dogs, was 4.49 hours, and the average exposure based on the dose-normalized $AUC_{last}$ was 2234±799 hr*kg*ng/mL/mg. MPAG after MPA dosing had an average $C_{max}$ of 14316±5033 ng/mL. The $t_{max}$ for MPAG ranged from 1 to 2 hours post-dose, and the average $AUC_{last}$ was 28882±8313 hr*ng/mL. AcMPAG after MPA dosing had an average $C_{max}$ of 426±113 ng/mL. The $t_{max}$ for MPAG ranged from 30 minutes to 2 hours post-dose, and the average $AUC_{last}$ was 529±217 hr*ng/mL.

Based on average values, systemic exposure to MPA was similar following IC and PO dosing. The average $C_{max}$ after IC and PO doses were 29460 and 27320 ng/mL, respectively, and the average dose-normalized $AUC_{last}$ values were 1817 and 2234 hr*kg*ng/mL/mg, respectively. However, MPA did appear to be more rapidly absorbed following IC dosing in comparison to the PO dose. MPAG was present at a much higher concentration in the plasma than AcMPAG. Systemic exposure to each of these glucuronide metabolites after IC dosing was approximately 40% of that after PO dosing. The average $AUC_{last}$ for MPAG was 28882 hr*ng/mL after PO dosing and 11702 hr*ng/mL after IC dosing. The average $AUC_{last}$ for AcMPAG was 529 hr*ng/mL after PO dosing and 233 hr*ng/mL after IC dosing.

The mean pharmacokinetic parameters and the drug to metabolite ratios are summarized in Table 9. The MPA/MPAG ratio and MPA/AcMPAG ratio were each observed to be almost 2-fold higher following the IC dosing compared to the oral administration.

TABLE 9

Mean MPA, MPAG and AcMPAG Pharmacokinetic Parameters following Oral and Intracolonic Administration of Na.MPA (n = 5 male beagle dogs)

| | MPA | | MPAG | | AcMPAG | | MPA/MPAG | MPA/AcMPAG |
|---|---|---|---|---|---|---|---|---|
| | Mean | SD | Mean | SD | Mean | SD | Ratio | Ratio |
| ORAL | | | | | | | | |
| Animal Weight (kg) | 11.1 | 0.5 | | | | | | |
| Dosed per dog (mg) | 180 | 0 | | | | | | |
| Dose (mg/kg) | 16.2 | 0.7 | | | | | | |
| $C_{max}$ (ng/mL) | 27320 | 12037 | 14316 | 5033 | 426 | 113 | | |
| $t_{max}$ (hr) | 1 | 0.61 | 1.4 | 0.55 | 1.1 | 0.55 | | |
| $t_{1/2}$ (hr) | 4.49 | ND | 7.12 | 1.95 | ND | ND | | |
| $MRT_{last}$ (hr) | 2.86 | 0.856 | 3.75 | 0.371 | 1.71 | 0.628 | | |
| $AUC_{last}$ (hr · ng/mL) | 36435 | 13501 | 28882 | 8313 | 529 | 217 | 1.42 | 88.40 |
| $AUC_{\infty}$ (hr · ng/mL) | 45693 | ND | 30360 | 9234 | ND | ND | 1.29 | ND |
| INTRACOLONIC | | | | | | | | |
| Animal Weight (kg) | 10.7 | 0.5 | | | | | | |
| Dosed per dog (mg) | 180 | 0 | | | | | | |
| Dose (mg/kg) | 16.8 | 0.8 | | | | | | |
| $C_{max}$ (ng/mL) | 29460 | 12587 | 4826 | 1156 | 303 | 87.8 | | |
| $t_{max}$ (hr) | 0.23 | 0.17 | 0.6 | 0.38 | 0.22 | 0.07 | | |
| $t_{1/2}$ (hr) | 5.55 | 1.77 | 6.61 | 2.36 | ND | ND | | |
| $MRT_{last}$ (hr) | 2.76 | 0.324 | 4.16 | 0.688 | 1.33 | 0.897 | | |
| $AUC_{last}$ (hr · ng/mL) | 30993 | 17092 | 11702 | 4794 | 233 | 160 | 2.86 | 171.19 |
| $AUC_{\infty}$ (hr · ng/mL) | 31948 | 17903 | 13475 | 4252 | ND | ND | 2.45 | ND |

$C_{max}$: maximum plasma concentration;
$t_{max}$: time of maximum plasma concentration;
$t_{1/2}$: half-life;
$MRT_{last}$: mean residence time, calculated to the last observable time point;
$AUC_{last}$: area under the curve, calculated to the last observable time point;
$AUC_{\infty}$: area under the curve, extrapolated to infinity;
BLOQ: below the limit of quantitation (1 ng/mL);
ND: not determined.

Study 2:

In this treatment cross-over study, the pharmacokinetics of MPA and its metabolites (MPAG and AcMPAG) following 270 mg EC-ER-Na.MP ("OKV-1001") administered in the fed and fasted state were compared with those following oral administration of immediate release 10 mg/kg MMF in a fasted state (n=5 per dose group; same group of dogs for each treatment).

For EC-ER-Na.MP and MMF administration in the fasted state, dogs were fed a certified laboratory diet (5006 laboratory canine diet from LabDiet) and then fasted for a minimum of twelve hours prior to dosing. Food was provided approximately 4 hours post-dose. Water was supplied ad libitum to the animals.

For EC-ER-Na.MP administration in the fed state, dogs were fed a certified laboratory diet (5006 laboratory canine diet from LabDiet), fasted for a minimum of twelve hours, and then fed (Alpo Can food) prior to dosing and then dosed no more than 30 minutes post completion of food. The amount of food provided and consumed by each animal was recorded. Regular lab diet was provided approximately 4 hours post-dose. Water was supplied ad libitum to the animals.

For MMF administration, an MMF oral suspension was prepared according to the instructions for CellCept®. Leftover dosing solutions were stored at room temperature.

For both EC-ER-Na.MP treatments, blood was collected pre-dosing, then at either: 30 minutes, 1, 1.5, 2, 2.5, 3, 3.5, 4, 6, 8, 9, 12, and 24 hours (processed to obtain plasma); or 1, 2, 3, 4, 6, 8, 12, and 24 hours (processed to PBMC). For the MMF treatment, blood was collected at pre-dose, 15 minutes, 30 minutes, 1, 1.5, 2, 2.5, 3, 4, 6, 8, 9, 12, and 18 hours (processed to plasma); or at pre-dose, 1, 2, 3, 4, 6, 8, 12, and 18 hours (processed to obtain PBMCs).

Plasma concentrations of MPA, MPAG, and AcMPAG were determined with a qualified LC-MS/MS method, and pharmacokinetic parameters were determined with WinNonlin v.6.4 software. Plasma concentration curves are shown in FIGS. 10-13. The mean pharmacokinetic parameters and drug to metabolite ratios are summarized in Table 10. Under fasted conditions, the MPA/MPAG ratio was 1.5 to 2.0 fold higher with EC-ER-Na.MP compared to the reference oral dosing (Table 10). The MPA/AcMPAG ratio also trended to be higher, although to a lesser extent.

TABLE 10

Mean Pharmacokinetic Parameters of MPA and Metabolites Following Oral MMF and EC-ER-Na.MP Administration

| | MPA | | MPAG | | AcMPAG | | MPA/MPAG | MPA/AcMPAG |
|---|---|---|---|---|---|---|---|---|
| | Mean | SD | Mean | SD | Mean | SD | Ratio | Ratio |
| ORAL MMF | | | | | | | | |
| Animal Weight (kg) | 11 | 1.4 | | | | | | |
| MMF Dose (mg/kg) | 10 | — | | | | | | |
| Dose (mg/kg) MPA Equivalent | 7.39 | — | | | | | | |
| $C_{max}$ (ng/mL) | 1991 | 1434.5 | 800.2 | 300.8 | 18.25 | 14.61 | | |
| $t_{max}$ (hr) | 0.75 | 0.5 | 1.1 | 0.42 | 0.75 | .05 | | |
| $t_{1/2}$ (hr) | 5.78 | 5.68 | 14.30 | 10.91 | 2.42 | 0.65 | | |
| $MRT_{last}$ (hr) | 5.89 | 1.19 | 7.2 | 0.65 | 5.83 | 0.44 | | |
| $AUC_{last}$ (hr? · ng/mL) | 5644 | 2144 | 3899 | 1240 | 44.6 | 21.7 | 1.48 | 139.8 |
| $AUC_?$ (hr? · ng/mL) | 6543 | 3277 | 6615.7 | 2637.8 | 50.8 | 23.7 | 1.02 | 133.3 |
| EC-ER-Na.MPA | | | | | | | | |
| Animal Weight (kg) | 11.1 | 1.3 | | | | | | |
| Na.MPA Dose (mg) | 270 | — | | | | | | |
| Dose (mg/kg) MPA Equivalent | 22.94 | 2.47 | | | | | | |
| $C_{max}$ (ng/mL) | 2334 | 823.6 | 983.8 | 364.9 | 20.98 | 8.63 | | |
| $t_{max}$ (hr) | 2.3 | 0.27 | 2.3 | 0.45 | 2.1 | 0.42 | | |
| $t_{1/2}$ (hr) | 7.53 | 0.45 | 8.73 | 1.29 | 6.62 | 2.62 | | |
| $MRT_{last}$ (hr) | 8.44 | 1.19 | 9.89 | 1.77 | 7.9 | 2.06 | | |
| $AUC_{last}$ (hr? · ng/mL) | 15187 | 2678 | 7884.5 | 2771 | 120.9 | 50.3 | 2.18 | 169.0 |
| $AUC_?$ (hr? · ng/mL) | 18140 | 3111 | 10784 | 5110 | 145.9 | 63.6 | 1.99 | 163.0 |

$C_{max}$: maximum plasma concentration;
$t_{max}$: time of maximum plasma concentration;
$t_{1/2}$: half-life calculated using 2 points in the terminal phase;
$MRT_{last}$: mean residence time, calculated to the last observable time point;
$AUC_{last}$: area under the curve, calculated to the last observable time point;
$AUC_?$: area under the curve, extrapolated to infinity, if $t_{1/2}$ value was not available mean group value was used;
BLOQ: below the limit of quantitation (1 ng/mL);
ND: not determined.

Figure 14:
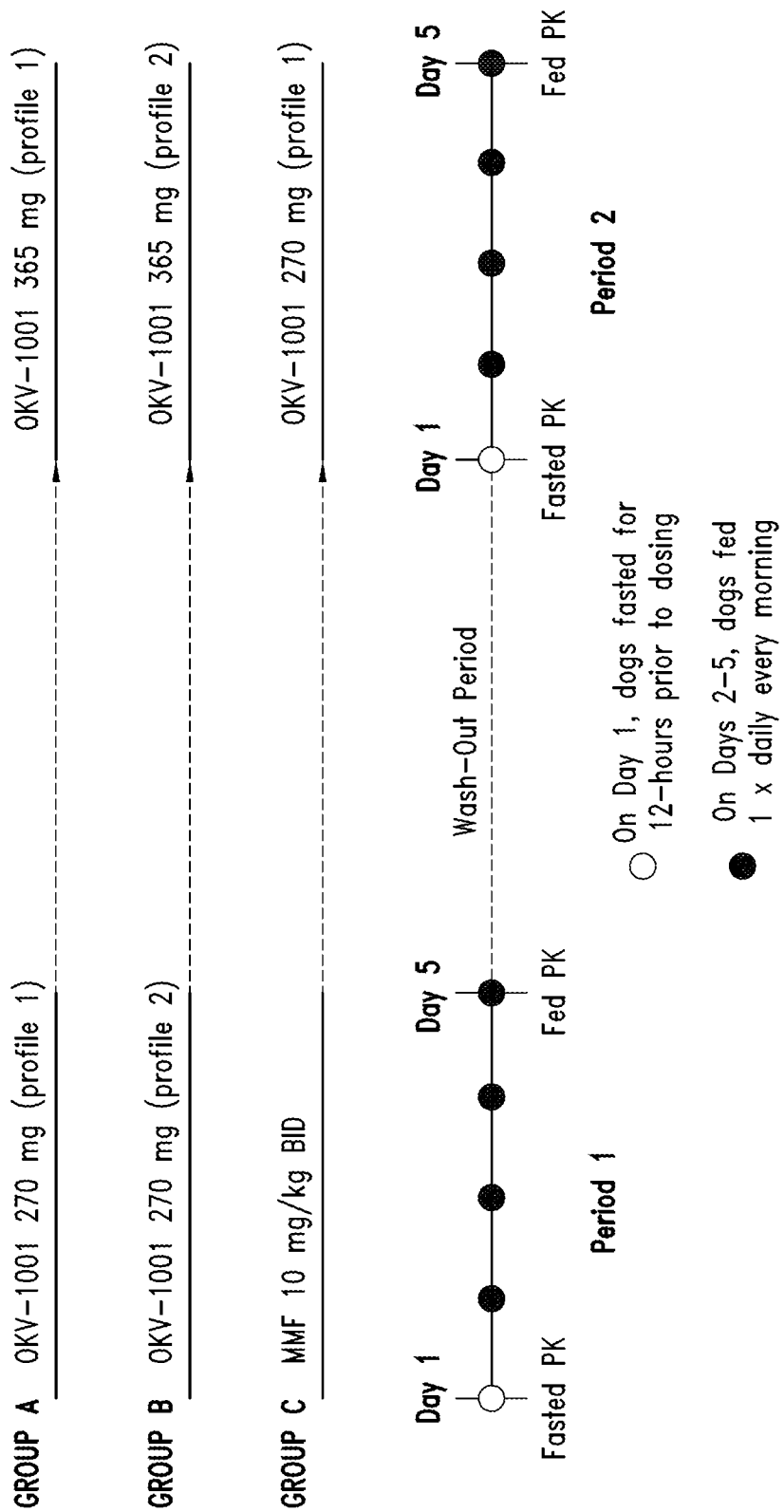
FIG. 14 provides a schematic diagram showing the design of a 2-treatment, 2-period, sequential adaptive cross-over study by the inventors of the present disclosure.

Study 3:

Another cross-over study was performed to determine the single-dose and steady state pharmacokinetics of MPA and its metabolites (MPAG and AcMPAG). The study design is illustrated in FIG. 14. Specifically, three (3) groups of healthy male beagle dogs (n=7 per group for a total of 21 dogs; Marshall BioResources, North Rose, N.Y., USA) participated in a two-treatment, two-period, sequential, adaptive cross-over study. Two five-day, repeat-dosing study periods were separated by a 16-day washout period. Dogs were at least two years of age at the time of enrollment.

In the first five-day period, three groups of dogs (n=7 per group) were randomized to receive either OKV-1001 (270 mg) Profile 1 QD (Group A), OKV-1001 (270 mg) Profile 2 QD (Group B) or MMF (10 mg/kg) oral suspension BID (Group C). Profile 1 was formulated for faster release of the MPA active agent as compared to Profile 2. MMF oral suspension (CellCept® oral suspension, Genentech USA Inc., South San Francisco, Calif.) dosed at 10 mg/kg B.I.D served as the reference group. A 16-day wash period ensued after the first five-day period, and results from the first period were examined. Dogs were then crossed-over in the second period to receive OKV-1001 (365 mg) Profile 1 QD (Group A) or OKV-1001 (365 mg) Profile 2 QD (Group B) or either OKV-1001 (270 mg) Profile 1 QD (Group C). The treatments received by the dogs in each group and period are summarized in Table 11.

TABLE 11

Treatments Received by Each Group in Study 3

| | Period 1 | Period 2 |
|---|---|---|
| Group A (n = 7) | OKV-1001$_{P1}$ 270 mg (QD) | OKV-1001$_{P1}$ 365 mg (QD) |
| Group B (n = 7) | OKV-1001$_{P2}$ 270 mg (QD) | OKV-1001$_{P2}$ 365 mg (QD) |
| Group C (n = 7) | MMF 10 mg/kg (BID) | OKV-1001$_{P1}$ 270 mg (QD) |

The two study periods had identical feeding and sampling procedures. On Day 1, PK samples were collected after a 12-hour fast, while samples were collected 1 hour after the animals were fed on Day 5. At the time of dosing, any uneaten food was removed, and the amount of food provided and consumed by each animal was recorded. On Days 2-5, animals were fed once daily in the morning, 1 hour prior to administration of the morning dose.

On Day 1 and Day 5, serial blood samples collected via the jugular vein were collected prior to dosing (0 min) and at 15 and 30 min, and then 1, 1.5, 2, 2.5, 3, 4, 6, 8, 9 and 12 hours after MMF administration. For OKV-1001, samples were collected prior to dosing (0 min), and at 30 min, and then 1, 1.5, 2, 2.5, 3, 3.5, 4, 6, 8, 9, 12 and 24 hours. A qualified and validated GLP ready LC-MS/MS method was used to quantify plasma MPA, MPAG, AcMPAG plasma concentrations.

The general health of each animal was assessed at every blood sampling time point during the course of the study. On study days with no blood sampling or only one blood sampling time point, the general health was assessed at least twice daily (AM and PM).

Figure 15:
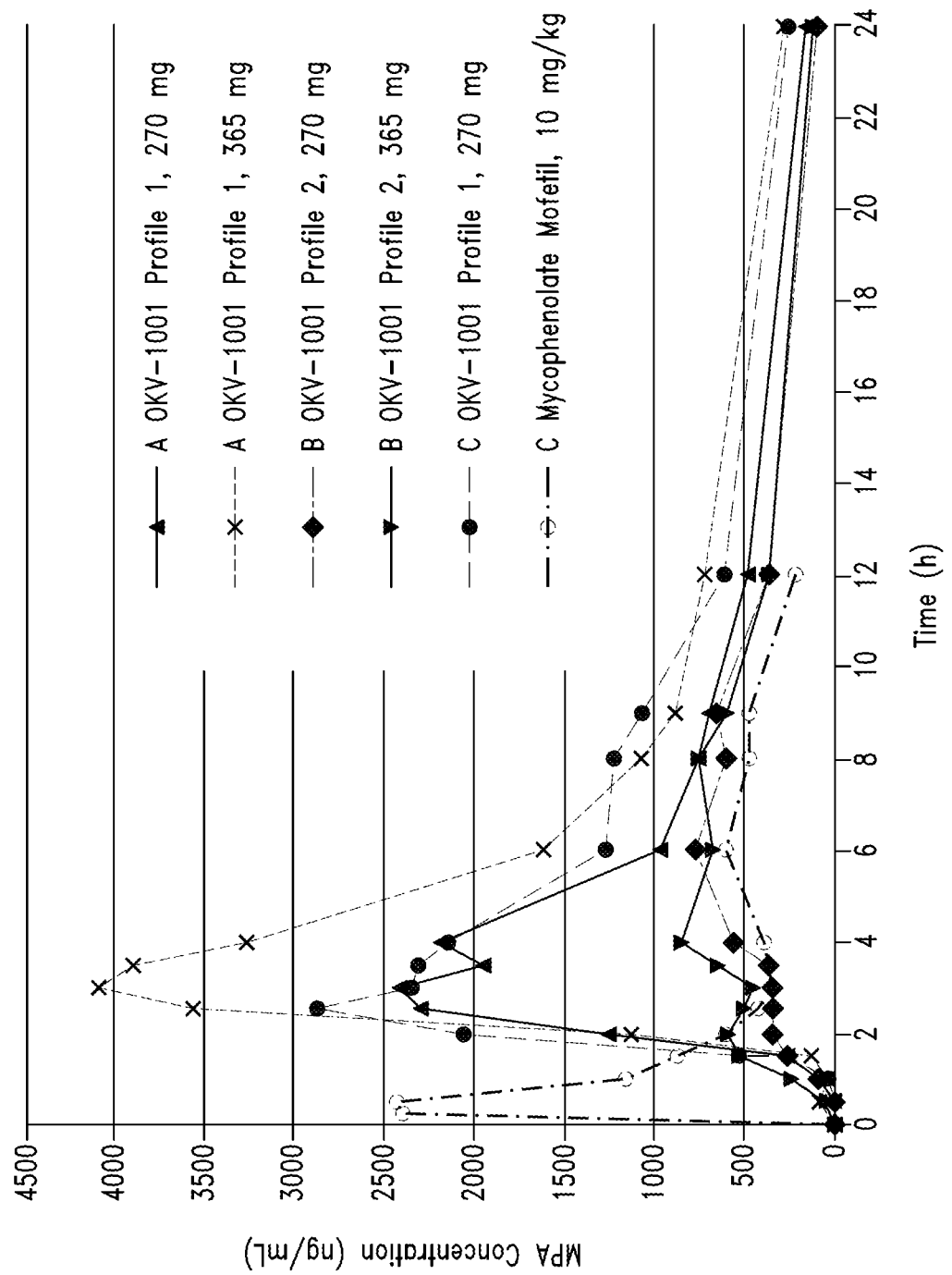
FIG. 15 shows Day 1 serum MPA concentrations over time from the canine "Period 1" and "Period 2" treatment groups depicted in FIG. 14.
Figure 16:
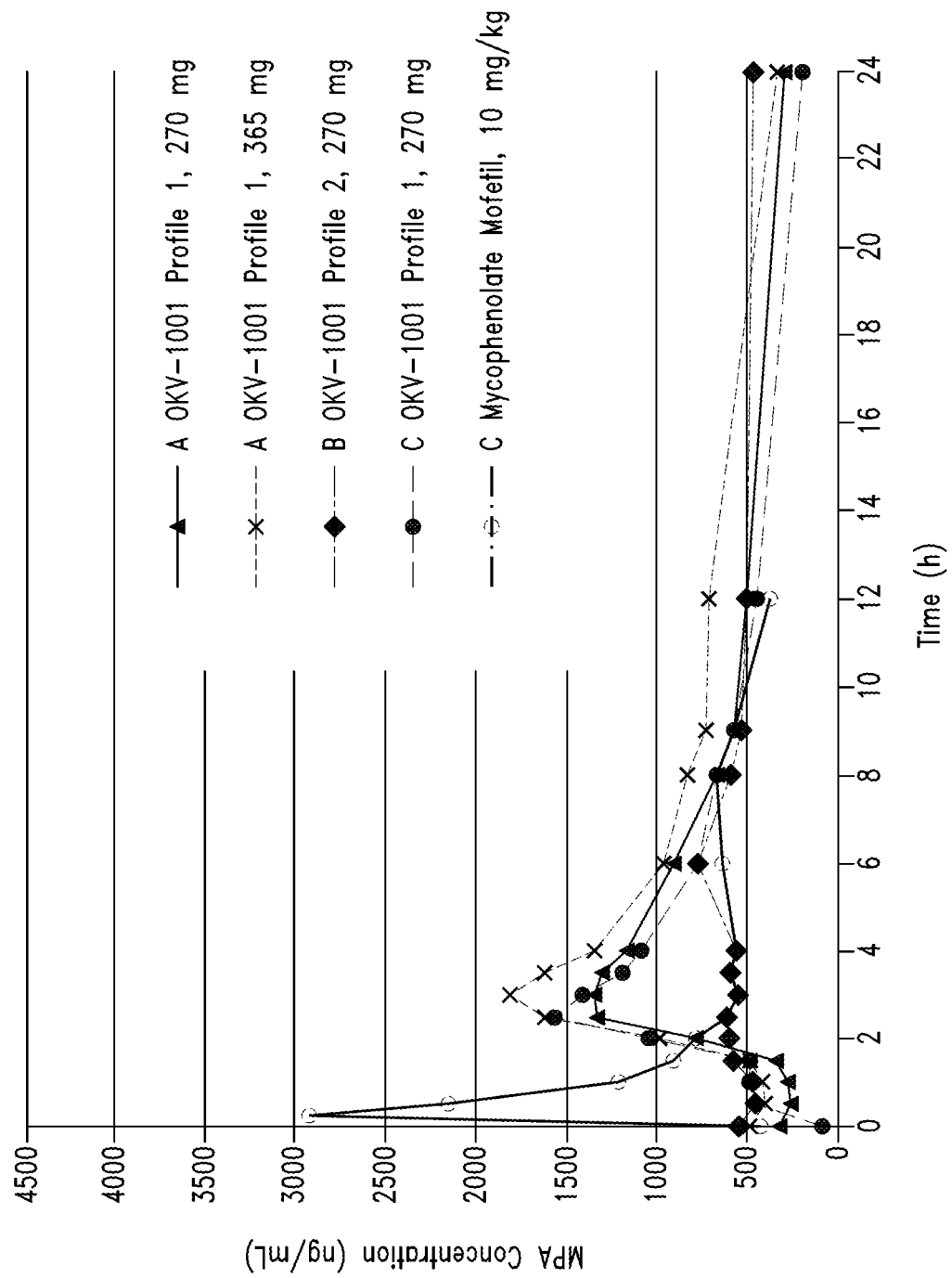
FIG. 16 shows Day 5 serum MPA concentrations over time from the canine "Period 1" and "Period 2" treatment groups depicted in FIG. 14.

Standard non compartmental pharmacokinetic parameters ($C_{max}$, $T_{max}$, $t_{1/2}$, $AUC_{last}$ and $AUC_{inf}$ following the Day 1 dosing; $C_{max}$, $T_{max}$, and $AUC_{tau}$ following the Day 5 dosing where tau is 12 h for MMF and 24 h for OKV-1001) were estimated using Phoenix Winnonlin software 64 (Build 7.0.0.2535) for MPA, MPAG and AcMPAG. MPA plasma concentration levels for each treatment group on Day 1 (fasted; single-dose) are shown in FIG. 15. MPA plasma concentration levels for each treatment group on Day 5 (fed; steady state) are shown in FIG. 16. Calculated drug:metabolite (D:M) ratios for Group C, Group A, and Group B are shown in Tables 12, 13, and 14, respectively. Reference ratio values from Study 2 are also shown. Non-compartmental PK parameter estimates for all treatment groups are provided in Table 15. It should be noted that data from Group B/Period 2/Day 5 was not obtained from 5 of the 7 dogs.

TABLE 12

Study 3 Group C and Study 2: Mean D:M Ratio Summary

| | Study 3 (Repeat Dose) | | Study 2 (Single Dose) | |
| --- | --- | --- | --- | --- |
| | MMF | OKV-1001 (270 mg) | MMF | OKV-1001 (270 mg) |
| MPA/MPAG Day 1 | 1.6 (0.78-3.07) | 1.5 (0.69-2.36) | 1.02 (0.70-1.77) | 1.99 (1.10-3.30) |
| MPA/MPAG Day 5 | 1.6 (0.84-3.35) | 0.84 (0.48-1.43) | | |
| MPA/AcMPAG Day 1 | 130 (80-219) | 90 (65-160) | 133 (90-229) | 163 (94-380) |
| MPA/AcMPAG Day 5 | 84 (60-168) | 76 (53-145) | | |

TABLE 13

Study 3 Group A and Study 2: Mean D:M Ratio Summary

| | Study 3 (Repeat Dose) | | Study 2 (Single Dose) | |
| --- | --- | --- | --- | --- |
| | OKV-1001 P1 (270 mg) | OKV-1001 P1 (365 mg) | MMF | OKV-1001 (270 mg) |
| MPA/MPAG Day 1 | 1.97 (1.05-4.73) | 1.48 (0.80-3.18) | 1.02 (0.70-1.77) | 1.99 (1.10-3.30) |
| MPA/MPAG Day 5 | 1.27 (0.81-2.71) | 0.75 (0.42-1.52) | | |
| MPA/AcMPAG Day 1 | 119 (77-155) | 94 (81-130) | 133 (90-229) | 163 (94-380) |
| MPA/AcMPAG Day 5 | 104 (47-191) | 74 (51-128) | | |

TABLE 14

Study 3 Group B and Study 2: Mean D:M Ratio Summary

| | Study 3 (Repeat Dose) | | Study 2 (Single Dose) | |
| --- | --- | --- | --- | --- |
| | OKV-1001 P2 (270 mg) | OKV-1001 P2 (365 mg) | MMF | OKV-1001 (270 mg) |
| MPA/MPAG Day 1 | 1.95 (1.22-3.5) | 1.10 (1.0-1.94) | 1.02 (0.70-1.77) | 1.99 (1.10-3.30) |
| MPA/MPAG Day 5 | 1.6 (0.86-2.96) | 0.6 (0.52, 0.70) (n = 2) | | |
| MPA/AcMPAG Day 1 | 163.5 (91-418) | 131 (92-273) | 133 (90-229) | 163 (94-380) |
| MPA/AcMPAG Day 5 | 145 (63-257) | 80 (69, 91) (n = 2) | | |

TABLE 15

Mean Single-Dose and Steady State MPA and MPAG Pharmacokinetic Parameters - Group A (n = 7)

| Period/ Formulation | Day | | Tmax hr | Cmax ng/mL | AUC[a] hr * ng/mL | Tmax hr | Cmax ng/mL | AUC[a] hr * ng/mL |
|---|---|---|---|---|---|---|---|---|
| | | | | | MPA | | | MPAG |
| GROUP A | | | | | | | | |
| Period 1/ | 1 | Mean | 3.00 | 2897.1 | 18078 | 3.07 | 953.6 | 9873 |
| OKV-1001 | | SD | 0.87 | 1283.8 | 7615 | 0.53 | 146.0 | 2721 |
| Profile 1, 270 mg | 5 | Mean | 2.93 | 1515.9 | 14093 | 3.36 | 1640.4 | 12182 |
| | | SD | 0.45 | 535.8 | 6429 | 0.38 | 704.6 | 5999 |
| Period 2/ | 1 | Mean | 3.00 | 4895.7 | 28200[b] | 3.64 | 2311.4 | 20426[c] |
| OKV-1001 | | SD | 0.58 | 987.9 | 11231 | 0.48 | 732.9 | 5572 |
| Profile 1, 365 mg | 5 | Mean | 2.93 | 1920.3 | 17464 | 3.29 | 3442.9 | 24234 |
| | | SD | 0.35 | 924.8 | 9670 | 0.49 | 877.4 | 10902 |
| GROUP B[d] | | | | | | | | |
| Period 1/ | 1 | Mean | 7.14 | 835.1 | 9503 | 7.57 | 310.6 | 4957 |
| OKV-1001 | | SD | 1.46 | 463.8 | 4215 | 1.51 | 65.7 | 1357 |
| Profile 2, 270 mg | 5 | Mean | 5.14 | 854.0 | 12981 | 6.57 | 505.9 | 6899 |
| | | SD | 2.78 | 861.7 | 15691 | 7.86 | 309.2 | 4649 |
| Period 2/ | 1 | Mean | 4.21 | 1037.3 | 11099 | 7.29 | 714.4 | 9747 |
| OKV-1001 | | SD | 1.82 | 654.8 | 7237 | 1.98 | 169.4 | 2496 |
| Profile 2, 365 mg | | | | | | | | |
| GROUP C | | | | | | | | |
| Period 1/ | 1 | Mean | 0.32 | 2950.0 | 8231 | 0.43 | 1032.1 | 5303 |
| Mycophenolate | | SD | 0.12 | 1730.4 | 3412 | 0.12 | 368.0 | 1497 |
| Mofetil 10 mg/kg | 5 | Mean | 0.36 | 3238.6 | 8672 | 0.71 | 1430.6 | 5962 |
| | | SD | 0.13 | 1437.8 | 2939 | 0.27 | 722.7 | 1687 |
| Period 2/ | 1 | Mean | 2.79 | 3042.9 | 23324 | 3.50 | 1584.3 | 16749[b] |
| OKV-1001 | | SD | 0.70 | 612.9 | 10366 | 1.22 | 333.0 | 7447 |
| Profile 1, 270 mg | 5 | Mean | 2.79 | 1666.1 | 13023 | 3.00 | 2382.9 | 15814 |
| | | SD | 0.39 | 721.3 | 4738 | 0.50 | 547.7 | 3758 |

[a]$AUC_{inf}$ for Day 1 and $AUC_{0-24}$ for Day 5
[b]n = 6
[c]n = 5
[d]Group B/Period 2/Day 5 is not presented because data are not available from 5 dogs.

Example 4

Manufacture of a Controlled-Release MPA Composition

Controlled-release MPA compositions (two profiles, "Profile 1" and "Profile 2") were manufactured as follows:

1. Required quantities of Hypromellose 2910 and purified water were mixed together in a suitable container until the Hypromellose is completely dissolved. The required amount of sodium mycophenolate was added to the hypromellose solution and mixed until all of the drug substance was dissolved.

2. A suitable quantity of microcrystalline cellulose spheres was loaded into the chamber of an appropriately sized fluid bed coater. The beads were pre-warmed to 48° C.

3. The drug-binder solution prepared in Step 1 was sprayed on to the microcrystalline spheres in the fluid bed coater while the bed was maintained at 50° C. The drug binder solution was sprayed on the spheres until a weight gain of 44% was achieved on the dry beads.

4. The drug loaded beads were dried at ambient temperature for approximately 10 minutes while the air flow was maintained at 75 cubic feet per minute (cfm)

5. A subcoating solution was prepared by mixing Opadry Clear and Purified Water in a suitable mixer until a clear solution was formed.

6. A suitable quantity of drug loaded beads was placed in the chamber of an appropriately sized fluid bed coater. The beads were pre-warmed to 50° C. and maintained at 50° C. during the subcoating process.

7. The subcoating solution prepared in Step 5 was sprayed on to the drug-coated beads in the fluid bed coater until a weight gain of 7% was achieved on the beads. The beads were dried at ambient temperature for approximately 10 minutes while the airflow is maintained at 90 cfm.

8. The rate control membrane solution was prepared as follows: Required quantities of DI water and ethanol were mixed together in a suitable mixer until homogenous. Dibutyl sebacate was added and mixed to form a homogenous suspension. Ethyl cellulose and Klucel EF were added and mixed to form a homogenous suspension. The required quantity of talc was added and mixed until a uniform suspension was formed.

9. A suitable quantity of sub-coated beads was placed in the chamber of an appropriately sized fluid bed coater. The beads were pre-warmed to 42° C.

10. The rate control membrane prepared in Step 8 was sprayed onto the drug-coated beads in the fluid bed coater. The membrane coating solution was sprayed on the spheres until a weight gain of 30% (Profile 1) or 45% (Profile 2) was achieved on the beads. After completion of coating, beads were dried under ambient temperature for approximately 10 minutes with an air flow volume if 50 cfm.

11. The enteric coat solution was prepared by mixing a required quantity Plasacryl HTP 20 with required quantity of DI water. Eudragit L30D 55 was dispersed and mixed into this solution until a homogenous suspension was obtained.

12. A suitable quantity of membrane-coated beads was placed in the chamber of an appropriately sized fluid bed coater. The beads were pre-warmed to 29° C.

13. The enteric coating solution prepared in Step 11 was sprayed on to the drug-coated beads in the fluid bed coater. The enteric coating solution was sprayed on the spheres until a weight gain of 25% was achieved on the beads for both Profile 1 and Profile 2 formulations. The beads were dried at ambient temperature for approximately 10 minutes after coating was complete.

14. The dried beads were manually filled into a Veterinary Size 13 gelatin capsule. The capsule was filled with beads equivalent to either 180 mg or 270 mg of mycophenolate sodium. The final MDDS product composition containing 270 mg of mycophenolate sodium was as shown in Table 16.

TABLE 16

Final product composition of QKV-1001 (270 mg Na.MPA)

| Functional layer | Component | Compendial Grade | % w/w | mg/dosage unit | Total weight (mg) |
|---|---|---|---|---|---|
| Drug Loaded beads (44.0% w.g. theoretical) | Cellets ®700 (Microcrystalline Cellulose Spheres) | NF | Core | 635.12 | 935.12 |
| | Mycophenolate Sodium | USP | 13.35 | 270 | |
| | HPMC 606 (Hypromellose 2910) | USP | 1.65 | 33.4 | |
| | Purified Water | In-house | 85.00 | 0 | |
| Total | | | 100.00 | 935.12 | 935.12 |
| Sub Coat (7.0% w.g. theoretical) | Opadry Clear 03O190001 | USP | 10.00 | 65.46 | 1000.58 |
| | Purified Water | In-house | 90.00 | 0 | |
| | | | 100.00 | 65.46 | |
| Rate Control membrane* (20.0% theoretical w.g.) | ECN10 (Ethylcellulose) | USPNF | 4.154 | 138.54 | 1200.70 |
| | Klucel EF (Hydroxypropyl Cellulose) | USPNF | 0.462 | 15.41 | |
| | Talc | USP | 0.923 | 30.78 | |
| | Dibutyl Sebacate | USPNF | 0.461 | 15.38 | |
| | DI Water | N/A | 9.40 | 0 | |
| | Ethanol 190 proof | USP | 84.60 | 0 | |
| | | | 100.00 | 200.12 | |
| Enteric coat (20% w.g.) | Eudragit L30D-55 | USP | 57.0 | 205.32 | 1440.84 |
| | Plasacryl HTP20 | USP | 14.55 | 34.82 | |
| | DI Water | N/A | 28.45 | 0 | |
| | | | 100.00 | 0 | |
| | | | | 240.14 | |
| Finished Drug Product | Size 13 Gelatin Capsule | USP | 100.00 | | 1440.84 |

Example 5

Open-Label Studies of MPA Pharmacodynamics in Canine Subjects

Figure 17:
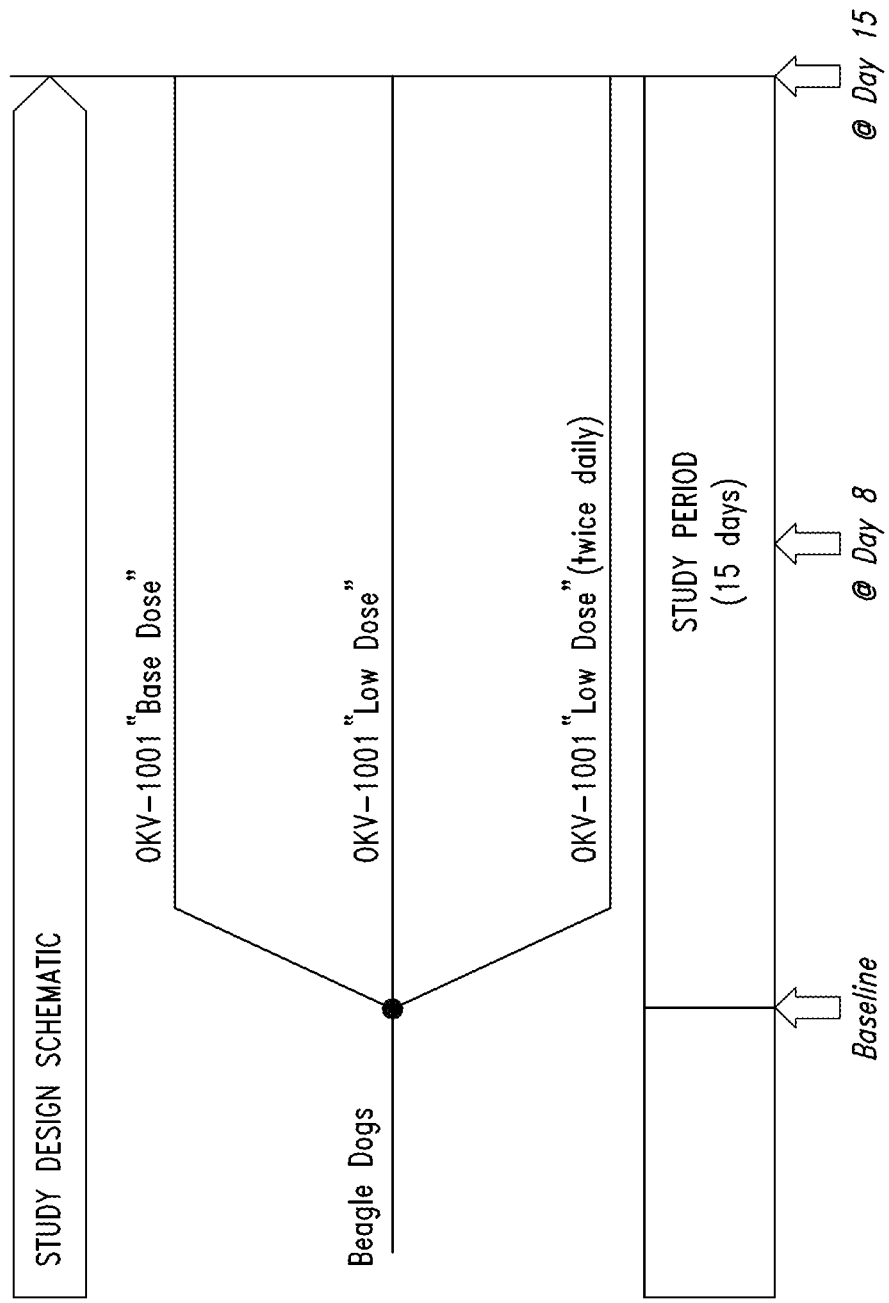
FIGS. 17-26 relate to a 15-day open-label study investigating pharmacodynamic (PD) activity of a controlled-release composition of the present disclosure ("OKV-1001").
Figure 18:
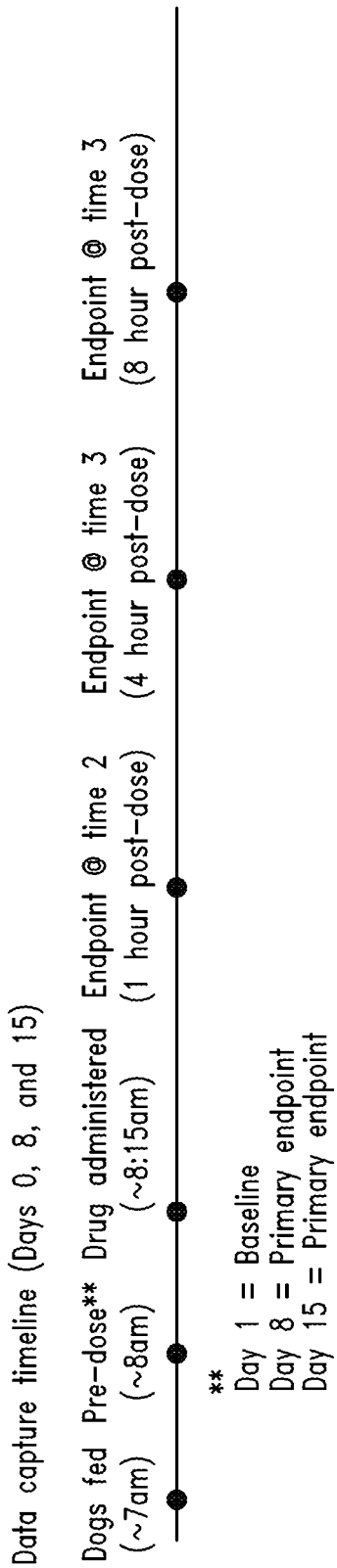

The pharmacodynamic effects of MPA in dogs were investigated in parallel 15-day open-label studies conducted by Absorption Systems (San Diego, Calif.). In one study, male beagle dogs were administered a controlled-release MPA composition of the present disclosure ("OKV-1001") under one of three dosing regimens (270 mg MPA, QD; 180 mg MPA, QD; 180 mg MPA, BID). The study concept is shown schematically in FIG. 17, with the data capture timeline shown at FIG. 18. In a parallel study, dogs received an immediate-release mycophenolate mofetil ("IR-MMF") capsule (120 mg MPA; n=5 dogs, BID) or placebo (n=1). Further details of the study designs are provided below.

Dogs

In both studies, healthy male beagle dogs (Marshall Bioresources, North Rose, N.Y.) with a minimum age of 24 months and an initial body weight of ~10-14 kg were used. Dogs were housed one per cage in a single room. Dogs were identified by ear tattoo.

Feeding and Water Schedule

For at least 3 days prior to study start, animals were feed-acclimated to a food schedule (500 g of a 1:1 mixture of a dry certified laboratory diet (5006 laboratory canine diet from Lab Diet) and canned wet dog food (Alpo™) 1× daily in the morning). The feeding schedule was maintained throughout the duration of both studies. All food was removed 1 hour prior to administration of the first daily dose.

The quantitative amount of food provided and consumed by each animal was recorded throughout both studies. Water was supplied ad libitum to the animals throughout the studies. For dogs that received OKV-1001, body weights for each animal were taken prior to dosing on days 1 and 15. For dogs receiving the IR-MMF, body weights were taken prior to dosing on days 1, 8, and 15. Laboratory personnel wore new, clean, personal protective equipment before entering the room, as well as a facemask and hairnet.

Drug Administration

In the OKV-1001 study, animals received oral capsules comprising either 270 mg or 180 mg MPA QD, or 180 mg MPA BID. QD dosing was performed for Days 1-15. BID dosing was performed for Days 1-14, with a final, single dose on Day 15.

In the MMF-IR study, BID dosing was performed for Days 1-14, with a final, single dose on Day 15.

BID dosing in each study was carried out at approximately 12-hour intervals.

In both studies, drug was administered at approximately the same time on all days by placing the capsule in the back of the throat and flushing with 10 mL water.

General Health and Stool Observations

The general health of each animal was assessed at each timepoint during the course of both studies. If there was not a timepoint, general health observations were performed twice daily during the dose administration times.

The stool of all animals was observed and recorded over the active study duration (Days 1-15). On blood sampling days (Days 1, 8, & 15), the presence or absence of stool was noted at each general health observation timepoint. The time(s) of defecation (post-dose) were recorded. If defecation occurred between observation timepoints, the closest estimation of the time(s) of defecation was recorded. On days with no blood sampling, the stool of animals was observed during general health observations.

The stool of each animal was graded using a modified WALTHAM® feces scoring system, as follows:
Grade 1: Hard, dry
Grade 2: Well-formed and does not leave a trail when picked up.
Grade 3: Moist and beginning to lose form. Leaves a mark when picked up.
Grade 4: Majority of form is lost, poor consistency; viscous.
Grade 5: Watery diarrhea.

Animal Safety

Removal of animals from the study for any reason was recorded.

PK and PD Time Points

Samples were taken for pharmacokinetic ("PK"; mean plasma concentration of MPA) and pharmacodynamic ("PD"; amount of lymphocytes expressing the proliferation marker Ki-67 in a whole blood sample) analysis as follows:

TABLE 17

PK and PD Timepoints for 15-Day Study

| | PK Timepoints | PD Timepoints |
|---|---|---|
| OKV-1001 Day 1 | Pre-dose; 2.5 h($T_{max}$); 4 h; 8 h | Pre-dose; 2.5 h; 4 h; 8h |
| OKV-1001 Day 8 | Pre-dose; 1 h, 2 h, 2.5 h; 4 h; 6 h; 8h | Pre-dose; 2.5 h; 4 h; 8h |
| OKV-1001 Day 15 | Pre-dose; 2.5 h; 4 h; 8 h | Pre-dose; 2.5 h; 4 h; 8h |
| IR-MMF Days 1, 8, and 15 | Pre-dose; 0.75 h ($T_{max}$); 4 h; 8 h | Pre-dose; 0.75 h; 4 h; 8h |

Sample Collection, Preparation, and Storage

Blood was collected from the jugular vein or other accessible vessel. For PK samples, 2 mL whole blood was collected via the jugular vein or other accessible vessel directly into 2 mL chilled (purple top) Vacutainers (a needle and syringe were not used) containing the anticoagulant, $K_2$EDTA, and kept on ice until centrifugation. Blood samples were processed to plasma within 60 minutes of collection, per SOP. Samples were centrifuged at 4° C., at ~3,000×g, for 5 minutes to obtain plasma. Plasma were collected after centrifugation, and then placed into tubes containing a formic acid solution as follows:

1. A 10% formic acid solution in water (1:10 of concentrated, e.g. 88%, formic acid, final concentration is 8.8%) was prepared;
2. Two aliquots of 300 µL of plasma was pipetted from each sample supernatant and added to tubes containing 30 µL of 10% formic acid in water, capped and mixed well (to insure compound stabilization of parent molecule) (plasma was mixed at 10:1 ratio with formic acid, yielding an acidic pH). Note: Two aliquots were collected.
3. Plasma samples were snap frozen on dry ice and stored frozen at −60 to −80° C.

For PD samples, 4 mL blood was collected at each timepoint via the jugular vein or other accessible vessel directly into 4 mL chilled (green top) Vacutainers (a needle and syringe were not used) containing the anticoagulant Sodium Heparin. Samples were refrigerated and shipped same day to Marin Biologic Laboratories, Inc., on ice packs Sample Processing For PK studies, plasma concentrations of MPA were determined using the LC-MS/MS method described in Example 3. For the IR-MMF study, MPA concentrations were analyzed only for the group receiving MMF.

For PD studies, T lymphocyte proliferation was evaluated using a flow cytometry assay as previously described (Bishop K A. Pharmacodynamic assessment of a panel of immunosuppressant drugs in ex-vivo canine T-lymphocyte proliferation. (abstract) 2016 Merial NIH National Veterinary Research Scholars Symposium 2016; Ohio State Universtiy, Columbus, Ohio, USA; Grobman et al., *J. Vet. Pharmacol. Ther.* 2017), with modifications as described below:

Whole blood samples were diluted 1:4 in cRPMI (RPMI 1640+L-glutamine+Pen/strep), plated in a 96 well plate, and incubated with either Concanavalin A (ConA) at 10 µg/mL or cRPMI for 72 hours at 37° C. and 5% $CO_2$.

Following incubation, erythrocytes were lysed and leukocytes were stained with eBioscience™ Fixable Viability Dye eFluor 450 (Thermo Fisher Scientific 65-0863-14), Rat α Dog CD5 APC (Bio-Rad MCA1037APC, clone YKIX322.3), Rat α Dog CD45 RPE (Bio-Rad MCA1037APC, clone YKIX716.13), and Mouse α Human/Dog Ki-67 FITC (Thermo Fisher Scientific 11-5698-80, clone SolA15).

Compensation controls used OneComp eBeads™ Compensation Beads (Thermo Fisher Scientific 01-1111-41) for the surface and intracellular antibodies, and cells for the live/dead marker. Samples were acquired on an Attune NxT flow cytometer (Thermo Fisher Scientific) at a validated speed of 100 µL/min. The following gating strategy was used: Scatter (FSC/SSC)>Singlets (FSC-A/FSC-H)>Live (L-D/SSC)>T cells (CD45+/CD5+)>Proliferating (CD5+/Ki-67+). Generated FCS files were analyzed with FlowJo v 10.4.2 (BD Biosciences).

Results

Lymphocyte Proliferation (Ki-67 Expression)

Figure 19:
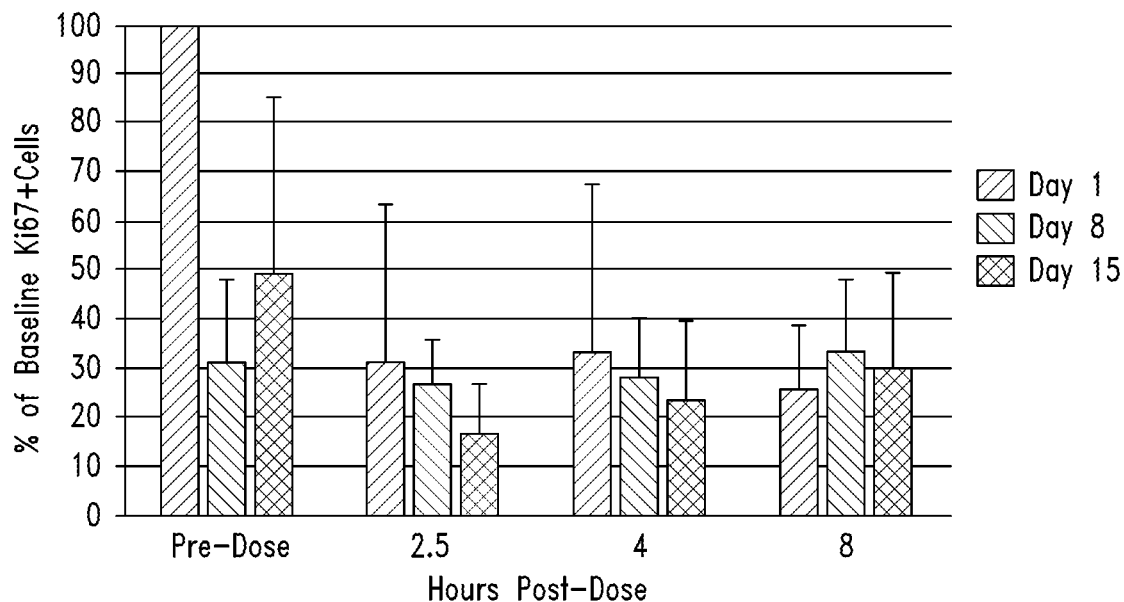
Figure 20:
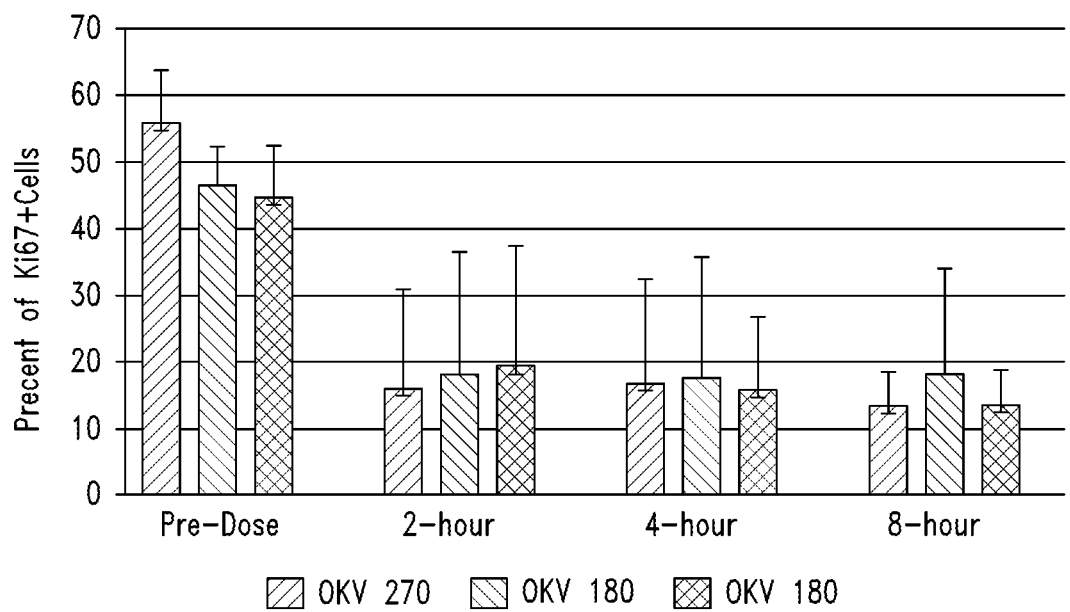
Figure 21:
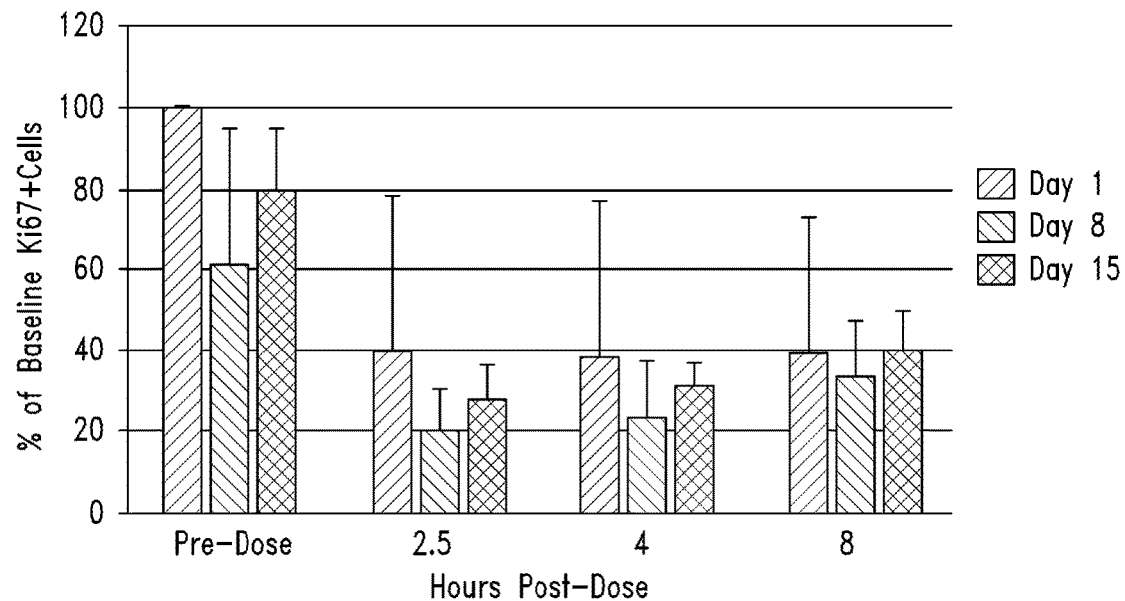

Lymphocyte PD data are provided in FIGS. 19-24. Quite surprisingly, dogs that received OKV-1001 (270 mg) had substantially lower amounts of proliferating lymphocytes prior to dosing on Day 8 as compared to the Day 1 pre-dose level, suggesting that the OKV-1001 formulation had a systemic effect on proliferation (FIG. 19). A similar effect was seen at Day 15. On all days, dogs receiving OKV-1001 had similar reduced levels of Ki-67-expressing cells at all timepoints after dosing (decreases of 50% to 85% relative to baseline), indicating that the OKV-1001 formulations provide sustained suppression of lymphocyte proliferation, with little PD variability over the course of an 8-hour period following administration. Similar results were observed in the dogs that received OKV-1001 (180 mg, QD), as shown in FIG. 21.

Day 1 single-dose PD of OKV-1001 (270 mg and 180 mg (the 180 mg BID group also received only one dose on Day 1)) is shown in FIG. 20. The 8-hour effect on lymphocyte proliferation is similar to the Day 1 data shown in FIG. 19.

Figure 22:
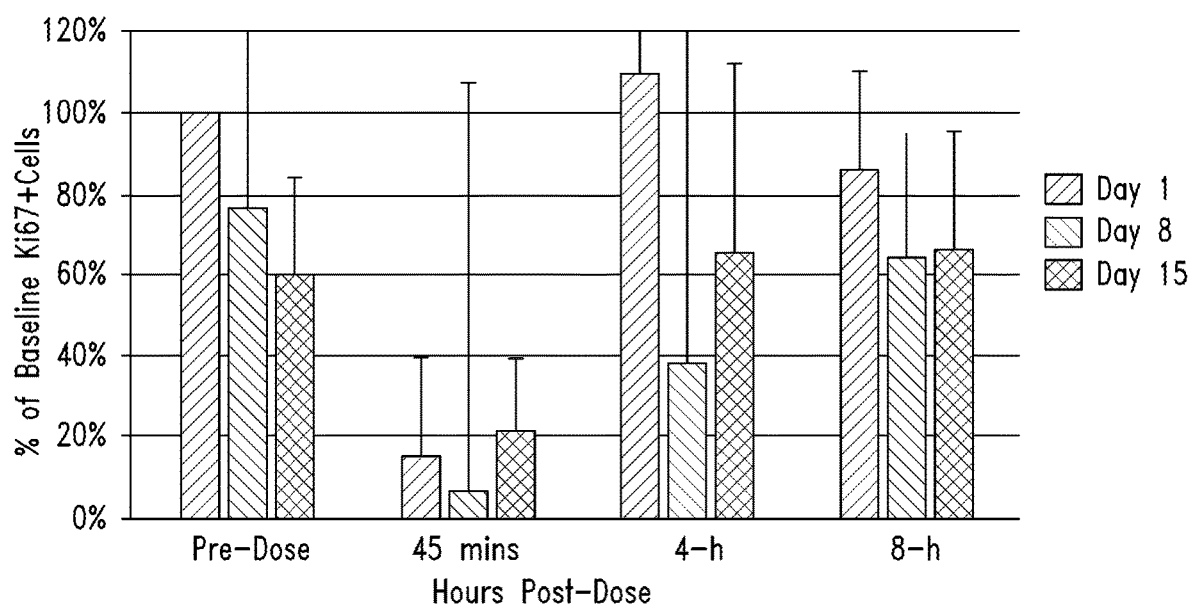

These results were in contrast to the PD data from the IR-MMF group, shown in FIG. 22. In dogs receiving the IR-MMF capsule, an initial sharp reduction in Ki-67-expressing cells was observed at 45 minutes after dosing, but the decrease was not sustained to the same degree as in the dogs receiving OKV-1001. On Day 1, Ki-67+ cells increased above baseline at 4 h, and were at 80% of baseline at 8 h. On Days 8 and 15, Ki-67+ cells were reduced at 4 h and 8 h from the pre-dose baseline, but increased between 4 h and 8 h (moreso on Day 8 than Day 15) and were within 60% of baseline by 8 h.

Figure 23:
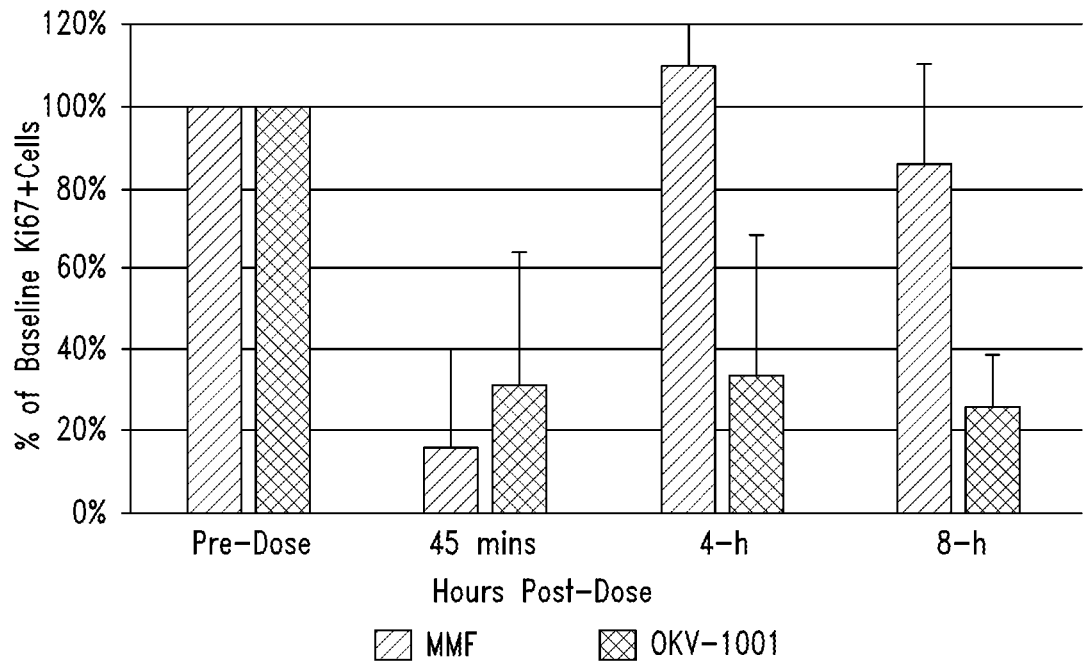
Figure 24:
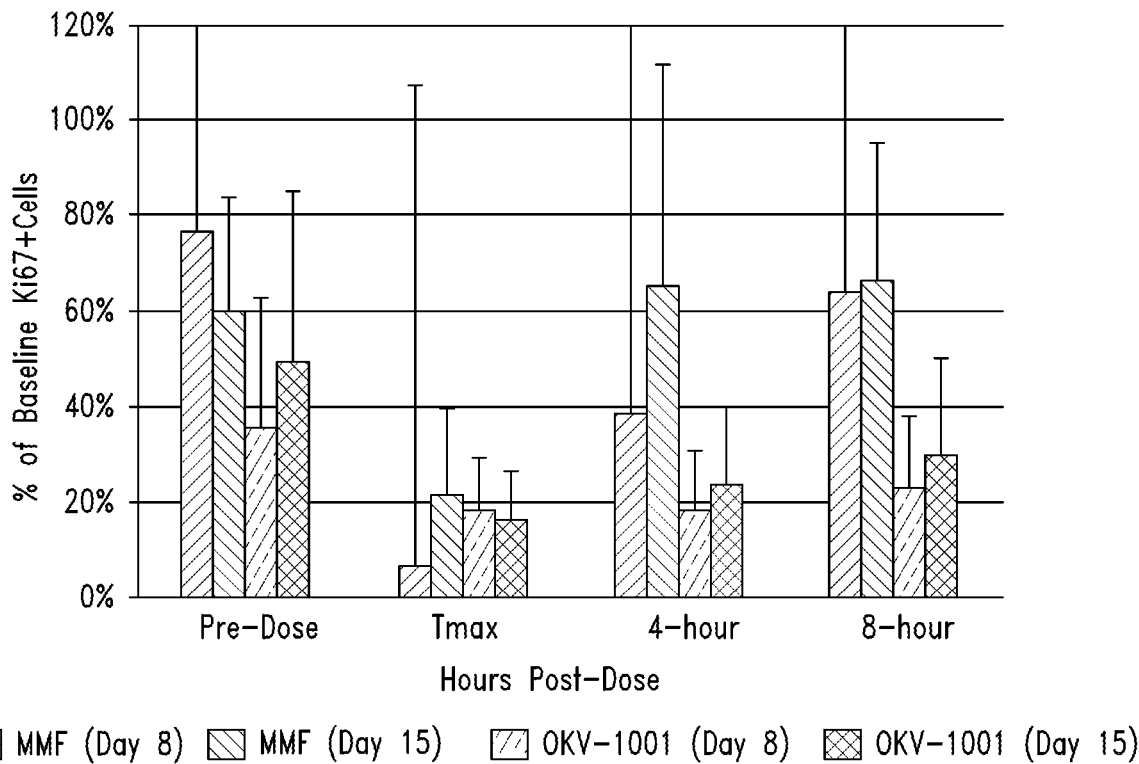
Figure 25:
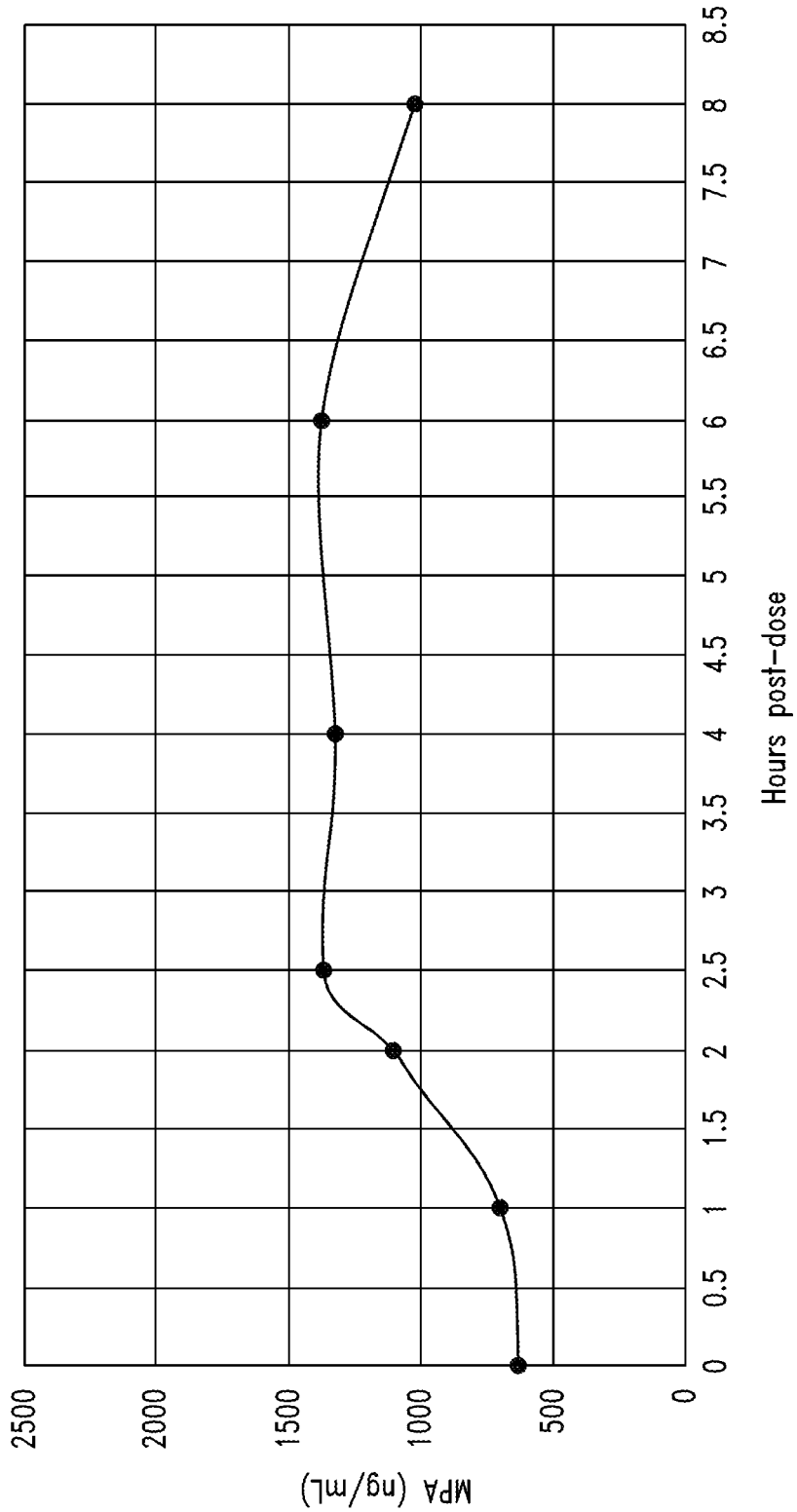

Day 1 PD of IR-MMF and OKV-1001 (270 mg QD) is directly compared in FIG. 23. Overall, dogs receiving the OKV-1001 formulation had a greater sustained reduction in Ki-67+ cells versus baseline as compared to dogs that received IR-MMF. These differences were also seen at Days 8 and 15, as shown in FIG. 24.

Safety

Figure 26:
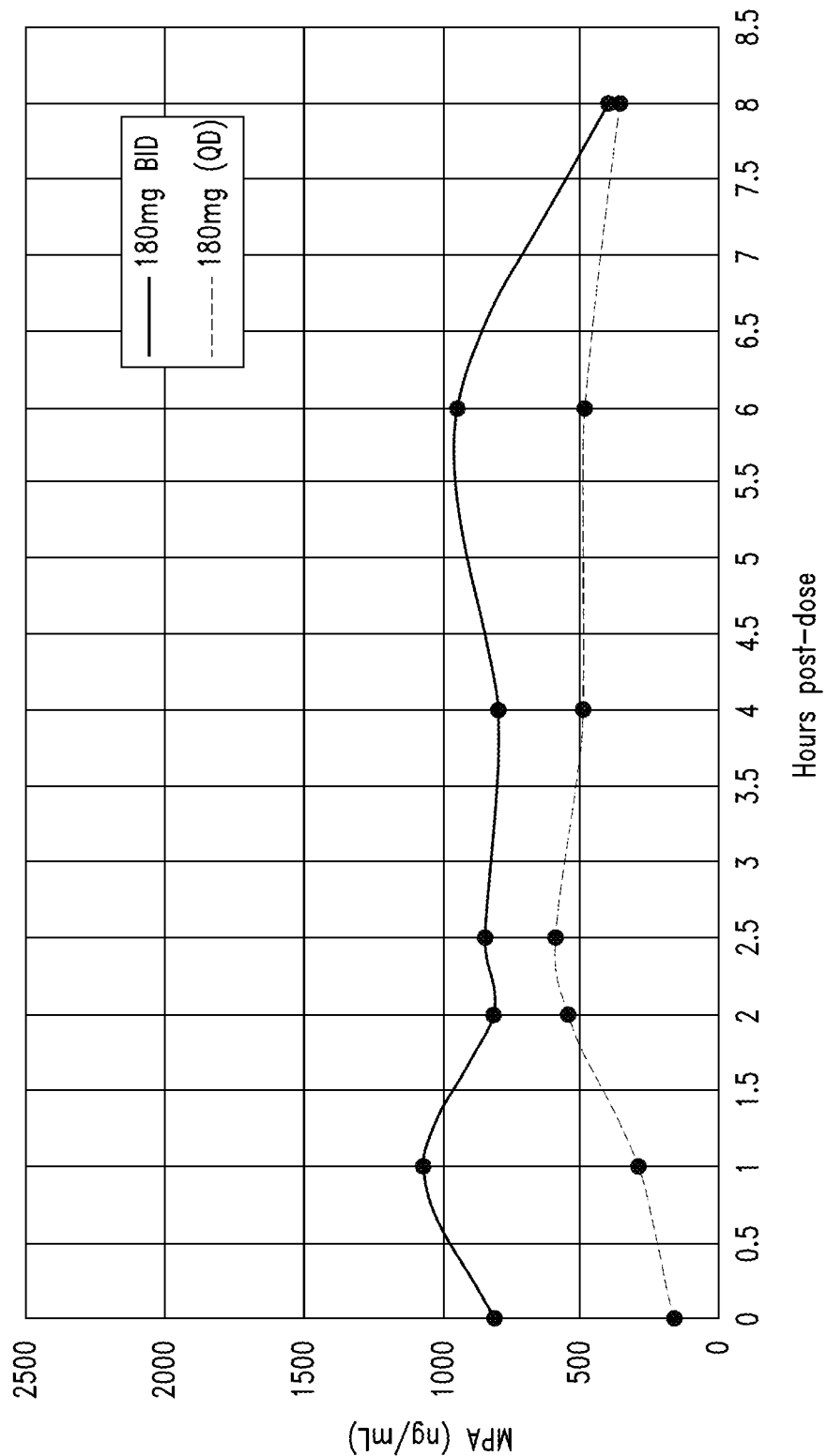
Figure 27:
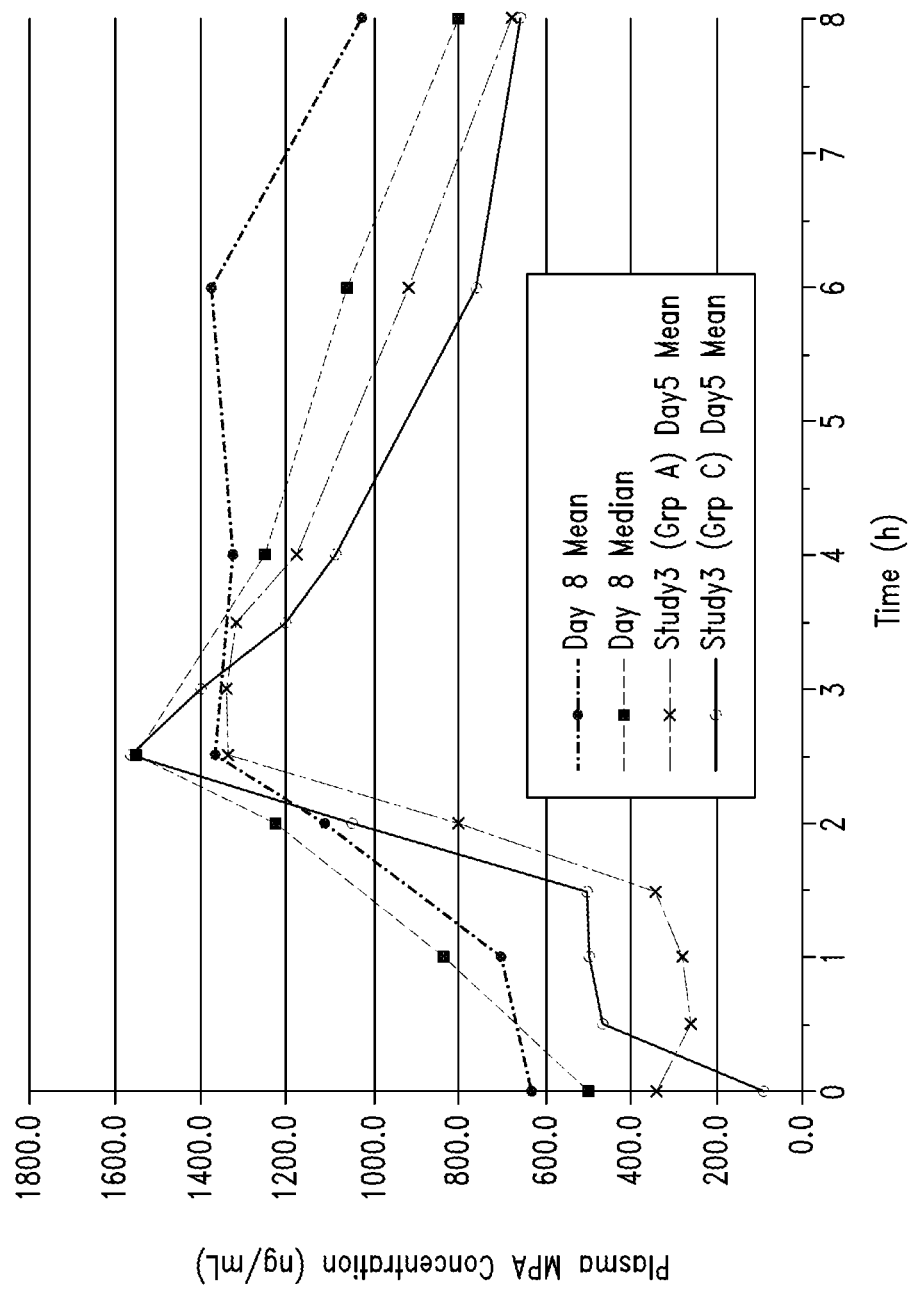
FIG. 27 compares 8-hour pharmacokinetic profiles (mean plasma MPA concentration) of male beagle dogs administered a controlled-release formulation of the present disclosure (270 mg, containing 252 mg MPA; QD) on Day 8 of the 15-day study with average pharmacokinetic profiles from "Group A" and "Group C" treatment groups on Day 5 of the 5-day repeat dosing study illustrated in FIG. 14.

Two dogs receiving 180 mg/kg MPA BID were removed on Day 8 due to severe GI side effects. Interestingly, these dogs had relatively low Cmax MPA values (see FIG. 26). Dogs that received the OKV-1001 formulations (QD administration) did not have any observed severe GI events over the course of the study. This was in contrast to the dogs that received IR-MMF; results are shown in Table 18 below.

TABLE 18

Safety Observations in Dogs Receiving IR-MMF

| | Dog ID | | | | |
|---|---|---|---|---|---|
| Timepoint | Dog 1 | Dog 2 | Dog 3 | Dog 4 | Dog 5 |
| Before Day 10 | No diarrhea or emesis observed | Emesis (Day 6) | | | Diarrhea (Day 8) |
| Day 10 | | | | Diarrhea | |
| Day 11 | | | Soft stool | Diarrhea | |
| Day 12 | | | | Diarrhea | |
| Day 13 | | Diarrhea | Diarrhea & Emesis | Diarrhea & Emesis | Diarrhea |
| Day 14 | | Soft stool | Diarrhea & Emesis | Diarrhea | Soft stool |
| Day 15 | | | Emesis | Diarrhea | Diarrhea |

These results demonstrate surprising advantages of the presently disclosed MDDS and dosing methods. For example, the daily MPA load in 270 mg OKV-1001 (252 mg MPA) is 42% higher than that of 120 mg MMF (BID) (177 mg), but the OKV-1001 had fewer GI side effects than MMF.

In summary, the data from the parallel 15-day pharmacodynamics studies show that MDDS of the present disclosure have a faster onset of systemic action than IR-MMF, have more consistent pharmacodynamics effects (reduced proliferation of lymphocytes) over a 4 and an 8 hour period post-administration, can be advantageously administered once daily as compared to IR-MMF (BID), and are safer than IR-MMF, as determined by the number and severity of gastrointestinal side effects experienced by the dogs.

It will be readily apparent to one of ordinary skill in the relevant arts that other suitable modifications and adaptations to the methods and applications described herein can be made without departing from the scope of any of the embodiments. Further, it is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application Ser. No. 62/470,806, and U.S. Provisional Patent Application Ser. No. 62/503,270, and PCT Application No. PCT/US2018/022266, are incorporated herein by reference, in their entirety. Aspects of the embodiments can be modified, if necessary to employ concepts of the various patents, applications and publications to provide yet further embodiments.

All publications, patents and patent applications mentioned in this specification are herein incorporated by reference to the same extent as if each individual publication, patent or patent application was specifically and individually indicated to be incorporated by reference.

The invention claimed is:

1. A method for suppressing lymphocyte proliferation in a canine subject, comprising orally administering to the canine subject a single dose of a controlled-release composition per day for 15 or more days, wherein the controlled-release formulation comprises a multiparticulate drug delivery system (MDDS) containing a plurality of particulate subunits that each comprise:
   i) a core having a diameter less than about 3 mm;
   ii) an active layer disposed over at least a portion of the core and comprising a mycophenolic acid (MPA) active agent, wherein the MPA active agent is sodium mycophenolate;
   iii) a controlled-release layer disposed over the active layer;

iv) a protective layer comprising a methacrylate-based polymer disposed over the controlled-release layer; and achieving an average plasma [MPA] of about 250 ng/ml to about 3000 ng/ml over about 8 hours following a first dose of the controlled-release formulation, whereupon at 2.5 hours, 4 hours, and 8 hours following the first dose, a percentage of proliferating lymphocytes in a whole blood sample from the subject is reduced by least about 35% as compared to a pre-dose percentage of proliferating lymphocytes in a whole blood sample obtained from the subject 15 or fewer minutes prior to the first dose, as determined using monoclonal antibody Ki-67, and the percentage of proliferating lymphocytes in the whole blood sample from the canine subject is lower than the percentage of proliferating lymphocytes in a whole blood sample obtained from a reference canine subject that received an immediate-release formulation comprising a MPA active agent, and wherein over the 15 days, the canine subject exhibits a reduced number, a reduced severity, or both, of adverse gastrointestinal events as compared to the reference canine subject that received the immediate-release formulation comprising a MPA active agent, wherein the adverse gastrointestinal event is selected from the group consisting of emesis, diarrhea, and soft stool.

2. The method of claim 1, wherein the subject achieves an average plasma [MPA] selected from the group consisting of about 350 ng/ml to about 2000 ng/ml, about 500 ng/ml to about 1700 ng/ml, or about 650 ng/ml to about 1500 ng/ml for about 8 hours following the first dose.

3. The method of claim 1, whereupon at 2.5 hours following the first dose, the percentage of proliferating lymphocytes in a whole blood sample from the subject is reduced by a percentage selected from the group consisting of at least about 40%, 45%, 50%, 55%, 60%, 65%, 70%, 75%, or 80%, relative to the pre-dose percentage of proliferating lymphocytes in a whole blood sample obtained from the subject 15 or fewer minutes prior to the first dose.

4. The method of claim 1, wherein the subject achieves a plasma [MPA] Cmax selected from the group consisting of:
(i) about 2500 ng/ml over about 8 hours following the first dose, and a plasma [MPA] Cmin of no less than about 250 ng/ml from about 2.5 to about 8 hours following the first dose;
(ii) about 2000 ng/mL over about 8 hours following the first dose, and a plasma [MPA] Cmin of no less than about 500 ng/ml from about 2.5 to about 8 hours following the first dose;
(iii) about 1500 ng/ml over about 8 hours following the first dose, and a plasma [MPA] Cmin of no less than about 600 ng/ml from about 2.5 to about 8 hours following the first dose;
(iv) about 700 ng/ml over about 8 hours following the first dose, and a plasma [MPA] Cmin of no less than about 250 ng/ml from 2.5 to about 8 hours following the first dose;
(v) about 600 ng/ml over about 8 hours following the first dose, and a plasma [MPA] Cmin of no less than about 250 ng/ml from about 2.5 to about 8 hours following the first dose; and
(vi) about 500 ng/ml over about 8 hours following the first dose, and a plasma [MPA] Cmin of no less than about 250 ng/ml from about 2.5 to about 8 hours following the first dose.

5. The method of claim 1, comprising administering the controlled-release composition to the subject when the subject is in a fed state.

6. The method of claim 1, whereupon 24 hours after the dose of each of the second, third, fourth, fifth, sixth, seventh, eighth, ninth, tenth, eleventh, twelfth, thirteenth, fourteenth, or fifteenth days, or prior to any subsequent dose, the percentage of proliferating lymphocytes in a whole blood sample from the subject is reduced by a percent selected from the group consisting of about 35%, about 40%, about 45%, about 50%, about 55%, about 60%, about 65%, about 70%, or about 75%, relative to the pre-dose percentage of proliferating lymphocytes in a whole blood sample obtained from the subject 15 or fewer minutes prior to the dose of the first day.

7. The method of claim 1, wherein the first dose comprises the MPA active agent at about 3 mg/kg to about 35 mg/kg.

8. The method of claim 1, wherein the first dose comprises from about 3 mg to about 2200 mg of the MPA active agent.

9. The method of claim 1, wherein the subject:
(i) has, or is suspected of having, an autoimmune disease or disorder associated with aberrant lymphocyte proliferation and/or activation;
(ii) has undergone, is undergoing, or will undergo an organ transplant and/or artificial implant; or
(iii) both of (i) and (ii).

10. The method of claim 1, whereupon at 4 hours following the first dose, the percentage of proliferating lymphocytes in a whole blood sample from the subject is reduced by a percentage selected from the group consisting of at least about 40%, 45%, 50%, 55%, 60%, 65%, 70%, 75%, or 80%, relative to the pre-dose percentage of proliferating lymphocytes in a whole blood sample obtained from the subject 15 or fewer minutes prior to the first dose.

11. The method of claim 1, whereupon at 8 hours following the first dose, the percentage of proliferating lymphocytes in a whole blood sample from the subject is reduced by a percentage selected from the group consisting of at least about 40%, 45%, 50%, 55%, 60%, 65%, 70%, 75%, or 80%, relative to the pre-dose percentage of proliferating lymphocytes in a whole blood sample obtained from the subject 15 or fewer minutes prior to the first dose.

12. The method of claim 1, whereupon 24 hours after the dose of each of the seventh, eighth, ninth, tenth, eleventh, twelfth, thirteenth, fourteenth, or fifteenth days, or prior to any subsequent dose, the percentage of proliferating lymphocytes in a whole blood sample from the subject is reduced by a percent selected from the group consisting of about 35%, about 40%, about 45%, about 50%, about 55%, about 60%, about 65%, about 70%, or about 75%, relative to the pre-dose percentage of proliferating lymphocytes in a whole blood sample obtained from the subject 15 or fewer minutes prior to the dose of the first day.

13. The method of claim 9, wherein the autoimmune disease or disorder comprises atopic dermatitis, arthritis, myasthenia gravis, celiac disease, diabetes mellitus type 1, Grave's disease, inflammatory bowel disease, multiple sclerosis, psoriasis, rheumatoid arthritis, systemic lupus erythematosus, Behçet's disease, pemphigus vulgaris, refractory incomplete systemic lupus erythematosus, lupus nephritis, immunoglobulin A nephropathy, small vessel vasculitides, scleroderma (systemic sclerosis or SSc), idiopathic thrombocytopenia purpura (ITP), psoriasis, apernicious anemia, vitiligo, autoimmune hemolytic disease, glomerulonephritis, immune cytopenias, meningoencephalomyelitis, subepidermal blistering autoimmune disease, immunobullous diseases, cutaneous vasculitis, recurrent erythema multiforme, erythema nodosum, lichen planus, cutaneous Crohn's disease, sarcoidosis, hepatitis, pyoderma gangrenosum, or any combination thereof.

14. The method of claim 1, wherein the core is an extruded core and sodium mycophenolate is contained within the extruded core.

15. The method of claim 1, wherein each particulate subunit of the plurality comprises a seal coat layer between the MPA active layer and the controlled-release layer.

16. The method according to claim 15, wherein the seal coat comprises a cellulose polymer, a poly(vinyl alcohol), a hydroxypropyl methylcellulose polymer, a methylcellulose polymer, a hydroxyethylcellulose polymer, or any combination thereof.

17. The method according to claim 1, wherein the controlled-release layer comprises a cellulose polymer, an acrylate polymer, a cellulose acetate, a cellulose acetate butyrate, an ethyl cellulose, a hydroxypropyl methylcellulose polymer, a methylcellulose polymer, a poly(vinyl acrylate) (PVA) polymer, or any combination thereof.

18. The method according to claim 1, wherein the controlled-release layer comprises ethyl cellulose.

19. The method of claim 1, whereupon 24 hours after the dose of the seventh day, and prior to any subsequent dose, the percentage of proliferating lymphocytes in a whole blood sample from the subject is reduced by about 35%, or more, relative to the amount of proliferating lymphocytes in a whole blood sample obtained from the subject 15 or fewer minutes prior to the dose of the first day.

20. The method of claim 1, whereupon 24 hours after the dose of the fourteenth day, and prior to any subsequent dose, the percentage of proliferating lymphocytes in a whole blood sample from the subject is reduced by about 35%, or more, relative to the amount of proliferating lymphocytes in a whole blood sample obtained from the subject 15 or fewer minutes prior to the dose of the first day.

\* \* \* \* \*